United States Patent [19]

Allen et al.

[11] Patent Number: 6,096,920
[45] Date of Patent: Aug. 1, 2000

[54] PREPARATION OF CARBOXYLIC COMPOUNDS AND THEIR DERIVATIVES

[75] Inventors: Robert H. Allen; R. Carl Herndon, Jr.; Kannappan C. Chockalingam; W. Dirk Klobucar; Gary D. Focht; Tse-Chong Wu, all of Baton Rouge, La.; Gary D. Heidebrecht; Joseph D. McLean, both of Orangeburg, S.C.; Yaping Zhong; Thorsten W. Brockmann, both of Columbia, S.C.; Ronny W. Lin, Baton Rouge, La.; William J. Layman, Jr., Baton Rouge, La.; Ranjit K. Roy, Baton Rouge, La.

[73] Assignee: Albemarle Corporation, Richmond, Va.

[21] Appl. No.: 09/111,935

[22] Filed: Jul. 8, 1998

Related U.S. Application Data

[63] Continuation-in-part of application No. 08/780,308, Jan. 8, 1997, abandoned, and a continuation-in-part of application No. 08/780,310, Jan. 8, 1997, and a continuation-in-part of application No. 08/951,736, Oct. 16, 1997, abandoned.

[51] Int. Cl.[7] .................................................. C07C 51/10
[52] U.S. Cl. .............................. 562/406; 560/52; 560/55; 560/56; 560/105; 562/460; 562/465; 562/466; 562/496; 585/438
[58] Field of Search ................................ 562/406, 460, 562/465, 466, 496; 560/52, 55, 56, 105; 585/438

[56] References Cited

U.S. PATENT DOCUMENTS

| | | | |
|---|---|---|---|
| 3,159,649 | 12/1964 | Brown et al. | 260/343.3 |
| 3,228,831 | 1/1966 | Nicholson et al. | 167/53 |
| 3,385,886 | 5/1968 | Nicholson et al. | 260/515 |
| 3,562,336 | 2/1971 | Nelson | 260/613 |
| 3,600,437 | 8/1971 | Marshall | 260/520 |
| 3,626,012 | 12/1971 | Fried et al. | 260/599 |
| 3,637,767 | 1/1972 | Alvarez | 260/348 R |
| 3,641,127 | 2/1972 | Farge et al. | 260/516 |
| 3,651,106 | 3/1972 | Harrison | 260/429 R |
| 3,651,148 | 3/1972 | Nelson | 260/606.5 B |
| 3,651,149 | 3/1972 | Harrison | 260/606.5 B |
| 3,652,683 | 3/1972 | Harrison | 260/612 D |
| 3,658,858 | 4/1972 | Harrison | 260/429 R |
| 3,658,863 | 4/1972 | Harrison | 260/438.1 |
| 3,663,584 | 5/1972 | Alvarez | 260/429.9 |
| 3,663,713 | 5/1972 | Fried et al. | 424/333 |
| 3,681,432 | 8/1972 | Nelson | 260/473 F |
| 3,683,015 | 8/1972 | Dyson | 260/520 |
| 3,686,183 | 8/1972 | Dyson | 260/284 |
| 3,694,476 | 9/1972 | Alvarez | 260/429 R |
| 3,720,708 | 3/1973 | Halpern | 260/519 |
| 3,755,427 | 8/1973 | Adams et al. | 260/515 A |
| 3,758,544 | 9/1973 | Alvarez | 260/465 F |
| 3,787,580 | 1/1974 | Fried et al. | 424/308 |
| 3,821,253 | 6/1974 | Fried et al. | 260/340.9 |
| 3,828,033 | 8/1974 | Nelson | 260/240 R |
| 3,873,594 | 3/1975 | Alvarez | 260/465 F |

(List continued on next page.)

FOREIGN PATENT DOCUMENTS

| | | |
|---|---|---|
| 59-10545 | 1/1984 | Japan . |
| 380563 | 9/1932 | United Kingdom . |
| 1160725 | 8/1969 | United Kingdom . |

OTHER PUBLICATIONS

DeVries et al; Synthesis of High–Purity o– and p–Vinyltoluenes by the Heck Palladium–Catalyzed Arylation Reaction; Organometallics (1994) vol. 13, pp. 2405–2411.

Heck; "Palladium Reagents in Organic Syntheses"; Academic Press (1985), pp. 276–291.

Patel, et al; "Palladium–Catalyzed Vinylation of Conjugated Dienes"; J. Org. Chem. (1979) vol. 44, pp. 918–921.

Lewis; "Methylation of Phenol by Dimethyl Sulfate"; Industrial and Engineering Chemistry (1930), vol. 22, pp. 397–398.

Ohta et al; "Asymmetric Hydrogenation of Unsaturated Carboxylic Acids Catalyzed by BINAP–Ruthenium(II) Complexes"; J. Org. Chem. (1987), vol. 52, pp. 3174–3176.

Pinder; "The Hydrogenolysis of Organic Halides"; Synthesis, (1980), pp. 425–452.

Rajagopal et al; "Mechanism of Palladium–Catalyzed Transfer Hydrogenolysis of Aryl Chlorides by Formate Salts[1]"; J. Org. Chem. (1995), vol. 60, pp. 1347–1355.

Alper et al; "The Regiospecific Palladium Catalysed Hydrocarboxylation of Alkenes under Mild Conditions"; J. Chem. Soc. Chem. Commun. (1983), pp. 1270–1271.

Horeau, et al; No. 287. "Steroids devoid of C nucleus (III). On a lactone corresponding to an isomer of bis–dehydroestrolactone"; Soc. Chim., 5th Series, 1959—Reports, pp. 1854–1857 translation—including copy of original text.

Heitz et al; "Synthesis of monomers and polymers by the Heck reaction"; Makromoi Chem. (1988) vol. 189, pp. 119–127.

(List continued on next page.)

Primary Examiner—Paul J. Killos
Attorney, Agent, or Firm—Philip M. Pippenger

[57] ABSTRACT

Palladium-catalyzed arylation of an olefin (e.g., ethylene) with an aromatic halide (e.g., 2-bromo-6-methoxynaphthalene, m-bromobenzophenone, or 4-isobutyl-1-bromobenzene) is conducted in specified media. After a special acid or base phase separation procedure, palladium-catalyzed carbonylation of the olefinically-substituted aromatic intermediate is conducted in specified media using CO and water or an alcohol to form arylalkylcarboxylic acid or ester or substituted arylalkylcarboxylic acid or ester (e.g., racemic 2-(6-methoxy-2-naphthyl)propionic acid, 2-(3-benzoylphenyl)propionic acid, or 2-(4-isobutylphenyl)propionic acid). Catalyst recovery procedures enabling recycle of catalyst residues and efficient recovery of amine hydrogen halide scavenger and solvent used in the arylation reaction are described, as well as novel, highly efficient methods of conducting the carbonylation reaction. The technology is economical and suitable for use on an industrial scale whereby reaction mixtures can be efficiently separated into the desired component mixtures without need for excessive capital investment or tedious, time-consuming operations. High yields of high purity products can be achieved.

181 Claims, No Drawings

U.S. PATENT DOCUMENTS

| | | | |
|---|---|---|---|
| 3,896,157 | 7/1975 | Fried et al. | 260/469 |
| 3,904,682 | 9/1975 | Fried et al. | 260/520 |
| 3,904,683 | 9/1975 | Day et al. | 260/520 |
| 3,906,038 | 9/1975 | Fried et al. | 260/507 R |
| 3,914,293 | 10/1975 | Fried et al. | 260/512 C |
| 3,922,299 | 11/1975 | Heck | 260/476 R |
| 3,923,900 | 12/1975 | Petracek | 260/590 |
| 3,935,273 | 1/1976 | Fried et al. | 260/600 R |
| 3,958,012 | 5/1976 | Fried et al. | 424/333 |
| 3,959,364 | 5/1976 | Armitage et al. | 260/515 R |
| 3,960,936 | 6/1976 | Fried et al. | 260/488 CD |
| 3,960,957 | 6/1976 | Alvarez | 260/566 A |
| 3,975,432 | 8/1976 | Alvarez | 260/520 R |
| 3,978,116 | 8/1976 | Fried et al. | 260/500.5 H |
| 3,978,124 | 8/1976 | Fried et al. | 260/558 R |
| 3,980,699 | 9/1976 | Fried et al. | 260/515 R |
| 3,988,365 | 10/1976 | Gallegra | 260/520 D |
| 3,994,968 | 11/1976 | Alvarez | 260/520 D |
| 3,998,966 | 12/1976 | Fried et al. | 424/308 |
| 4,001,301 | 1/1977 | Fried et al. | 260/473 F |
| 4,005,093 | 1/1977 | Zenitz | 260/293.62 |
| 4,009,197 | 2/1977 | Fried et al. | 260/473 F |
| 4,013,583 | 3/1977 | Knifton | 252/415 |
| 4,028,366 | 6/1977 | Zenitz | 260/293.62 |
| 4,045,485 | 8/1977 | Fried et al. | 260/566 A |
| 4,107,439 | 8/1978 | Walker et al. | 560/55 |
| 4,135,051 | 1/1979 | Walker | 560/105 |
| 4,142,054 | 2/1979 | Amin et al. | 560/105 |
| 4,144,397 | 3/1979 | Matthews et al. | 562/466 |
| 4,233,316 | 11/1980 | Gardocki | 424/317 |
| 4,239,914 | 12/1980 | Campolmi et al. | 562/466 |
| 4,246,164 | 1/1981 | Felder et al. | 260/501.17 |
| 4,246,193 | 1/1981 | Holton | 260/501.17 |
| 4,379,148 | 4/1983 | Sato et al. | 424/232 |
| 4,395,571 | 7/1983 | Dvorak | 562/466 |
| 4,545,992 | 10/1985 | Kamishita | 514/161 |
| 4,560,777 | 12/1985 | Giordano et al. | 549/374 |
| 4,571,333 | 2/1986 | Hsiao et al. | 424/22 |
| 4,605,758 | 8/1986 | Scholemer | 562/418 |
| 4,609,766 | 9/1986 | Giordano et al. | 568/592 |
| 4,621,152 | 11/1986 | Bernini | 562/401 |
| 4,623,736 | 11/1986 | Walker et al. | 549/369 |
| 4,628,123 | 12/1986 | Borsotti | 568/634 |
| 4,654,438 | 3/1987 | Scloemer | 562/496 |
| 4,665,224 | 5/1987 | Mora | 560/56 |
| 4,697,036 | 9/1987 | Giordano et al. | 562/418 |
| 4,723,033 | 2/1988 | Erickson | 560/56 |
| 4,734,507 | 3/1988 | Giordano et al. | 549/450 |
| 4,736,061 | 4/1988 | Piccolo et al. | 562/466 |
| 4,749,804 | 6/1988 | Schloemer | 558/51 |
| 4,766,225 | 8/1988 | Sayo et al. | 556/16 |
| 4,803,079 | 2/1989 | Hsiao et al. | 424/468 |
| 4,810,819 | 3/1989 | Giordano et al. | 562/56 |
| 4,857,462 | 8/1989 | Maier et al. | 435/197 |
| 4,864,063 | 9/1989 | Piccolo et al. | 568/328 |
| 4,919,803 | 4/1990 | Doyle et al. | 210/198.2 |
| 4,962,230 | 10/1990 | Takaya et al. | 562/433 |
| 4,981,995 | 1/1991 | Elango et al. | 562/406 |
| 5,034,416 | 7/1991 | Smith | 514/568 |
| 5,055,611 | 10/1991 | Lin et al. | 562/406 |
| 5,136,069 | 8/1992 | DeVries et al. | 556/453 |
| 5,243,068 | 9/1993 | De Vries et al. | 560/205 |
| 5,243,088 | 9/1993 | Jacquot et al. | 568/656 |
| 5,256,829 | 10/1993 | Jacquot | 568/737 |
| 5,313,001 | 5/1994 | Heitz et al. | 568/655 |
| 5,315,026 | 5/1994 | Wu | 560/105 |
| 5,426,243 | 6/1995 | Lecouve | 568/737 |
| 5,536,870 | 7/1996 | Wu | 560/56 |

OTHER PUBLICATIONS

Marques et al; "Facile Hydrodehalogenation with $H_2$ and Pd/C Catalyst under Multiphase Conditions. 2. Selectivity and Kinetics"; J. Org. Chem. (1994) vol. 59, pp. 3830–3837.

Marques et al; Facile Hydrodehalogenation with $H_2$ and Pd/C Catalyst under Multiphase Conditions. 3. Selecive Removal of Halogen from Functionalized Aryl Ketones. 4. Aryl Halide–Promoted Reduction of Berzyl Alcohols to Alkanes; J. Org. Chem. (1995), vol. 60, pp. 2430–2435.

Piccolo et al; "Zinc Salt Catalyzed Rearrangement of Acetals of Optically Active 1–Chloroethyl Ketones: Synthesis of Optically Active 2–Arylpropionic Acids and Esters[1]"; J. Org. Chem. (1987), vol. 52, pp. 10–14.

Stinson; "Technological Innovation Thrives in Fine Chemicals Industry"; Science/Technology; C & EN News, (1996), pp. 35–61.

Marques, et al; "Facile Hydrodehalogenation with Hydrogen and Pd/C Catalyst under Multiphase Conditions"; J. Org. Chem. 1993, vol. 58; No. 19, pp. 5256–5260.

Mori et al., "Arylation of Olefin with Iodobenzene Catalyzed by Palladium", Bulletin of the Chemical Society of Japan, vol. 46, 1973, pp. 1505–1508.

Plevyak et al., "Palladium–Catalyzed Arylation of Ethylene", J. Org. Chem., vol. 43, No. 12, 1978, pp. 2454–2456.

PREPARATION OF CARBOXYLIC COMPOUNDS AND THEIR DERIVATIVES

REFERENCE TO RELATED APPLICATIONS

This application is continuation-in-part of commonly-owned U.S. applications Ser. Nos. 08/780,308 abd and 08/780,310, pending both filed Jan. 8, 1997, and Ser. No. 08/951,736 filed Oct. 16, 1997, now abandoned.

TECHNICAL FIELD

This invention relates to the production of certain carboxylic acids, or derivatives thereof, such as salts or esters.

BACKGROUND

The palladium-catalyzed vinylation of organic halides provides a very convenient method for forming carbon-carbon bonds at unsubstituted vinylic positions. The reaction, reported by Heck (*Palladium Reagents in Organic Synthesis*, Academic Press, Canada 1985) can be used to prepare fine organics, pharmaceuticals, and specialty monomers. For example, the reaction allows a one-step synthesis of substituted styrenes from aryl bromides and is an excellent method for preparation of a wide variety of styrene derivatives. Heitz et al., *Makromol. Chem.*, 189, 119 (1968).

Vinyl toluenes have been reported as the product of a homogeneous palladium-catalyzed coupling of ethylene with bromotoluenes. The reaction is performed in a two-phase solvent system composed of N,N-dimethyl formamide and water. R. A. DeVries et al., *Organometallics*, 13, 2405 (1994).

U.S. Pat. Nos. 5,136,069 and 5,243,068 to R. A. DeVries et al. describe preparation of vinylically-unsaturated compounds by reaction of a halogenated organic compound with a hydrolytically-stable, vinylically-unsaturated precursor compound in the presence of (a) a homogeneous zerovalent palladium catalyst complex, (b) an inorganic hydrogen halide acceptor and (c) a diluent which is either water or an aqueous solution containing up to 95% by volume of organic solvent.

Arylation of propylene, ethylene, styrene, and methyl acrylate with iodobenzene was found to be catalyzed by metallic palladium in methanol to give methylstyrene, styrene, t-stilbene, and methyl cinnamate, respectively. Their yields and selectivities increased significantly by the addition of excess potassium acetate as an acceptor of hydriodic acid formed. Mori et al., *Bull. Chem. Soc., Japan*, 46, 1505 (1973).

A variety of styrene derivatives and 3-vinylpyridine were prepared in moderate to good yields by the palladium-tri-o-tolylphosphine catalyzed reaction of ethylene with aryl bromides or 3-bromopyridine, respectively. (Plevyak et al., *J. Org. Chem.*, 43, 2454 (1970).

Alper et al. in *J. Chem Soc. Chem. Comm.*, 1983, 1270–1271, discloses that alkenes can react with carbon monoxide, water, hydrochloric acid and a mixture of palladium and copper to produce the hydracarbonylated branched chain carboxylic acid. Oxygen is necessary to succeed in the reaction.

A process for preparing the branched chain carboxylic acid, ibuprofen, is described in Japanese Patent Application (Kokai) No. 59-10545 (Mitsubishi Petrochemical, published January, 1984), which teaches that ibuprofen can be prepared by reacting p-isobutylstyrene with carbon monoxide and water or an alcohol in the presence of a palladium(II) catalyst and a peroxide, e.g., cumyl hydroperoxide.

A process for preparing aryl substituted aliphatic carboxylic acids or their alkyl esters is disclosed in U.S. Pat. No. 5,315,026. A 1-aryl substituted olefin is reacted with carbon monoxide in the presence of water or an alcohol at a temperature between about 25° C. and about 200° C. A mixture useful as a catalyst is a palladium compound and a copper compound with at least one acid-stable ligand. Ligands which may be used include monodentate or multidentate electron-donating substances such as those containing elements P, N, O and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like.

U.S. Pat. No. 5,536,870 describes the preparation of substituted olefins by the palladium-catalyzed coupling of vinyl or substituted vinyl compounds with organic halides, and also the formation of carboxylic acids and esters from such substituted olefins. The substituted olefinic compounds are formed by reacting an organic halide with a vinyl or substituted vinyl compound in the presence of a catalytically effective amount of palladium or a salt of palladium having a valence of 1 or 2, and a tertiary phosphine ligand such as neomenthyldiphenylphosphine. This reaction is carried out in the presence or absence of a solvent such as acetonitrile, tetrahydrofuran, dioxane, or dimethylformamide. An important utility of the substituted olefins formed in this manner is the subsequent conversion of such substituted olefins to carboxylic acids or derivatives thereof such as salts or esters (e.g., profen compounds) by carbonylation with carbon monoxide using catalytic systems and reaction conditions described in U.S. Pat. No. 5,536,870.

Despite the above and other technological developments in the field, a need exists for a new, economical, commercially feasible way of producing various arylalkylcarboxylic and/or substituted arylalkylcarboxylic acids on an industrial scale whereby complex reaction mixtures can be efficiently separated into the desired component mixtures without need for excessive capital investment or tedious, time-consuming operations.

Palladium catalysts and tertiary phosphine ligands which have been found effective as catalyst components in the preparation of arylalkylcarboxylic acids and substituted arylalkylcarboxylic acids such as profen-type pharmaceuticals are quite expensive. While U.S. Pat. No. 5,055,611 describes an effective way of recovering and regenerating a carbonylation catalyst used in the preparation of ibuprofen, the process requires a reduced pressure distillation in order to separate the ibuprofen from the carbonylation residue. Reduced pressure distillation when conducted on a plant scale is an expensive and capital-intensive operation. Moreover, there are practical limitations and economic constraints on the materials which can be separated and recovered by reduced pressure distillation. In particular, polycyclic substituted arylalkylcarboxylic acids, such as racemic 2-(6-methoxy-2-naphthyl)propionic acid, α-dl-2-(3-phenoxyphenyl)propionic acid; and 2-(3-benzoylphenyl) propionic acid, have significantly higher boiling points than ibuprofen. Thus separating such substances from catalyst residues, if possible by reduced pressure distillation, would require special equipment and operating conditions, e.g., high vacuum, wiped film evaporators, etc. Also under the conditions needed for such operations, the possibility exists for some product and/or catalyst component losses to be encountered. Thus a need exists for an efficient way of separating arylalkylcarboxylic acids and/or substituted arylalkylcarboxylic acids, especially substituted arylalkylcarboxylic acids having more than one aromatic ring in the molecule, from expensive residual catalyst components used in their preparation, which does not require reduced pressure distillation with its attendant high investment and operating costs, and which provides an active organic-soluble catalyst residue for reuse via recycle without need for regenerating such residue.

This invention makes it possible to effectively fulfill each of the above-identified needs.

SUMMARY OF THE INVENTION

This invention provides, inter alia, process technology enabling the efficient large-scale production of certain aromatically-substituted aliphatic carboxylic acids and their acid derivatives such as salts or esters, including profen-type compounds, which are well-known analgesic or anti-inflammatory agents.

In accordance with a first embodiment of this invention, there is provided a process which comprises:

a) conducting a palladium-catalyzed arylation of an olefin with aryl halide and/or substituted aryl halide in a liquid medium formed from (i) one or more liquid polar organic solvent/diluents, and (ii) one or more secondary or tertiary amines that (1) boil(s) below the boiling temperature of the solvent/diluent if only one solvent/diluent is used or (2) that boil(s) below the boiling temperature of at least one, but not necessarily all, of the polar solvent/diluents used in forming said medium if more than one solvent/diluent is used, to form a reaction mixture comprising olefinically-substituted aromatic compound, amine-hydrohalide and one or more polar organic solvents;

b) mixing (i) a concentrated aqueous solution of inorganic base having a base strength greater than the base strength of the one or more secondary or tertiary amines, with (ii) at least a portion of the reaction mixture to convert amine-hydrohalide therein to free amine and inorganic halide, and to form (i) an aqueous phase containing dissolved inorganic halide, and (ii) an organic phase comprising olefinically-substituted aromatic compound, one or more polar organic solvents and free amine;

c) separating the foregoing phases from each other;

d) distilling off substantially all of the amine from the organic phase under low temperature and pressure conditions that suppress thermal oligomerization of the olefinically-substituted aromatic compound contained in the residual liquid phase, to thereby form a distilland composed predominately of olefinically-substituted aromatic compound and one or more polar organic solvents; and e) conducting a palladium-catalyzed carbonylation of at least a portion of said olefinically-substituted aromatic compound with carbon monoxide and water and/or alcohol in a liquid medium comprising at least a portion of said distilland.

The relatively high specific gravity and salt concentration of the aqueous phase formed in b) greatly facilitates the phase separation of c), and enables efficient recovery of amine and recycle of solvent.

Preferably liquid organic makeup solvent, is mixed with the liquid medium during or after the distillation of d) whereby the liquid medium of e) further comprises at least a portion of both distilland and such makeup solvent.

A second embodiment is a process which comprises (a) forming a reaction product composition comprising arylolefin or a substituted arylolefin (e.g., 6-methoxy-2-vinylnaphthalene, 4-isobutylstyrene, or m-vinylbenzophenone, etc.), and amine-hydrohalide in a liquid polar organic solvent medium by palladium-catalyzed arylation of a 1-olefin (e.g., ethylene) with an aryl halide and/or substituted aryl halide (e.g., 2-bromo-6-methoxynaphthalene, 4-bromoisobutylbenzene, m-bromobenzophenone etc.), in a liquid polar organic solvent containing one or more secondary or tertiary amines as hydrogen halide acceptor, and (b) mixing with such reaction product composition a concentrated aqueous solution of inorganic base having a base strength greater than that of the one or more secondary or tertiary amines, to thereby form (i) an organic phase containing such arylolefin or substituted arylolefin, and the one or more secondary or tertiary amines, and (ii) a lower aqueous phase containing dissolved inorganic salt such that said aqueous phase has a specific gravity of at least 1.08 grams per milliliter, when and if measured at 25° C., and (c) separating the phases from each other.

A third embodiment is a process which comprises (A) forming a reaction product composition comprising arylalkylcarboxylic acid or a substituted arylalkylcarboxylic acid (e.g., racemic 2-(6-methoxy-2-naphthyl)propionic acid, 2-(4-isobutylphenyl)propionic acid, or 2-(3-benzoylphenyl) propionic acid, etc.) in a liquid polar organic solvent medium by palladium-catalyzed hydracarbonylation of an arylolefin or substituted arylolefin (e.g., 6-methoxy-2-vinylnaphthalene, 4-isobutylstyrene, or m-vinylbenzophenone, etc.), in a liquid medium comprising polar organic solvent (preferably ketone), water, HCl, and at least one ether (e.g., THF, etc.), (B) mixing with such reaction product composition an aqueous solution of inorganic base (e.g., 25 wt % aqueous NaOH, KOH, etc.), to thereby form a mixture containing an aqueous phase containing dissolved inorganic salt of such arylalkylcarboxylic acid or substituted arylalkylcarboxylic acid, and before, during or after such mixing, distilling at least a substantial portion of the ether from the reaction mixture, such that a mixture of residual organic phase and such aqueous phase remain as a distillation residue (distilland or pot residue), (C) separating the phases from each other, (D) distilling residual organic impurities from the aqueous phase and, if necessary, adjusting the concentration of such aqueous phase to between about 10 and about 35 wt % solution by removal or addition of water, (E) washing the aqueous solution with substantially non-polar liquid organic solvent (preferably a paraffinic hydrocarbon solvent such as hexane or heptane, or an aromatic hydrocarbon solvent such as toluene or xylene), preferably at least twice, (F) mixing non-oxidizing mineral acid (e.g., sulfuric acid) with the aqueous phase in the presence of substantially non-polar liquid solvent to form (i) an organic phase composed of a solution of arylalkylcarboxylic acid or a substituted arylalkylcarboxylic acid in substantially non-polar liquid solvent and (ii) an aqueous phase, (G) separating the phases from each other, and (H) crystallizing arylalkylcarboxylic acid or substituted arylalkylcarboxylic acid from the substantially non-polar liquid solvent.

In accordance with a fourth embodiment of this invention, there is provided a process which comprises:

A) conducting a palladium-catalyzed arylation of an olefin with aryl halide and/or substituted aryl halide in a liquid medium formed from (i) at least one liquid polar organic solvent/diluent, and (ii) at least one secondary or tertiary amine hydrogen halide acceptor capable of forming a water-soluble amine-hydrohalide, to form a reaction mixture comprising olefinically-substituted aromatic compound, amine-hydrohalide and one or more polar organic solvents;

B) contacting (i) at least a portion, and preferably all, of the reaction mixture from A) with (ii) an aqueous mineral acid to form (i) an aqueous phase containing dissolved amine-hydrohalide and, optionally another water-soluble amine salt of said acid, and (ii) an organic phase comprising olefinically-substituted aromatic compound and one or more polar organic solvents;

C) separating the foregoing phases from each other;

D) conducting a palladium-catalyzed carbonylation of at least a portion of said olefinically-substituted aromatic compound with carbon monoxide and water and/or alcohol in a liquid medium comprising one or more liquid polar organic solvent/diluents.

By use of preferred solvent/diluent(s) in A) above a very clean interface can be formed between the aqueous and organic phases formed in B), and the absence of a so-called "rag layer" greatly facilitates the phase separation of C), and enables efficient recovery of amine and recycle of solvent/diluent(s).

Preferably a single organic solvent/diluent is used in A), and more preferably the same single organic solvent/diluent is also present in, or constitutes, the solvent/diluent of D) above.

Before conducting step D) above, steps B) and C) can be repeated in sequence so as to further reduce the amount of amine left in the organic phase.

In a particularly preferred embodiment Steps A), B), C), and D) of the above fourth embodiment are conducted in the same reaction vessel as a so-called "one pot" process. And in this particularly preferred embodiment organic solvent/diluent used in D) above, most preferably is the same organic solvent/diluent used in A) above.

A fifth embodiment is a process which comprises (A) forming in a reactor, a reaction product composition comprising arylolefin or a substituted arylolefin (e.g., 3-vinylbenzophenone, 6-methoxy-2-vinylnaphthalene or 4-isobutylstyrene, etc.), amine-hydro-halide, and optionally free amine in a liquid polar organic solvent medium by palladium-catalyzed arylation of a 1-olefin (e.g., ethylene) with an aryl halide and/or substituted aryl halide (e.g., 3-bromobenzophenone, 2-bromo-6-methoxynaphthalene or 4-bromoisobutyl-benzene, etc.), in a liquid polar organic solvent having a specific gravity less than that of water, and containing at least one secondary or tertiary amine that forms a water-soluble hydrohalide salt (most preferably triethylamine) as hydrogen halide acceptor, and (B) mixing with such reaction product composition an aqueous mineral acid (e.g., dilute aqueous HCl), to thereby form (i) a liquid organic phase containing such arylolefin or substituted arylolefin, and (ii) a lower aqueous phase containing dissolved therein the hydrohalide of said secondary or tertiary amine, and, optionally, another acid salt of the secondary or tertiary amine, and C) draining said lower aqueous phase from the bottom of the vessel to leave said organic phase therein, thereby enabling a subsequent carbonylation reaction to be performed with said arylolefin or substituted arylolefin in the same reactor.

A sixth embodiment of this invention relates to the production of ketoprofen from a benzoyl halide, especially benzoyl chloride. In this embodiment, the following sequence of reactions is conducted either in one plant facility or in two or more separate plant facilities:

1) Benzoyl chloride is brominated to form m-bromobenzoyl chloride, preferably using either bromine or bromine chloride as the brominating agent.

2) m-Bromobenzoyl chloride is reacted with benzene to form m-bromobenzophenone.

3) m-Bromobenzophenone is converted to m-vinylbenzophenone by palladium-catalyzed arylation of ethylene in a liquid polar organic solvent/diluent (preferably having a specific gravity less than that of water), that contains at least a stoichiometric amount of at least one secondary or tertiary amine (most preferably triethylamine) as hydrogen halide acceptor.

4) Reaction product mixture formed in 3) is contacted with aqueous mineral acid (e.g., aqueous HCl), to thereby form (i) a liquid organic phase containing m-vinylbenzophenone, and (ii) a liquid aqueous phase containing dissolved therein the hydrohalide of the secondary or tertiary amine, and, optionally, another water-soluble acid salt of the secondary or tertiary amine.

5) A separation is effected between the aqueous and organic phases formed in 4).

6) m-Vinylbenzophenone from 5), preferably in the same organic phase as in 5), optionally with an additional makeup quantity of the same solvent/diluent, is subjected to a palladium-catalyzed carbonylation with carbon monoxide in the presence of water or alcohol and hydrochloric acid to form 2-(3-benzoylphenyl) propionic acid (if water was used) or an ester of 2-(3-benzoylphenyl)propionic acid (if an alcohol was used).

In a seventh embodiment, a process is provided which comprises:

A) reacting arylolefin or substituted arylolefin with carbon monoxide and water in the presence of palladium catalyst formed at least from (1) palladium or palladium compound and (2) organophosphine ligand, to form a reaction mass comprising (a) arylalkylcarboxylic acid or substituted arylalkylcarboxylic acid, and (b) one or more residual catalyst species;

B) mixing together at least a portion of such reaction mass and aqueous inorganic base to form (i) an aqueous phase with water-soluble salt of the arylalkylcarboxylic acid or substituted arylalkylcarboxylic acid dissolved therein, and (ii) an organic phase having at least a portion of the residual catalyst species dissolved therein;

C) separating these phases, and recycling at least a portion of the separated phase (ii) to A) for use in performing additional reaction pursuant to A).

Oftentimes in B) of this seventh embodiment there is, in addition to phases (i) and (ii), a solids phase containing a portion of the palladium catalyst values. Preferably, such solids phase is recovered (e.g., by filtration) and if not sufficiently catalytically active for recycle, at least a portion thereof is converted into an active palladium catalyst component for use in subsequent reaction pursuant to A) of this embodiment.

An eighth embodiment of the invention is a process which comprises:

A) reacting aryl halide and/or substituted aryl halide with a 1-olefin in the presence of hydrogen halide acceptor and palladium catalyst formed at least from (1) palladium or palladium compound and (2) organophosphine ligand, to form a reaction mass containing arylolefin and/or substituted arylolefin;

B) reacting at least a portion of the arylolefin and/or substituted arylolefin so formed with carbon monoxide and water in the presence of palladium catalyst formed at least from (1) palladium or palladium compound and (2) organophosphine ligand, to form a reaction mass comprising (a) arylalkylcarboxylic acid and/or substituted arylalkylcarboxylic acid, and (b) one or more residual catalyst species;

C) mixing together at least a portion of the reaction mass of B) and aqueous base to form (i) an aqueous phase with water-soluble metal salt of the arylalkylcarboxylic acid and/or substituted arylalkylcarboxylic acid dissolved therein, and (ii) an organic phase having at least a portion of the residual catalyst species dissolved therein;

D) separating these phases, and recycling at least a portion of the separated phase (ii) to A) for use in performing additional reaction pursuant to A) and/or to B) for use in performing additional reaction pursuant to B).

In this eighth embodiment also, there is often present in C) in addition to phases (a) and (b), a solids phase containing a portion of the palladium catalyst values. In such cases it is preferable to recover this solids phase (such as by filtration) and if it is not sufficiently catalytically active for recycle, to convert at least a portion thereof into an active palladium catalyst component for use in subsequent reaction pursuant to A) and/or B) of this embodiment.

It will be seen that in the practice of the seventh and eighth embodiments of this invention the separation between the arylalkylcarboxylic acid or substituted arylalkylcarboxylic acid and the residual catalyst species involves a phase separation (e.g., a phase cut or decantation), and requires no reduced pressure distillation. Moreover, a substantial portion of the catalyst residue is organic-soluble, catalytically active, and highly efficacious when used as catalyst recycle.

Active fresh catalytic species for use in the seventh or eighth embodiments of this invention are preferably formed in situ by the addition to the initial reaction mixture of the foregoing individual components, viz., palladium or palladium compound and organophosphine ligand. However the catalyst can be preformed externally to the reaction mixture and charged to the reactor as a preformed catalyst composition.

A ninth embodiment of this invention is a process which comprises:

a) conducting a palladium-catalyzed arylation of an olefin (most preferably ethylene), with aryl halide and/or substituted aryl halide (preferably 4-isobutyl-1-bromobenzene, m-bromobenzophenone, or 2-bromo-6-methoxynaphthalene), in a liquid medium formed from (i) at least one liquid dialkyl ketone solvent/diluent having 6 carbon atoms in the molecule (most preferably methyl isobutyl ketone), and (ii) at least one secondary or tertiary amine that boils below the boiling temperature of the ketone solvent/diluent (most preferably triethylamine), to form a reaction mixture comprising olefinically-substituted aromatic compound (preferably where the olefinic substituent is a vinyl or substituted vinyl substituent, and most preferably where the compound is 4-isobutylstyrene, m-vinylbenzophenone, or 6-methoxy-2-vinylnaphthalene), amine-hydrohalide and the ketone solvent/diluent;

b) recovering from said reaction mixture a solution composed principally of the olefinically-substituted aromatic compound in the ketone solvent/diluent; and c) conducting a palladium-catalyzed carbonylation of at least a portion of said olefinically-substituted aromatic compound with carbon monoxide and water and/or alcohol in said ketone solvent/diluent to produce arylalkylcarboxylic acid and/or substituted arylalkylcarboxylic acid or, if alcohol was present, arylalkylcarboxylic acid ester and/or substituted arylalkylcarboxylic acid ester.

Preferably the palladium catalyst used in a) of this ninth embodiment is formed from a palladium(II) salt, most preferably palladium(II) chloride or acetate, and a suitable trihydrocarbylphosphine, preferably a cycloalkyldiarylphosphine, and most preferably neomenthyldiphenylphosphine. It appears that a portion of the olefin may also be involved in forming the actual catalytic species in this arylation reaction. Preferably, a small reaction-accelerating amount of water is included or present in the reaction mixture of a) when the reaction is initiated. This amount is typically in the range of about 0.5 to about 5 wt % of the total weight of the entire reaction mixture. When 2-bromo-6-methoxynaphthalene (BMN) used as the initial reactant in the process, the amount of water is preferably in the range of about 1 to about 2 wt % relative to the total weight of the BMN, the ketone solvent/diluent, the amine and the water. In this ninth embodiment the recovery in b) of the solution of olefinically-substituted aromatic compound in methyl isobutyl ketone solvent/diluent preferably involves mixing together at least a portion of the reaction product from a) and an aqueous inorganic base solution of sufficient basicity to liberate the amine, which is distilled from the mixture, and then making a phase cut between the aqueous basic saline phase and the organic phase composed of a solution of the olefinically-substituted aromatic compound in the ketone solvent/diluent. A fresh palladium catalyst is used in c) of this ninth embodiment, and preferably this is formed from a palladium(II) salt, most preferably palladium(II) chloride or acetate, and a suitable trihydrocarbylphosphine, preferably a cycloalkyldiarylphosphine, and most preferably neomenthyldiphenylphosphine. It appears that the actual catalytic species in the carbonylation reaction may involve, in part, interaction between the palladium salt and the olefinically-substituted aromatic compound. Among the advantages made possible by this embodiment when performed in accordance with the preferred modes of operation are higher product yields, higher product purity, faster cycle time, lower raw material cost, and easier process operations.

A tenth embodiment of this invention involves a new way of conducting the carbonylation reaction whereby it is possible to achieve highly desirable results. This new process operation is preferably used in conducting step c) of the ninth embodiment. However this new process operation can be utilized in a variety of carbonylation reactions independently of the process of the ninth embodiment. In particular, the tenth embodiment involves a process which comprises:

a) feeding a solution of olefinically-substituted aromatic compound (preferably where the olefinic substituent is a vinyl or substituted vinyl group, and most preferably where the compound is 4-isobutylstyrene, m-vinylbenzophenone, or 6-methoxy-2-vinylnaphthalene) in a liquid organic solvent/diluent (preferably a liquid ketone solvent, more preferably at least one liquid dialkyl ketone solvent/diluent having 6 carbon atoms in the molecule, and most preferably methyl isobutyl ketone) into a reaction vessel containing a heel formed from ingredients which initially comprised at least aqueous hydrochloric acid, liquid organic solvent/diluent corresponding to the solvent/diluent in the feed, palladium or a palladium compound, a suitable trihydrocarbylphosphine (preferably a cycloalkyldiarylphosphine, and most preferably neomenthyldiphenylphosphine), and optionally an alcohol; and b) heating the contents of the reactor and charging carbon monoxide into the reactor under pressure during at least a portion of the feeding in a) such that carbonylation of the olefinically-substituted aromatic compound occurs to thereby form arylalkylcarboxylic acid or substituted arylalkylcarboxylic acid, or if alcohol is present, to form arylalkylcarboxylic acid ester or substituted arylalkylcarboxylic acid ester.

The solution fed in a) can be a saturated solution, but typically will be a solution containing up to about 40 wt % of the olefinically-substituted aromatic compound, and preferably in the range of about 15 to about 30 wt % of the olefinically-substituted aromatic compound. The feeds of the solution of a) and the carbon monoxide of b) are concurrent for at least a portion of the time the feed of the solution of a) is taking place, and the feed of the carbon monoxide to maintain the selected reaction pressure can continue after completion of the feed of the solution. For best results, the feed of the solution in a) is at a constant continuous rate, and preferably the solution itself is relatively dilute, e.g., a solution containing in the range of about 15 to about 30 wt % of the olefinically-substituted aromatic compound. In this way, the formation of undesired co-products is suppressed. The carbonylation mixture referred to in a) of this tenth embodiment can be a mixture of fresh (i.e., virgin materials) or a heel from a reaction mass from a prior analogous carbonylation reaction or a combination of these. Preferably when a heel is used, a small amount of the olefinically-substituted aromatic compound is charged into the reactor before initiating the feed of the solution in a) and the concurrent feed of pressurized carbon monoxide in b) of this tenth embodiment.

The above and other embodiments will be apparent from the ensuing description and appended claims.

GLOSSARY

In the specification and claims hereof, and unless otherwise specified therein, the following terms have the following meanings:

"alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl, and the like; and "$C_1$ to $C_6$ alkyl" means alkyl with 1 to 6 carbon atoms;

"cycloalkyl" means cyclic alkyl having 3 to 7 carbon atoms and includes cyclopropyl, cyclobutyl, cyclopentyl, cyclohexyl, cycloheptyl and the like.

"substituted cycloalkyl" means cyclopropyl, cyclobutyl, cyclopentyl, cyclohexyl, or cycloheptyl substituted by at least one substituent selected from aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, aryloxy including phenoxy and phenoxy substituted with halo, alkyl, alkoxy and the like, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl and the like;

"aryl" means phenyl, naphthyl, or biphenyl;

"substituted aryl" means phenyl, naphthyl, or biphenyl substituted by at least one substituent selected from aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, aryloxy including phenoxy and phenoxy substituted with halo, alkyl, alkoxy and the like, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl and the like;

"cycloalkylalkyl" means a straight or branched chain alkyl moiety having 1 to 8 carbon atoms that is substituted by a cycloalkyl group having 3 to 7 carbon atoms, and includes, for example, cyclopropylcarbinyl (i.e., carbinyl may also be termed methyl in this context), cyclobutylcarbinyl, cyclopentylcarbinyl, cyclohexylcarbinyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, 6-cyclohexylhexyl and the like;

"aralkyl" means a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like;

"substituted aralkyl" means aralkyl substituted by at least one substituent selected from aroyl (as defined below), halogen (chlorine, bromine, fluorine or iodine), amino, nitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, aryloxy including phenoxy and phenoxy substituted with halo, alkyl, alkoxy and the like, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl and the like;

"substituted benzyl" means benzyl substituted as in substituted aralkyl;

"alkylthio" means a divalent sulfur with alkyl occupying one of the valencies and includes the groups methylthio, ethylthio, propylthio, butylthio, pentylthio, hexylthio, octylthio and the like;

"heteroaryl" means 5 to 10 membered mono- or fused-hetero-aromatic ring which has at least one hetero atom and includes those selected from nitrogen, oxygen and sulfur, and includes, for example, 2-furyl, 3-furyl, 2-thienyl, 3-thienyl, 2-pyridyl, 3-pyridyl, 4-pyridyl, pyrazolyl; imidazolyl, pyrimidinyl, pyridazinyl, pyrazinyl, benzimidazolyl, quinolyl, oxazolyl, thiazolyl, indolyl and the like;

"substituted heteroaryl" means 5 to 10 membered mono- or fused-heteroaromatic ring which has in the ring at least one hetero atom selected from nitrogen, oxygen and sulfur, and which ring is substituted by at least one substituent selected from halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl and the like;

"aroyl" means benzoyl or naphthoyl;

"substituted aroyl" means benzoyl or naphthoyl substituted by at least one substituent including those selected from halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused- heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, benzimidazolyl-carbonyl and the like;

"substituted heteroarylcarbonyl" means the above-mentioned heteroarylcarbonyl which is substituted by at least one substituent selected from halogen, amino, nitro, hydroxy, alkoxy and haloalkyl on the heteroaryl nucleus; and includes, for example, 2-oxo-1,3-dioxolan-4-ylmethyl, 2-oxo-1,3-dioxan-5-yl and the like;

"vinyl" means an unsaturated substituent having at least one unsaturated double bond and having the formula $CH_2=CH-$;

"substituted vinyl" means the above vinyl substituent having at least one of the protons on the terminal carbon atom replaced with alkyl, cycloalkyl, cycloalkylalkyl, aryl, substituted aryl, heteroaryl or substituted heteroaryl;

"hydrocarbyl" means a univalent hydrocarbon group containing up to about 24 carbon atoms (i.e., a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, aralkyl, alkyl-substituted aralkyl, and cycloalkyl-substituted aralkyl;

"functionally-substituted hydrocarbyl groups" means a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl;

"substituted aryl halide" means an aryl halide in which the aryl group is a substituted aryl group where the substitution includes in addition to a halide atom, at least one other substituent included in the above definition of substituted aryl;

"substituted arylolefin" means the product formed by a palladium-catalyzed reaction of a substituted aryl halide and an olefin as described herein;

"arylalkylcarboxylic acid" means the product formed by palladium-catalyzed reaction of an arylolefin and carbon monoxide and water as described herein;

"substituted arylalkylcarboxylic acid" means the product formed by palladium-catalyzed reaction of a substituted arylolefin (i.e. an olefin which contains a "substituted aryl" as defined above) and carbon monoxide and water as described herein;

"arylation" means a reaction in which at least one aryl halide, or at least one substituted aryl halide or a combination of at least one aryl halide and at least one substituted aryl halide is used as a reactant in the reaction with at least one olefinic compound.

"liquid" means that the material referred to exists in the liquid state of aggregation at 20° C. (and preferably at temperatures below 20° C.).

This invention involves, inter alia, reactions in which a vinylaromatic or substituted vinylaromatic compound is reacted with carbon monoxide and either water or an alcohol to form an arylalkylcarboxylic acid or substituted arylalkylcarboxylic acid or, if an alcohol is used, an arylalkylcarboxylic acid ester or substituted arylalkylcarboxylic acid ester. There appears to be a lack of unanimity as regards the terminology to be used in referring to such reactions. On the one hand, since a carboxyl group or ester moiety is being formed, there is precedent and logic for referring to the reaction as a "carboxylation". On the other hand, reactions involving catalyzed addition of carbon monoxide to substrate molecules even in the presence of water have been referred to as "carbonylation" or "hydracarbonylation" reactions. Since the latter type of nomenclature appears to predominate in the literature, the latter type of terminology is adopted herein. Thus, as used in this specification and the claims hereof, unless the context otherwise requires, "carbonylation" is used to refer to the reaction generically, i.e., irrespective of whether water or alcohol is the co-reactant. Similarly, the term "hydracarbonylation" is used to signify that the reaction uses water as the co-reactant. To denote that the co-reactant is an alcohol, the term "alkoxacarbonylation" is used.

FURTHER DETAILED DESCRIPTION—FIRST, SECOND AND THIRD EMBODIMENTS

Arylation Reaction

Palladium-catalyzed arylations of olefins with aryl halides are well known and reported in the literature. See for example, C. B. Ziegler, Jr., and R. F. Heck, *J. Org. Chem.*, 1978, 43, 2941 and references cited therein, and U.S. Pat. No. 5,536,870 to T-C Wu. Both of the foregoing documents are incorporated herein by reference as if fully set forth herein. In the practice of this invention the arylation reaction is used for preparing an olefinic compound of the formula

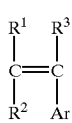 (I)

where Ar is aryl, substituted aryl, heteroaryl, substituted heteroaryl, aralkyl (especially benzyl), or substituted aralkyl (especially substituted benzyl), and $R^1$, $R^2$, and $R^3$ are the same or different and are selected from hydrogen atoms, hydrocarbyl groups, functionally-substituted hydrocarbyl groups, and halogen atoms. This is accomplished by reacting at least one aryl halide and/or substituted aryl halide of the formula

 (II)

where Ar is as defined above and X is a halogen atom of atomic number greater than 9, a diazonium group or triflate or other leaving group; with at least one olefinic compound of the formula

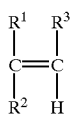 (III)

where $R^1$, $R^2$, and $R^3$ are as previously defined. The substituted aryl group of the substituted aryl halide is preferably phenyl substituted with alkyl, naphthyl substituted with alkoxy, phenyl substituted with aryloxy or substituted aryloxy (especially phenoxy), aryl substituted with fluoro, or phenyl substituted with aroyl, and the halogen atom of the substituted aryl halide is preferably a bromine atom. Examples of substituted aryl halides include compounds wherein the substituted aryl group is an isobutylphenyl group, a methoxynaphthyl group, a phenoxyphenyl group, a fluorobiphenylyl group, a benzoylphenyl group, and where the halogen atom is a chlorine, an iodine, or most preferably, a bromine atom.

The preferred olefinic compounds of Formula (III) are those in which $R^1$, $R^2$, and $R^3$ are hydrogen atoms, $C_1$ to $C_6$ alkyl, substituted or unsubstituted phenyl, and/or trifluoromethyl. Examples include compounds of Formula (III) wherein $R^1$, $R^2$, and $R^3$ are hydrogen atoms, methyl, and/or trifluoromethyl. Olefins in which $R^3$ is a hydrogen atom are more preferred, and vinyl olefins in which $R^1$ is a hydrogen atom or a $C_1$ to $C_6$ alkyl group, and $R^2$ and $R^3$ are hydrogen atoms especially preferred. Ethylene is the most preferred olefinic reactant.

The reaction is conducted in a liquid medium formed from (i) one or more liquid polar organic solvent/diluents, and (ii) one or more secondary or tertiary amines that (1) boil(s) below the boiling temperature of the solvent/diluent if only one solvent/diluent is used in forming the medium or (2) that boil(s) below the boiling temperature of at least one, but not necessarily all, of the polar solvent/diluents used in forming the medium if more than one solvent/diluent is used in forming the medium. The solvent/diluent should have at least a measurable polarity at a temperature in the range of 20 to 25° C., and yet be free of functionality that would prevent or materially impair, inhibit or otherwise materially interfere with the arylation reaction. Examples include tetrahydrofuran, 1,4-dioxane, diglyme, triglyme, acetonitrile, propionitrile, benzonitrile, N,N-dimethylformamide, N,N-dimethylacetamide, dimethylsulfoxide, nitrobenzene, sulfolane, acetone, butanone and cyclohexanone. Preferred solvent/diluents are one or more aprotic solvents each having a dielectric constant of at least about 10 (especially 10 to 30) at a temperature in the range of 20 to 25° C. From the cost-effectiveness standpoint, hydrocarbyl ketones with 4 or more carbon atoms in the molecule (e.g., 4 to about 8) are especially preferable. Examples include diethyl ketone, methyl isobutyl ketone, 2-pentanone, 2-hexanone, 2-heptanone, 3-heptanone, 4-heptanone, and like liquid ketones, as well as mixtures of two or more such ketones. Most preferred is diethyl ketone (3-pentanone). The arylation reaction inherently tends to be an exothermic reaction, and the use of diluents having a dielectric constant in the range of about 10 to about 30 (as measured at 20 to 25° C.), such as a ketone meeting this qualification provides a readily controllable reaction.

The secondary or tertiary amines are used as hydrogen halide acceptors and thus preferably are used in at least a stoichiometric amount relative to the aryl halide and/or substituted aryl halide being used. However it is possible, though less desirable, to use less than a stoichiometric amount of amine, by allowing the reaction with less than a stoichiometric amount of amine to proceed only part way, and by recycling the reaction mixture for further reaction in the presence of additional amine added thereto.

Use can be made of any liquid secondary or tertiary amine that is free of functionality that would prevent or materially impair, inhibit or otherwise materially interfere with the arylation reaction, that boils below the boiling temperature of the polar solvent/diluent used when only one is used in forming the liquid medium for the reaction, or that boils below at least one of a plurality of polar solvent/diluents used in at least a substantial amount (e.g., at least 20 or 30% of the total volume of the solvent/diluents), when more than one is used in forming the liquid medium for the reaction, and that has sufficient basicity to serve as a hydrogen halide acceptor for the HCl, HBr and/or HI, formed in the arylation reaction. Preferred are liquid tertiary amines. The amines may be polyamines such as for example, N,N,N',N'-tetramethylethylenediamine (b.p. ca. 120–122° C.), but in most cases monoamines are preferable. Among useful liquid amines having suitably low boiling points are diethylamine (bp 55° C.), N,N-dimethylethylamine (bp 36–38° C.), N,N-diethylmethylamine (bp 63–65° C.), diisopropylamine (bp 84° C.), triethylamine (bp ca. 89° C.), dipropylamine (bp ca. 105–110° C.), and di-sec-butylamine (bp ca. 135° C.). Triethylamine is a particularly preferred amine.

Liquid media formed from diethyl ketone and acetonitrile (e.g. in a weight ratio in the range of 1:9 to 4:1, and more preferably in the range of 1:3 to 3:1) plus triethylamine, or from diethyl ketone and N,N-dimethylformamide (e.g., in a weight ratio in the range of 1:9 to 9:1) plus triethylamine are typical desirable liquid media for use in this invention.

Liquid media formed from diethyl ketone and triethylamine or from methyl isobutyl ketone and triethylamine are particularly preferred.

In the practice of this invention, the reaction is typically conducted in the presence of a catalytically effective amount of a catalyst system formed from (a) palladium and/or at least one compound of palladium in which the palladium has a valence of zero, 1 or 2, and (b) a tertiary phosphine ligand of the formula $$R^4R^5R^6P \quad\quad (IV)$$

where $R^4$, $R^5$, and $R^6$ are the same or different and are selected from alkyl, aryl, substituted aryl, heteroaryl, substituted heteroaryl, aralkyl, substituted aralkyl, cycloalkyl, and substituted cycloalkyl, at least one of $R^4$, $R^5$, and $R^6$ being aryl or substituted aryl. Preferably at least one of $R^4$, $R^5$, and $R^6$ is aryl or substituted aryl and at least one of $R^4$, $R^5$, and $R^6$ is cycloalkyl or substituted cycloalkyl.

The use of salts of palladium in forming the catalysts is preferable because catalyst compositions formed from palladium salts appear to have greater activity than those made from palladium metal itself. Of the salts, palladium(II) salts such as the Pd(II) halides (chloride, bromide, iodide) and Pd(II) carboxylates (e.g., acetate, propionate, etc.) are most preferred.

A highly preferred type of tertiary phosphine (sometimes referred to herein as "ligand") used is one or more tertiary phosphine ligands of the formula

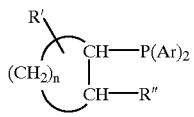

where R' and R" are the same or different and are individually hydrogen, alkyl, aryl or substituted aryl, Ar is phenyl, naphthyl, substituted phenyl or substituted naphthyl and n is an integer from 3 to 6. Preferably, R' and R" are the same or different and are $C_1$ to $C_6$ alkyl, Ar is phenyl or naphthyl and n is 3 or 4. Most preferably, R' is methyl or ethyl, R" is $C_3$ to $C_6$ branched alkyl, Ar is phenyl and n is 4. Especially preferred as the phosphine ligand is neomenthyldiphenylphosphine.

Active catalytic species are preferably formed in situ by the addition to the reaction mixture of the foregoing individual components. However the catalyst can be preformed externally to the reaction mixture and charged to the reactor as a preformed catalyst composition.

Desirably, a small reaction-accelerating amount of water is included or present in the reaction mixture, as described in commonly-owned U.S. application Ser. No. 08/780,310, filed Jan. 8, 1997, pending all disclosure of which is incorporated herein. This amount is typically in the range of about 0.5 to about 5 wt % of the total weight of the entire reaction mixture. Within the range of about 0.5 to 5 weight percent water there is often an optimum amount of water which gives the highest or peak reaction rate which falls off if more or less water is used. This optimum amount of water may vary depending upon the identity and proportions of the ingredients used in forming the reaction mixture. Thus in any given situation it may be desirable to perform a few preliminary experiments with the particular reaction to be conducted, wherein the amount of water is varied within the range of about 0.5 to about 5 wt % to locate the optimum rate-enhancing amount of water in the mixture. Preferably, the amount of water used will be insufficient to form a second liquid phase (i.e., a separate water layer) in a mixture consisting of (i) the amount of the liquid organic solvent/diluent(s) selected for use, (ii) the selected amount of the liquid secondary and/or tertiary amine(s) selected for use, and (iii) the selected amount of water, when such mixture is agitated for 10 minutes at 25° C. and allowed to stand for 15 minutes at the same temperature. Thus when conducting the process on a large scale with recycle of solvent(s) and amine, the amount of water carried over from product workup should be monitored and/or controlled such that the water content of the reaction mixture remains at or below about 5 wt % of the total weight thereof. Conversely if the amount of recycled water is insufficient to maintain the desired water content in the reaction mixture, additional water should be added to bring the water content up to the desired amount within the foregoing range. Preferably the arylation reaction mixtures have a water content in the range of about 1 to about 3.5 weight percent.

In conducting an operation wherein a mixture of (i) liquid organic solvent/diluent(s), (ii) secondary and/or tertiary amine(s), and (iii) water that does not separate into a two-phase system is used, the liquid mixture of these components may nonetheless be hazy or cloudy, but a distinct coalesced second liquid phase does not and should not exist as a separate layer in such liquid mixture.

The arylation reaction is performed under conditions such that olefinic compound of Formula (I) above is formed. Such conditions usually require an equimolar ratio of olefinic compound (Formula (III) above) to aryl halide and/or substituted aryl halide (Formula (II) above), although an excess of olefinic compound is preferred. The palladium catalyst and the phosphine ligand are typically used at about a ratio of 1 mole of organic halide to 0.0005 mole of palladium or palladium compound. The ligand is present in the same or higher molar proportion as the palladium or palladium compound. It should be noted that levels of (a) palladium or palladium compound, and (b) ligand can be substantially higher (up to 10 times). When relatively inactive species of olefinic compound or aryl halide and/or substituted aryl halide are employed, for example, highly substituted olefins and/or substituted aryl halides bearing strongly electron donating substituents, these higher amounts of catalyst and ligand may be required. Thus the mole ratio of aryl halide and/or substituted aryl halide:Pd:ligand used will generally be a suitable ratio within the range of 200–20,000:1:1–20, respectively.

Temperatures of reaction are quite modest, varying from about 25° C. to 200° C. (preferably 60° C. to 150° C.) with pressures (for the gaseous vinyl compounds) being from atmospheric up to about 3000 psi (preferably 300 to 1000 psi). With the preferred catalyst systems and liquid media referred to above, reaction times are unusually short, typically giving complete reaction in the range of 1 to 24 hours, typically in the range of about 2 to about 6 hours. Higher temperatures and lower pressures tend to cause increased by-product formation.

The preferred and the optimum conditions will depend to some extent upon the identity of the particular ingredients being used. Thus, for example, when forming 6-methoxy-2-vinylnaphthalene (MVN) from 2-bromo-6-methoxynaphthalene (BMN) using ethylene as the olefinic reactant, a palladium (II) salt such as $PdCl_2$ and neomenthyldiphenylphosphine (NMDP) as catalyst or catalyst precursors, a $C_4$–$C_8$ ketone especially diethyl ketone and a $C_4$–$C_9$ trialkyl amine especially triethylamine as the liquid medium and a reaction accelerating amount of water, the BMN:Pd:NMDP mole ratio is preferably in the range of about 1000–3000:1:2–10, respectively, the mole ratio of amine:BMN can be in the range of 0.1–2:1 and preferably is in the range of 1–2:1 respectively, the mole ratio of ketone:amine is preferably in the range of 1.0–4.0:1 respectively, the weight of water based on the total weight of BMN+ ketone+amine+Pd catalyst ingredient+tertiary phosphine ligand+water is preferably in the range about 1 to about 3.5 wt %, the reaction temperature is typically in the range of about 60 to about 150° C. and preferably in the range of about 80 to about 110° C., and the pressure of the ethylene used is preferably in the range of about 400 to about 1000 psig. Under these conditions, reaction is complete within about 1 to about 24 hours, and oftentimes within about 2 to about 6 hours, with conversions and yields of MVN (both based on BMN used) of 70% to 99%, such as, for example, about 95% conversion and about 85% yield. It is to be clearly understood that the foregoing conditions given in this paragraph are, as stated, preferred conditions for carrying out the specified reaction. On the basis of the information presented in this disclosure, one skilled in the art could readily operate outside of the ranges given in this paragraph, and still achieve good performance in accordance with this invention. Thus this invention is not limited to use of the conditions given in this paragraph, and it is within the scope of this invention when performing the specified reaction to depart from any one or more of such ranges, whenever deemed necessary or desirable in any given situation.

For best results, the overall arylation reaction mixture is essentially solids-free when at reaction temperatures, except for some precipitation of palladium and formation of some solid co-products such as amine-hydrohalide salt and products formed by interaction of the aryl halide and/or substituted aryl halide (e.g., BMN) with the vinylated product (e.g., MVN), and/or by dimerization of such vinylated product that may occur as the reaction proceeds. Since the reaction tends to be exothermic, it is desirable to utilize reactors equipped with internal cooling coils, cooling jackets or other highly effective cooling means to ensure suitable temperature control.

A few examples of desirable laboratory reaction parameters in the reaction of BMN with ethylene using $PdCl_2$ and NMDP at 95° C. and 420 psig ethylene are as follows:

a) NMDP:Pd mole ratios in the 5–6:1 range give relatively fast reaction rates.

b) BMN:Pd:NMDP mole ratios of 2000:1:6, 2500:1:5 and 3000:1:10 give high conversions and good yields; ratios of 3000:1:6 and 3500:1:5 are operable but give lower conversions.

c) As agitator speeds increase from 300 to 1500 rpm, reaction times to completion decrease by almost two hours.

d) At a BMN:Pd:NMDP mole ratio of 2000:1:6, ethylene pressures ranging from 190 psig to 955 psig at 95° C. give good results. Thus at 190 psig the yield of MVN was 86%, and at 900 psig the yield was 96%. At the higher pressures of the range, reaction times were shorter and the amount of solid by-products formed was less.

e) At a BMN:Pd:NMDP mole ratio of 2000:1:6, MVN yields are higher and the amount of solid by-products formed is lower, when using BMN concentrations at the lower end of the range of 20 to 35 wt % than at the higher end of the range.

f) Reactions at a BMN:Pd:NMDP mole ratio of 2000:1:6 using 1.6 wt % water as reaction accelerator proceed at a higher reaction rate at 95° C. than at 85° C.

g) Maximum rate of reaction is achieved at about 3 wt % water when operating at 95° C., 420 psig ethylene, BMN:Pd:NMDP mole ratio of 2000:1:6, at 30 wt % BMN concentration. The rate is about 150% of the rate when no added water is present. Under these particular conditions, water levels greater than about 4% caused the reaction to stop at less than complete conversion.

h) Use of recycled DEK solvent in four successive runs was successful; no new impurities were found in the MVN product solutions after four recycles. Addition of makeup water when needed to maintain the desired level of water in the reaction mixture is desirable in order to achieve the beneficial reaction accelerating effect of the water from run to run.

Therefore, in producing 6-methoxy-2-vinylnaphthalene (MVN) from 2-bromo-6-methoxynaphthalene (BMN) by reaction with ethylene, using a palladium (II) salt such as $PdCl_2$ and neomenthyldiphenylphosphine (NMDP) as catalyst or catalyst precursors, the preferred reaction medium is a mixture comprising a $C_4$–$C_8$ ketone (especially diethyl ketone) and a $C_4$–$C_9$ trialkyl amine (especially triethylamine). This reaction medium preferably contains a reaction accelerating amount of water in the range of about 1 to about 3.5 weight percent of the total weight of the reaction mixture. The BMN:Pd:NMDP mole ratio is preferably in the range of about 1000–3000:1:2–10, respectively, (e.g., a BMN:Pd:NMDP mole ratio of 2000:1:6), the mole ratio of amine:BMN is preferably in the range of 1–2:1 respectively, the mole ratio of ketone:amine is preferably in the range of 1.0–4.0:1 respectively, the reaction temperature is preferably in the range of about 80 to about 110° C. (e.g., about 95° C.), and the pressure of the ethylene used is preferably in the range of about 400 to about 1000 psig (e.g., about 420 psig).

Workup of Arylation Product

The arylation reaction produces a reaction mixture comprising olefinically-substituted aromatic compound, amine-hydrohalide and one or more of the polar organic solvents. Pursuant to one of the preferred embodiments of this invention, a concentrated aqueous solution of inorganic base such as $K_2CO_3$, $NaHCO_3$, etc., having a base strength greater than that of the amine(s) of the amine hydrohalide, and more preferably a concentrated aqueous alkali metal hydroxide solution, is mixed with at least a portion (preferably, all) of the reaction mixture to convert the amine-hydrohalide therein to free amine and inorganic halide salt such as alkali metal halide, and to form (I) an aqueous phase containing dissolved halide salt, and (ii) an organic phase comprising olefinically-substituted aromatic compound, amine, and one or more of the polar organic solvents. Although well known to those skilled in the art, it is deemed necessary, or at least prudent, to point out that because the conversion of the amine-hydrohalide to free amine and, say, "alkali metal halide" is conducted in the presence of water, the "alkali metal halide", or at least a substantial proportion thereof, exists in ionic form while dissolved in the water. Thus according to known chemical principles, the water contains alkali metal cations and halide anions. However chemists would commonly refer to this as forming alkali metal halide because upon removal of water, alkali metal halide would indeed exist as such. Thus when referring in the specification and claims hereof to converting the amine-hydrohalide to free amine and halide salt such as alkali metal halide, it is to be understood that this means that the resulting mixture contains the liberated amine and the halide salt in whatever chemical forms they exist in the environment and under the conditions used.

The concentrated alkali metal hydroxide solution may be formed by dissolving alkali metal oxide or hydroxide, or both, in water. The preferred alkali metal oxides and/or hydroxides are those of sodium or potassium, or mixtures thereof. These are plentiful and less expensive than the lithium, rubidium and cesium oxides and hydroxides, which could, however, be used. If desired, the sodium hydroxide or potassium hydroxide solution may be formed from small or even trace amounts of one or more of these other more expensive alkali metal oxides and/or hydroxides together with large amounts of the sodium and/or potassium oxides and/or hydroxides. Again it is to be noted that in the aqueous solution, the alkali metal hydroxide is ionized so that the solution contains, according to well established chemical principles, alkali metal cations and hydroxyl anions. Therefore, reference in the specification and claims hereof to alkali metal hydroxide solution means that the alkali metal hydroxide is in whatever chemical form it exists while in a concentrated aqueous solution.

Whether conducted in stages or all at once, ultimately at least a stoichiometric amount of the inorganic base should be, and in most cases is, employed relative to the amount of amine-hydrohalide present in the reaction mixture.

As to the concentration of these inorganic base solutions, it is desirable to use solutions that contain the equivalent of at least about 10 weight percent of the base, such as alkali metal hydroxide, being used. Saturated aqueous alkali metal hydroxide solutions can be used, but typically the concentration will be at least slightly less than this. Preferred aqueous solutions contain the equivalent of about 20 to about 50 wt % of sodium hydroxide or of potassium hydroxide, or of both. Particularly preferred aqueous solutions contain the equivalent of about 23 to about 27 wt % of sodium hydroxide and/or potassium hydroxide. Most preferred is 25 wt % sodium hydroxide aqueous solution.

Preferably the aqueous solution of inorganic base such as alkali metal hydroxide is used in an amount that produces an alkali metal halide solution containing the equivalent of at least about 30 wt % of sodium bromide, and more preferably the equivalent of at least about 33 to 50 wt % of sodium bromide, as this makes the ensuing phase separation easier if the aqueous phase has the higher densities of such concentrated solutions. In addition, less of the organic solvent/diluent(s) and amine(s) are soluble in the aqueous phases having such higher metal halide concentrations, and thus solvent losses are thereby reduced.

The conditions for the mixing of the inorganic base solution such as alkali metal hydroxide solution with the arylation reaction mixture are not critical. All that is required is to ensure that these materials are sufficiently well mixed so that intimate contact is established between these materials. Temperatures will typically be in the range of about 40 to about 70° C., but other temperatures may be used. Agitation periods in the range of about 5 to about 15 minutes will normally suffice, but longer periods of up to 30 minutes or more (e.g., one hour or more) can be used, if desired.

After mixing, the resulting mixture is allowed or caused to separate into the organic and aqueous phases, usually by allowing the mixture to stand in a quiescent state. Standing periods of one hour or less are usually sufficient. In fact, when treating an arylation reaction mixture with sufficiently concentrated sodium hydroxide solution to produce an aqueous phase containing 40–45 wt % of sodium bromide, the phases separate quickly, e.g., in as little as 15 minutes. Moreover the phase interface is distinct and easy to detect since oligomeric coproducts tend to float on top of such a concentrated aqueous phase. Then the phases are separated from each other, for example by decantation or, more usually, by draining off the lower aqueous layer.

Next, substantially all of the amine is distilled from the remainder of the organic phase under low temperature and pressure conditions that suppress thermal oligomerization of the olefinically-substituted aromatic compound contained in the residual liquid phase. This distillation can be performed at any suitable reduced pressure such as, for example, in the range of about 50 to about 600 mm Hg, and preferably at pressures in the range of about 200 to about 350 mm Hg. Residual amine if present in excessive amounts in the remainder of the organic phase after distillation can have adverse effects upon the ensuing carbonylation reaction. For example, excessive amounts of such residual amine can cause the carbonylation reaction to stop prematurely with consequent loss of conversions and yields. The amount of such residual amine that can be tolerated in the remainder of the organic phase after distillation may vary depending upon such factors as the makeup of the organic phase, the identity of olefinically-substituted aromatic compound contained therein, and the conditions to be used in the carbonylation reaction. Thus in any given situation it may be desirable to perform a few preliminary experiments to determine the amount of amine that can be tolerated without significant adverse effects. Thus sufficient amine is removed such that residual amine, if any, remaining in the remainder of the organic phase does not cause (a) more than about a 5% reduction in conversion of olefinically-substituted aromatic compound contained in the remainder of such organic phase, and (b) more than about a 5% loss of yield of carbonylated product in the ensuing carbonylation as compared to an identical carbonylation of another portion of the same original organic phase from which the amine has been rigorously removed to the extent possible without significantly reducing the olefinically-substituted aromatic compound content of the organic phase. Preferably the amount of residual amine, if any, remaining in the remainder of the organic phase is sufficiently small so that (a) no more than about a 1% reduction in conversion of olefinically-substituted aromatic compound contained in the remainder of such organic phase, and (b) no more than about a 1% loss of yield of carbonylated product in the ensuing carbonylation will occur as compared to an identical carbonylation of another portion of the same original organic phase from which the amine has been rigorously removed to the extent possible without significantly reducing the olefinically-substituted aromatic compound content of the organic phase. To ensure no material adverse effects of amine on the carbonylation reaction, residual amounts of amine are preferably maintained below about one (1) percent by weight of the distilland remaining after the distillation of amine therefrom.

Preferably, liquid organic makeup solvent is mixed with the liquid mixture during or after the distillation of the amine whereby the liquid mixture for carbonylation further comprises at least a portion (preferably, all) of the distilland and the makeup solvent. While various solvents may be used, the makeup solvent preferably comprises at least one ether, preferably a liquid cyclic monoether such as tetrahydrofuran, methyltetrahydrofuran, tetrahydropyran, or etc., or a cyclic diether such as 1,3-dioxolane, 1,4-dioxane, or etc., or a mixture of such materials with or without one or more acyclic ethers such as diethyl ether, methyl tert-butyl ether, or the like. The most preferred makeup solvent is tetrahydrofuran as this material appears to exert a rate enhancing effect upon the carbonylation reaction. It is expected that at least some alkyl-substituted tetrahydrofurans may also behave in this manner.

When a mixture of acetonitrile and a liquid ketone having a boiling point above the amine, such as diethyl ketone and/or methyl isobutyl ketone, is used as the solvent or diluent in the arylation reaction, minor variants in the workup procedure are preferably employed. In one such procedure, (1) the acetonitrile is distilled from the arylation reaction mixture, (2) the concentrated aqueous solution of inorganic base is mixed with the residual reaction product to form the aqueous and organic phases (as above), (3) the phases are separated, and (4) the amine is distilled from the organic phase. Then makeup solvent (e.g., tetrahydrofuran) is added to the organic phase, and the resultant organic phase is then utilized in the carbonylation reaction described more fully hereinafter. Another such procedure involves (1) mixing the concentrated aqueous solution of inorganic base with the arylation reaction mixture, (2) separating the phases, and (3) distilling the acetonitrile and the amine from the separated organic phase. Then the makeup solvent is added to the organic phase, and the resultant organic phase is then utilized in the carbonylation reaction.

Another process for effecting workup of the arylation reaction product involves using a dilute aqueous washing procedure. In this embodiment the procedure comprises mixing with at least a portion of the arylation reaction product composition a dilute aqueous acid to thereby form (i) an organic phase containing the arylolefin or substituted arylolefin, and (ii) an acidic aqueous phase containing dissolved amine hydrohalide, and separating at least a portion of these phases from each other. The dilute aqueous acid is preferably dilute aqueous hydrochloric acid, e.g., in the range of about 1 to about 20 wt % aqueous HCl. The amount used should be sufficient to form an acidic aqueous phase containing substantially all of the amine-hydrohalide, which can readily be separated from the organic phase comprising the polar solvent(s) and the arylolefin or substituted arylolefin. At least a portion of the separated organic phase is then suitable as feed to a palladium-catalyzed carbonylation to form arylalkylcarboxylic acid or ester or substituted arylalkylcarboxylic acid or ester in accordance with conditions and procedures described hereinafter. Before conducting the carbonylation reaction, an ethereal solvent such as a cyclic ether solvent (tetrahydrofuran, methyltetrahydrofuran, 1,4-dioxane, etc.), can be added to the separated organic phase to enhance the ensuing carbonylation reaction. To accommodate the added ethereal solvent, the separated organic phase may be subjected to a stripping or distillation step to remove some of the polar solvent(s) from the separated organic phase, before adding the ethereal solvent. The stripped polar solvent may be used as recycle solvent in the arylation process.

It is also desirable to recover the secondary and/or tertiary amine from the separated aqueous phase. This is accomplished by mixing together at least a portion of the separated aqueous phase and a strong inorganic base to form free amine and an aqueous solution of inorganic halide. Suitable strong bases include NaOH, KOH, NH$_4$OH, Na$_2$O, K$_2$O, Ca(OH)$_2$, Na$_2$CO$_3$, K$_2$CO$_3$, CaO, and other inorganic bases of comparable base strength. This results in the formation of an aqueous phase and an organic phase consisting essentially of the free amine(s). Separation of these phases provides the amine for use as recycle. The amine can be purified by distillation, if necessary.

Carbonylation

In this operation the olefinically-substituted aromatic compound is converted into a compound of the formula

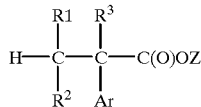

where Ar, R$^1$, R$^2$, and R$^3$ are as previously defined, and Z is a hydrogen atom, an alkali metal atom (preferably Na or K), a hydrocarbyl group (preferably C$_1$–C$_6$ alkyl), or a functionally-substituted hydrocarbyl group. The procedures and conditions for effecting the carbonylation leading to the formation of compounds of Formula (V) are described below. By suitable modifications of or additions to such procedures, compounds of Formula (V) can be produced in which Z can be any of a wide variety of other groups, non-limiting exemplifications of which include ammonium, quaternary ammonium, one-half equivalent of a divalent metal atom, one-third equivalent of a trivalent metal cation, and so on.

The catalytic carbonylation of the compound of Formula (I) is effected with carbon monoxide and water and/or alcohol, and is conducted, at a temperature between about 25° C. and about 200° C., preferably about 25°–120° C., and most preferably about 25°–100° C. Higher temperatures can also be used. The best yields are obtained when the temperature is maintained at a relatively low level throughout the reaction.

The partial pressure of carbon monoxide in the reaction vessel is at least about 1 atmosphere (0 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from 0 to about 3000 psig at the reaction temperature and most preferred is a pressure from 0 to about 1000 psig. It should be noted that the presence of oxygen is undesirable in the hydracarbonylation reaction of this invention. Hence, an atmosphere of 100% carbon monoxide is most preferred to carry out this process. Various inert gases can, however, be incorporated in the reaction mass (nitrogen, argon, etc.), the only criterion being that the process should not be slowed to the point of requiring exceptionally long periods to complete the reaction.

As noted above, the carbonylation is conducted in the presence of an appropriate amount of water or aliphatic alcohol. Strictly speaking, when the reaction is conducted in the presence of water it is a hydracarbonylation reaction, and when conducted in the presence of an alcohol it can be termed a alkoxacarbonylation reaction. Consequently, unless otherwise qualified or specified, the term "carbonylation" is used herein in a generic sense to denote both hydracarbonylation (using water) and alkoxacarbonylation (using an alcohol).

In the case of hydracarbonylation of MVN, at least about one (1) mole of water per mole of the MVN should be used, and about four moles of water per mole of the MVN is typically employed. It is worth noting that an excessive amount of water can inhibit or even kill the reaction. The effect of large excesses of alcohols in the alkoxacarbonylation of MVN has not been studied in detail, but it would appear prudent to avoid use of excessive amounts. Thus amounts in the range of up to about 10 wt % in the reaction mixture are suggested. In carbonylation reactions with other compounds of Formula (I), an excess amount of water and/or alcohol may sometimes be used. In such cases, although possibly there may be no real upper limit to the amount of water or alcohol except that imposed by practicality (e.g. the size of the reaction vessel, and the kinetics of the reaction), an amount up to about 100 moles, and preferably up to about 50, moles per mole of the compounds of Formula (I) may be considered for use in the process, and an amount from about 2 to about 24 moles of water or alcohol per mole of the such olefinic compound is more preferred. The product of the reaction is a carboxylic acid (where Z in Formula (V) is a hydrogen atom) or carboxylic acid ester (where Z in Formula (V) is alkyl or substituted alkyl).

The present invention embraces the formation of any racemates and individual optical isomers of the compounds of Formula (V) having a chiral carbon atom. For example, when compounds of Formula (V) wherein the acid is 2-(6-methoxy-2-naphthyl)propionic acid, are subjected to resolution as taught in U.S. Pat. No. 4,246,164 (incorporated herein by reference), the analgesic compound naproxen is produced.

If desired, any alcohol which produces an ester of the carboxylic acid may be used in the practice of this invention. In a preferred embodiment, the $C_1$ to $C_6$ aliphatic alcohols are used. Examples of the alcohols to be used in this embodiment include methyl alcohol, ethyl alcohol, n-propyl alcohol, isopropyl alcohol, n-, iso-, sec-, and tert-butyl alcohols, the pentyl alcohols, (isoamyl alcohol, especially to form the (±)-2-(6-methoxy-2-naphthyl)propionic acid ester), the hexyl alcohols, etc. Methyl alcohol is highly preferred, and ethyl alcohol is most highly preferred. Other alcohols, glycols, or aromatic hydroxy compounds may also be used. In the broadest sense, these alcohols provide a source of alkoxide ions for this reaction. However, any other "source of alkoxide ions" may also be used. The source of such alkoxide ions is from a compound selected from the group consisting of $HC(OR_1)_3$, $(R)_2C(OR_1)_2$, $HC(O)OR_1$, $B(OR_1)_3$, $Ti(OR_1)_4$ and $Al(OR_1)_3$ where R is hydrogen or individually the same as or different from $R_1$, and $R_1$ is alkyl or substituted alkyl.

In some cases, the carbonylation reaction is initiated under neutral conditions, i.e., with no added acid. However, at least in the case of hydracarbonylation of MVN, the inclusion of aqueous HCl in the reaction mixture is deemed important, if not almost essential for most efficient operation. Thus in a preferred embodiment of this invention, the hydracarbonylation reaction is initiated in the presence of halide ions which are best provided by use of a halogen acid, especially hydrochloric acid, which preferably is an aqueous acid which may for example have a concentration up to about 25 wt %, but preferably has a concentration in the range of about 5 to about 15 wt %, and more preferably in the range of about 7 to about 15 wt %. It is especially preferred to use approximately 10 wt % aqueous HCl. Dilute aqueous HCl also provides water for effecting the hydracarbonylation. Gaseous HCl can be used to generate hydrochloric acid in situ when water is present when conducting this reaction. HBr and hydrobromic acid may be used, but these appear less effective based on studies conducted to date. Other acids may be considered for use but to date the most effective material is the aqueous hydrochloric acid. Any suitable proportion of hydrochloric acid may be used, typically a reaction accelerating quantity in the range that provides up to 1 mole of hydrogen ion per mole of compound of Formula (I), and preferably a quantity that provides in the range of about 0.1 to about 0.5 mole of hydrogen ion per mole of the compounds of Formula (I). In the case of carbonylation of MVN, the preferred range is an HCl:MVN mole ratio of about 0.1 to about 0.3, more preferably about 0.15 to about 0.27, and most preferably about 0.18 to about 0.22.

The catalytic carbonylation process of this invention is conducted in the presence of a reaction-promoting quantity of (i) palladium and/or at least one palladium compound in which the palladium has a valence of zero, 1 or 2, (most preferably 2) or (ii) a mixture of (a) palladium and/or at least one palladium compound, and (b) at least one copper compound, with (iii) at least one tertiary phosphine of the type described above. When a copper compound is not employed, the palladium and/or one or more compounds of palladium used in forming the catalyst is/are sometimes collectively referred to herein for convenience as "the Pd ingredient", and the combination of palladium and/or one or more compounds of palladium and one or more compounds of copper used in forming the catalyst (when a copper compound is employed) is sometimes collectively referred to herein for convenience as "the Pd—Cu ingredient".

Thus in general the Pd ingredient and the tertiary phosphine ligand are the same type of materials as described above in connection with the arylation reaction. Indeed the same preferred types of materials preferred for use in the arylation reaction are preferred for use in the carbonylation reaction. Fresh catalyst is employed for each such reaction, however. The same species of Pd ingredient and the same species of tertiary phosphine ligand need not be used in these two reactions. Either such component or both of them might differ. Thus, for example, palladium(II) chloride and triphenyl phosphine might be used in the arylation and palladium (I) acetate and tri-o-tolylphosphine might be used in the carbonylation, or vice versa, but in the most preferred case the same species ($PdCl_2$ and neomenthyldiphenylphosphine) are in fact used in both such reactions.

As in the case of the arylation reaction, active catalytic species are preferably formed in situ by the addition to the reaction mixture of the individual components. However the catalyst can be preformed externally to the reaction mixture and charged to the reactor as a preformed catalyst composition.

When it is desired to use a copper compound in forming the carbonylation catalyst system, copper complexes such as copper acetylacetonates, copper alkylacetoacetates, or other chelated forms of copper may be used. The preferred copper compounds for this use, however, are salts especially divalent copper salts such as the halides (chloride, bromide, iodide) of copper(II) and the carboxylates of copper(II) such as copper(II) acetate, copper(II) propionate, etc.

In one embodiment, the Pd ingredient and copper compounds are inorganic salts and are added as a preformed complex of, for example, a complex formed from palladium (II) chloride or bromide, copper(II) chloride or bromide and carbon monoxide, or any other similar complex. In a preferred embodiment, active catalytic species are formed in situ by the addition to the reaction mixture of the individual components, i.e., either (i) at least one tertiary phosphine and at least one palladium compound such as the inorganic or carboxylate salts of palladium(II), or (ii) at least one tertiary phosphine, at least one copper compound, and at least one palladium compound such as the inorganic or carboxylic salts of palladium(II) and copper(II). These inorganic salts include the chlorides, bromides, nitrates, and sulfates. Organic palladium and/or copper compounds that may be used include complexes and salts such as the carboxylates, e.g., the acetates or propionates, etc. In one preferred embodiment, neomenthyldiphenylphosphine, copper(II) chloride, and palladium(II) chloride are used and are added individually or together, either simultaneously or sequentially. In another preferred embodiment, neomenthyldiphenylphosphine and palladium(II) chloride are used and are added individually or together, either simultaneously or sequentially.

The Pd ingredient or the Pd—Cu ingredient may be supported on carbon, silica, alumina, zeolite, clay and other polymeric materials, but use of a homogeneous catalyst system is definitely preferable.

The amount of the Pd ingredient or of the Pd—Cu ingredient employed is preferably such as to provide from about 4 to about 8000 moles of the compound of Formula (I) per mole of the Pd ingredient or per total moles of the Pd—Cu ingredient. More preferred is an amount to provide from about 40 to 4000 moles (most preferably about 20 to 2000 moles) of the compounds of Formula (I) per mole of the Pd ingredient or per total moles of the Pd—Cu ingredient. The process of this invention is conducted in the presence of at least one mole of the tertiary phosphine per mole of the Pd ingredient or per total moles of the Pd—Cu ingredient. More preferably, about 1 to about 40 moles of tertiary phosphine are used per mole of the Pd ingredient or per total moles of the Pd—Cu ingredient, and most preferably about 1 to about 20 moles of tertiary phosphine are used per mole of the Pd ingredient or per total moles of the Pd—Cu ingredient.

The presence of a solvent is not always required in the carbonylation reaction, although it is desirable in some circumstances. Those solvents which can be used include one or more of the following: ketones, for example, acetone, methyl ethyl ketone, diethyl ketone, methyl n-propyl ketone, acetophenone, cyclohexanone, and the like; linear, poly and cyclic ethers, for example, diethyl ether, di-n-propyl ether, di-n-butyl ether, ethyl n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol isomers of butanol, isomers of pentanol, etc. Esters may also be used, such as ethyl acetate, etc. When an ester or an alcohol is used as solvent, the product is usually the corresponding ester of the carboxylic acid. Most highly preferred are ethers, especially tetrahydrofuran, or mixtures of one or more ethers and one or more ketones, especially mixtures of tetrahydrofuran and diethyl ketone. When solvents are used, the amount can be up to about 100 mL per gram of the compounds of Formula (I), but the process is most advantageously conducted in the presence of about 1 to 30 mL per gram of the compound of Formula (I).

In those specific embodiments of this invention in which an ester is produced, e.g. ibuprofen alkyl ester, the ester may be conveniently converted to the acid (ibuprofen itself) by conventional methods of hydrolysis. Base hydrolysis can also be employed if desired to produce pharmaceutically acceptable salts wherein the cation is sodium, potassium, calcium, hydrogen carbonate or a quaternary ammonium compound.

Workup and Recovery of Carbonylation Product

As noted above, the carbonylation reaction forms a reaction product composition comprising arylalkylcarboxylic acid or substituted arylalkylcarboxylic acid (e.g., racemic 2-(6-methoxy-2-naphthyl)propionic acid or 2-(4-isobutylphenyl)propionic acid, etc.) or an ester thereof (depending on whether water or an alcohol is used in the carbonylation process), and a liquid medium comprising polar organic solvent (preferably one or more ketones), water and/or alcohol, HCl, and preferably at least one ether (e.g., THF, etc.) with a boiling temperature below that of at least one such polar solvent. Also present are catalyst residues and typically some coproducts formed during the reaction.

Pursuant to a preferred embodiment of this invention, the arylalkylcarboxylic acid or substituted arylalkylcarboxylic acid is converted in situ into an inorganic salt of such acid by reaction with an aqueous solution of inorganic base (neutralization step). In addition, when the reaction product composition contains (i) at least one low boiling ether (e.g., THF, etc.) and/or (ii) at least one low boiling polar solvent, where either or both such low boiling materials boil(s) below the boiling temperature of at least one polar solvent contained in the reaction product mixture, some or all of such low boiling materials are distilled from the reaction product composition (distillation step). If the reactor overheads are susceptible to attack by aqueous HCl, the neutralization step should precede or at least be conducted concurrently with the distillation step. On the other hand, if the reactor overheads are formed from acid-resistant materials of construction, the distillation step can precede and/or follow and/or be conducted concurrently with the neutralization step; the HCl in the mixture will not cause excessive corrosion of the reactor overheads even if the distillation precedes the neutralization. In whatever sequence the neutralization step and the distillation step are conducted, a mixture of residual organic phase and an aqueous phase containing dissolved inorganic salt of the arylalkylcarboxylic acid or substituted arylalkylcarboxylic acid remain in the reactor as a distillation residue (distilland or pot residue). These phases are separated from each other. The aqueous phase is then subjected to a distillation, preferably at or near atmospheric pressure, to remove residual organic impurities such as, for example, THF and DEK. At this point it is desirable to ensure that the residual aqueous phase has a concentration in the range of about 10 and about 35 wt % of dissolved inorganic salt of the arylalkylcarboxylic acid or substituted arylalkylcarboxylic acid and where necessary, adjusting the concentration of the aqueous phase to about 10 and about 35 wt % solution by removal or addition of water. The aqueous solution is then washed (extracted) with substantially non-polar liquid organic solvent (preferably a paraffinic solvent, or an aromatic hydrocarbon solvent, such as toluene or xylene), preferably at least twice. The free arylalkylcarboxylic acid or substituted arylalkylcarboxylic acid is then produced by mixing non-oxidizing mineral acid (e.g., sulfuric acid) with the aqueous phase in the presence of substantially non-polar liquid solvent to form (i) an organic phase composed of a solution of arylalkylcarboxylic acid or substituted arylalkylcarboxylic acid in substantially non-polar liquid solvent and (ii) an aqueous phase. After separating these phases from each other, arylalkylcarboxylic acid or substituted arylalkylcarboxylic acid is crystallized from the substantially non-polar liquid solvent.

The aqueous solution of inorganic base used in the above neutralization step is preferably a 10 to 50 wt % solution of NaOH or KOH. However other inorganic bases that can be used include $Na_2O$, $K_2O$, $Ca(OH)_2$, CaO, $Na_2CO_3$, $K_2CO_3$, and other inorganic bases of similar basicity. Such solutions are used in an amount at least sufficient to neutralize the arylalkylcarboxylic acid or substituted arylalkylcarboxylic acid and the HCl present in the reaction product composition.

When the carbonylation reaction is conducted using an alcohol so that an ester of the arylalkylcarboxylic acid or substituted arylalkylcarboxylic acid is present in the reaction product composition, it is preferred to saponify the ester in situ by mixing a concentrated aqueous solution of a strong inorganic base such as NaOH or KOH with the reaction product composition and applying sufficient heat (e.g., heating to a temperature in the range of up to about 80° C.) to form the inorganic salt of the arylalkylcarboxylic acid or substituted arylalkylcarboxylic acid. Then the workup procedure for the carbonylation product as described above is carried out.

The low boiling materials recovered in the initial distillation step are preferably recycled for use in the hydracarbonylation reaction.

Examples of compounds that can be produced by use of the invention include ibuprofen, 2-(4-isobutylphenyl) propionic acid (U.S. Pat. Nos. 3,228,831 and 3,385,886); 2-(3-fluoro-4-biphenylyl)-propionic acid (also known as flurbiprofen) (U.S. Pat. No. 3,755,427); racemic 2-(6-methoxy-2-naphthyl)propionic acid which can be resolved to d-2-(6-methoxy-2-naphthyl)propionic acid (also known as naproxen) (U.S. Pat. No. 3,637,767); α-dl-2-(3-phenoxyphenyl)propionic acid (also known as fenoprofen) (U.S. Pat. No. 3,600,437); and 2-(3-benzoylphenyl) propionic acid (also known as ketoprofen) (U.S. Pat. No. 3,641,127). As described herein, the bromo precursor of each of the above compounds is reacted with an olefinic compound of Formula (III) (most preferably ethylene) in a one-phase organic liquid medium (most preferably a mixture of a liquid ketone, especially diethyl ketone, and a liquid secondary or tertiary amine such as a trialkyl amine, especially triethyl amine), that also preferably contains the above-described reaction accelerating amount of water) in the presence of a palladium catalyst system (as described herein), which is formed from Pd, Pd(I) salt or preferably Pd(II) salt and a tertiary phosphine ligand such as neomenthyldiphenylphosphine. The amine should be selected to avoid beta hydride elimination under reaction conditions and should not react with the olefin or bromo precursor to any appreciable extent. The bromo precursor substitutes on the ethylene to provide the substituted olefin which is then worked up as described above, and then carbonylated (using carbon monoxide and a palladium-phosphine or a palladium-copper-phosphine catalyst system as described herein) to produce the corresponding acid product (if water forms part or all of the solvent system) or the corresponding ester (if an alcohol such as methyl, ethyl or isoamyl alcohol) is used as all or part of the solvent.

Some of the above reactions can be exemplified as follows:

IBUPROFEN

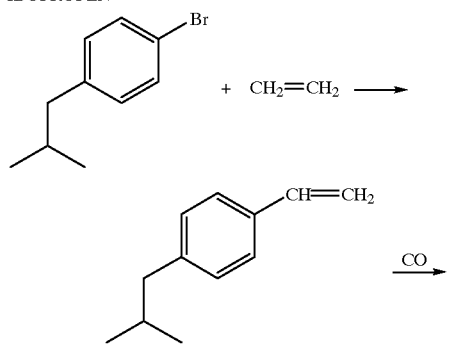

FENOPROFEN:

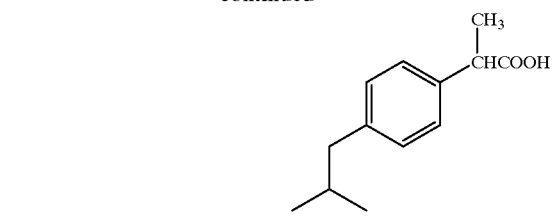

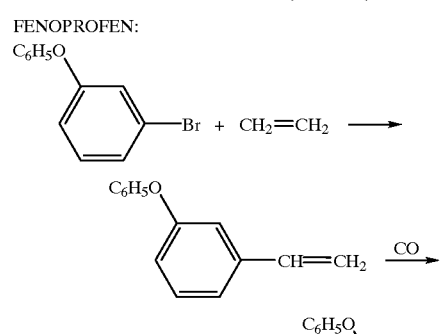

KETOPROFEN:

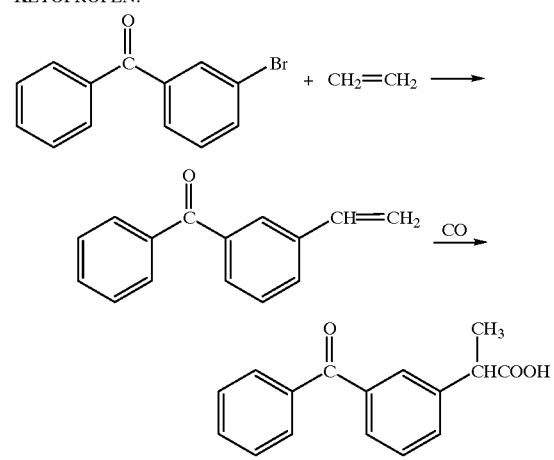

NAPROXEN:

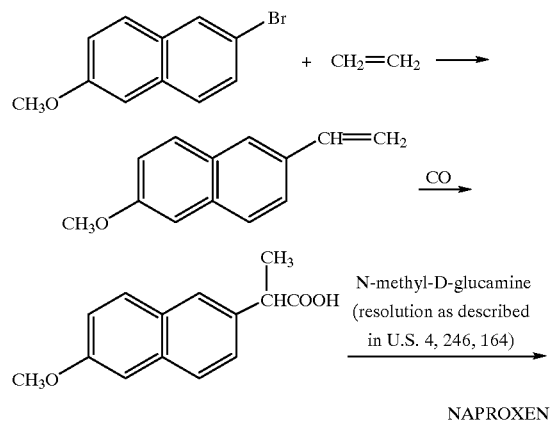

In the above reactions the ethylene pressure should be 50 to 3000 psi (preferably 300 to 1000 psi), the temperature is 30° C. to 200° C. (preferably 60° C. to 150° C.). Temperatures and pressures are selected to minimize by-product formation. Palladium is used (i.e., charged to the reactor) preferably in the form of its salts, (e.g., Pd(II) acetate or chloride) along with a tertiary phosphine ligand as described above, with a cycloalkyldi(alkylphenyl)phosphine such as neomenthylditolylphosphine being preferred, and a cycloalkyldiphenylphosphine such as neomenthyldiphenylphosphine being particularly preferred.

The bromo precursors are frequently commercially available and/or can be readily prepared by those skilled in the art. For example, Aldrich Chemical Company sells m-bromophenol and m-bromoanisole while Albemarle PPC (Thann, France) sells 2-bromo-6-methoxynaphthalene. The bromo precursors of ibuprofen can be prepared by bromination using standard Friedel-Crafts catalysts (e.g., zinc bromide or ferric bromide). The bromo precursor of ketoprofen can be prepared by bromination of methyl benzoate (or a similar lower hydrocarbon ester) using aluminum chloride followed by NaOH hydrolysis, conversion to the acid chloride (e.g., with $SOCl_2$) and reaction with benzene (again, using a Friedel-Crafts catalyst such as $AlCl_3$). The precursor for (±)-2-(6-methoxy-2-naphthyl)propionic acid, viz., 2-bromo-6-methoxynaphthalene, is best made by the process described in commonly-owned U.S. application Ser. No. 08/780,309, filed Jan. 8, 1997, all disclosure of which is incorporated herein.

In addition to the profen compounds described above, other profen compounds which can be prepared under appropriate conditions by use of this invention to convert the corresponding bromo precursors by reaction with ethylene include protizinic acid, tiaprofenic acid, indoprofen, benoxaprofen, carprofen, pirprofen, pranoprofen, alminoprofen, suprofen and loxoprofen.

The following examples are given to illustrate the process of this invention and are not intended as a limitation thereof. Unless otherwise specified all parts and percentages are by weight.

The following designations are used in the examples:

BMN is 2-bromo-6-methoxynaphthalene.

TEA is triethylamine.

DEK is diethyl ketone.

NMDP is neomenthyldiphenylphosphine.

MVN is 6-methoxy-2-vinylnaphthalene.

THF is tetrahydrofuran.

ACN is acetonitrile.

As is well known in the art, the terms or designations "racemic 2-(6-methoxy-2-naphthyl)propionic acid" and "(±)-2-(6-methoxy-2-naphthyl)propionic acid" mean exactly the same thing. For convenience, "sodium racemate" is sometimes used in the examples to refer to racemic sodium 2-(6-methoxy-2-naphthyl)propionate.

Example 1 illustrates a preferred overall procedure for producing racemic 2-(6-methoxy-2-naphthyl) propionic acid on a large (1000 gallon) scale using fresh DEK.

EXAMPLE 1

Arylation Reaction

To a 1000 gallon reactor are charged 750 kg of BMN, 1305 kg of DEK, 368 kg of TEA, 0.3 kg of $PdCl_2$, 3.1 kg of NMDP, and 37 kg of water. The reactor is sealed, pressured to 100 psig with ethylene and the reactor temperature is adjusted to 95° C. The reactor is then pressured to 425–450 psig with ethylene and held at this pressure until the uptake of ethylene is completed. The reactor is cooled to 60° C. and excess ethylene is vented from the reactor. The reaction typically takes 4–6 hours to go to completion and typically gives a >95% BMN conversion and a MVN yield of 85–95%.

Product Workup and Solvent Exchange

To the reaction product from the arylation reaction is added 557 kg of a 25 wt % aqueous sodium hydroxide solution. The mixture is stirred for 15 minutes at 50–60° C. and then allowed to stand for 15 minutes. The bottom aqueous solution is drained from the vessel. The organic phase is then subjected to distillation at reduced pressure, typically in the range of about 200 mm Hg to about 350 mm Hg to distill off TEA to a level at which the weight ratio of TEA:MVN is less than 0.016. After adding THF to the residual organic phase (distilland or pot residue) to form a mixture in which the THF:DEK weight ratio is approximately 1:1, this mixture is filtered to remove solids (palladium catalyst residues and oligomeric or dimeric coproduct).

Hydracarbonylation Reaction

Charged to a 1000 gallon reactor are a filtered THF-DEK-MVN solution produced as in the above workup procedure containing 550 kg of MVN, 825 kg of DEK, and 825 kg of THF, followed by 0.3 kg of $PdCl_2$, 0.64 kg of $CuCl_2$, 3.1 kg of NMDP, and 200 kg of 10 wt % HCl. The reactor is then pressured to 100 psig with carbon monoxide and the reactor temperature is adjusted to 70° C. The reactor is then pressured to 360 psig with carbon monoxide and held at this pressure until the uptake of carbon monoxide is completed. The reactor is then cooled and the pressure is vented. The reaction typically takes 4–8 hours to go to completion with >95% MVN conversion and a yield of racemic 2-(6-methoxy-2-naphthyl)propionic acid of about 90%.

Racemic Product Workup and Recovery

Aqueous sodium hydroxide (25 wt % solution) is added to the reactor to convert the racemic 2-(6-methoxy-2-naphthyl) propionic acid to racemic sodium 2-(6-methoxy-2-naphthyl) propionate, and to neutralize the HCl remaining in the reaction mixture. The THF is then distilled from the reaction mixture at atmospheric pressure. (These neutralization and distillation steps can be reversed if the materials of construction of the reactor overhead are resistant to HCl). The resultant aqueous phase is separated from the organic phase which is composed mainly of DEK and impurities. The residual organics (e.g., DEK) contained in the aqueous phase are distilled from the aqueous racemic sodium 2-(6-methoxy-2-naphthyl)propionate phase at atmospheric pressure. This sodium racemate solution is desirably a 10–35 wt % solution, and if necessary, the concentration is adjusted to fall in this range by removal or addition of water. The aqueous sodium racemate phase is then washed with toluene to remove neutral impurities. Typically one to three toluene washes, preferably at least two, are used. A suitable temperature, typically 60–80° C., is maintained to prevent the racemic sodium 2-(6-methoxy-2-naphthyl)propionate from precipitating. The aqueous solution is then acidified with sulfuric acid in the presence of toluene at about 97° C. The aqueous phase is cut from the bottom of the reactor and the toluene solution of (±)-2-(6-methoxy-2-naphthyl) propionic acid is washed with water (typically twice) at about 95° C. to remove residual sulfuric acid. Racemic 2-(6-methoxy-2-naphthyl)propionic acid is then crystallized from the toluene solution.

Example 2 illustrates a preferred overall procedure for producing racemic 2-(6-methoxy-2-naphthyl)propionic acid on a large (1000 gallon) scale using recycle solvent (principally DEK and TEA) from a process conducted as in Example 1 above.

EXAMPLE 2

To a 1000 gallon reactor are charged 750 kg of BMN, a mixture of recycle solvent (DEK and TEA mixture containing typically about 1 wt % water) to give approximately 1305 kg of DEK and 368 kg of TEA. Catalyst consisting of 0.3 kg of $PdCl_2$, and 3.1 kg of NMDP is charged to the reactor. Fresh water is added (if necessary) to raise the water content of the reaction mixture to approximately 1.6 wt %. The reactor is then pressured to 100 psig with ethylene and the reactor temperature is adjusted to 95° C. The reactor is then pressured to 425–450 psig with ethylene and held at this pressure until the uptake of ethylene is completed. The reactor is cooled to 60° C. and excess ethylene is vented from the reactor. The reaction typically takes 4–6 hours to go to completion and typically gives a >95% BMN conversion and a MVN yield of 85–95%.

Aqueous caustic (25% aqueous NaOH solution) is added to the reaction mixture containing MVN to liberate the TEA from the triethylamine hydrobromide salt. The aqueous layer is then separated from the organic layer, and the TEA is then recovered from the MVN, DEK, and TEA mixture by distillation. The distillate composed of DEK, TEA, and water is then recycled for use in the arylation reaction. THF is added to the distillation residue (distilland or pot residue) composed mainly of a MVN/DEK mixture plus some solids to produce a MVN mixture containing THF and DEK in a weight ratio of about 1:1 suitable for carbonylation. The resultant mixture is filtered to remove the solids therefrom. Fresh catalyst and HCl are added in proportions corresponding to those of Example 1 and the hydracarbonylation reaction is carried out as in Example 1. Then the (±)-2-(6-methoxy-2-naphthyl)propionic acid is converted to sodium (±)-2-(6-methoxy-2-naphthyl)propionate by the addition of 25 wt % aqueous sodium hydroxide solution, and the remainder of the racemic product workup and recovery procedure of Example 1 is carried out.

The procedure of Example 1 above can be conducted in the same manner except for the omission of the reaction accelerating amount of water in the arylation reaction. The reaction proceeds, but proceeds more slowly than if the water is present in the arylation reaction. This is illustrated in Example 3 hereof.

EXAMPLE 3

A series of 12 arylation runs was conducted in a 2-liter reactor in which the proportions of the ingredients and the reaction conditions used were, except for some small inconsequential differences, the same from run to run, the only independent variable being water content and the amount thereof. The reaction mixtures were composed of 300 g of BMN, 529–530 g of DEK, 147–148 g of TEA, 0.112–0.116 g of $PdCl_2$, and 1.23–1.26 g of NMDP. Several runs were conducted with no added water, and the remainder had measured quantities of added water. All reactions were performed at 95° C. under ethylene at 420 to 450 psig. The criterion for reaction rate was maximum rate of ethylene consumption during each reaction. Thus the higher this value, the better. The results of these runs as regards reaction rates are summarized in Table 1.

TABLE 1

| Run No. | Water Content, wt % of Total Reaction Mixture | Maximum Ethylene Consumption, psi/hr |
|---|---|---|
| 1 | None | 38 |
| 2 | None | 38 |
| 3 | None | 39 |
| 4 | 0.8% | 45 |
| 5 | 1.6% | 43 |
| 6 | 1.6% | 49 |
| 7 | 2.25% | 53 |
| 8 | 2.25% | 60 |
| 9 | 3.1% | 58 |
| 10 | 3.1% | 63 |
| 11 | 4.6% | 37 |
| 12 | 5.9% | 42 |

Experimental work has shown that it is advantageous to carry out the separation of solids from the arylation reaction product after the separation of the free amine and the replenishment of the solvent by addition of THF or like solvent (as in Examples 1 and 2), rather than before such separation and solvent addition. In particular, the filtration time is reduced significantly in this manner.

As noted above, if in the arylation reaction more than one solvent/diluent is used, the amine does not have to boil below all such solvent/diluents. Instead it should boil below at least one of the solvent/diluents that makes up a substantial portion (e.g., at least 20 or 30%) of the total weight of such solvent/diluents. For example, a reaction conducted generally as in Example 1 above using a 1:1 (wt:wt) mixture of acetonitrile (ACN) and diethyl ketone (DEK) as the solvent/diluents, involves a situation in which the triethylamine boils above the ACN, but below the DEK. In such case, different workup procedures can be used. In one such procedure the ACN can be distilled (stripped) from the reaction mixture, and then the aqueous inorganic base solution is added followed by the phase separation and distillation of the triethylamine from the remaining organic phase. Another procedure involves adding the aqueous inorganic base solution, conducting the phase separation, and then distilling off the ACN and the triethylamine, leaving the diethyl ketone solution behind.

Additional examples of the practice of this invention are given below.

EXAMPLE 4

Preparation of 6-Methoxy-2-Vinylnaphthalene

A 20-gallon jacketed stainless steel reactor equipped with a mechanical agitator is charged with 19.45 kg of acetonitrile (ACN) and 12.45 kg of 2-bromo-6-methoxynaphthalene (BMN), and 4.8 g of $PdCl_2$. The reactor is pressured and vented three times with 50 psig nitrogen. The reactor is then charged with 5.3 kg of ACN and 5.64 kg of triethylamine (TEA). The agitator is set at 158 rpm and the reactor is pressured and vented three times with 80 psig nitrogen. The reactor is then purged for ten minutes with nitrogen. Next a mixture of 48.6 g of neomenthyldiphenylphosphine (NMDP) dissolved in 0.35 kg of TEA is charged to the reactor. The agitator is set to 412 rpm and the reactor is heated with steam on the jacket. The reaction temperature is initially in the range of 91–109° C., while the pressure varies from 412–519 psig. The reaction produces a heat kick, and after 30 minutes the temperature rises to 109° C. with 26° C. cooling water on the jacket. The total reaction time is 1.75 hours with a BMN conversion of 100%. The reactor is cooled, vented, and the reactor contents are transferred to a 30-gallon glass lined reactor for workup.

Workup of 6-Methoxy-2-Vinylnaphthalene

The crude 6-methoxy-2-vinylnaphthalene (MVN) solution in the 30-gallon reactor is stripped at 330 mm Hg to remove the ACN. The total strip time is 6.33 hours with a maximum bottoms temperature of about 91° C. The final overhead temperature is about 68° C. Zero reflux is used for the first 35 minutes of operation. The reflux ratio is then set to five, and 34.95 kg of diethyl ketone (DEK) is added to the reactor contents. The reflux ratio remains at five for the duration of the strip.

After charging 9.25 kg of 25% NaOH to the stripped reaction product in the 30-gallon reactor, the resultant mixture is agitated for 30 minutes. Then the agitator is shut off and the aqueous phase is allowed to settle for 1.75 hours. The mixture is phase cut at 57° C., and the aqueous phase is collected and discarded. The organic phase and rag layer in the reactor are stripped to remove TEA. The strip pressure is 330 mm Hg. The total strip time is 4.9 hours. The column is started up under total reflux for the first 30 minutes of operation. The reflux ratio is then lowered to three for 3.5 hours. The reflux ratio is reduced to two for the remainder of the strip. The final overhead temperature is about 79° C. and the final bottoms temperature is about 86° C.

To the cooled-down stripped mixture in the 30-gallon reactor is added 8 kg of tetrahydrofuran (THF). The resultant MVN solution is filtered through a 10 micron bag filter and a 1 micron cartridge filter.

Hydracarbonylation of 6-Methoxy-2-Vinylnaphthalene

A 20-gallon Hastelloy reactor is purged three times with 80 psig nitrogen, and then 3.8 g of $PdCl_2$ and 8.8 g of $CuCl_2$ are charged to the reactor, followed by the MVN solution. The reactor is purged three more times with 80 psig nitrogen and the agitator is set to 118 rpm. After charging 3.6 kg of THF and 3.55 kg of 10% HCl to the reactor, the reactor is again purged three times with 80 psig nitrogen and then nitrogen is bubbled through a dip leg for ten minutes. Next, a mixture of 42.2 g of NMDP and 0.35 kg of THF is charged to the reactor and the agitator is set at 402 rpm. The reactor is pressured and vented three times with 50 psig CO, and then heated to reaction temperature and pressured with CO. The reaction temperature is in the range of 70 to 78° C., while the pressure varies from 247 to 450 psig. After a total reaction time of 8.5 hours the reactor is cooled and vented, and the contents transferred to a 30-gallon glass-lined reactor for workup.

Product Workup

The hydracarbonylation mixture is neutralized with 2.05 kg of 25% NaOH. THF is stripped at atmospheric pressure from the workup reactor contents over 2.5 hours. Water (30.7 kg) is charged 1.4 hours into the strip. The final overhead temperature is about 97° C. and the final bottoms temperature is about 108° C. To the stripped reactor contents is added 7 kg of 25% NaOH, and the mixture is agitated for 30 minutes at 50–60° C. After a 35-minute settling time, the aqueous and organic phases are separated from each other. The aqueous phase is charged back to the workup reactor along with 10 kg of toluene. This mixture is agitated for 15 minutes and allowed to settle for 30 minutes at 55° C. The phases are again separated. The aqueous phase is charged back to the workup reactor along with 10 kg of toluene, the mixture is stirred for 15 minutes and then allowed to settle. The mixture is then heated to 65° C. and the phases are separated from each other. The aqueous phase is again charged back to the reactor along with 10 kg of toluene. The mixture is stirred for 15 minutes and allowed to settle for 30 minutes at 70° C., and a final phase cut is made. The separated aqueous phase is a clear amber aqueous solution of sodium (±)-2-(6-methoxy-2-naphthyl)propionate.

EXAMPLE 5

The procedure of Example 4 is repeated substantially as described with the following principal changes:

The initial charge to the first reactor is 21.4 kg of diethyl ketone (DEK), 12.4 kg of BMN, and 4.6 g of $PdCl_2$. The second charge is 3.2 kg of DEK and 6.34 kg of TEA. The 10-minute nitrogen purge after the addition of the TEA addition is eliminated. The NMDP charge (50.9 kg) is added as a solution in 0.27 kg of DEK. The pressurizing with ethylene is started to 100 psig before beginning the heat up of the reactants. This arylation reaction is conducted at 92–98° C. and 393–429 psig.

The MVN workup involves addition of 10.15 kg of DEK, heating to 75° C., followed by the caustic wash, a phase cut, a water wash, another phase cut, and the TEA strip with a final overhead temperature of about 79° C. and a maximum bottoms temperature of about 97° C.

The hydracarbonylation solvent is a mixture of residual DEK and 8.2 kg of added THF. The other components charged are 3.5 g of $PdCl_2$, 7.9 g of $CuCl_2$, 3.25 kg of 10% HCl, 37.9 g of NMDP in 160 g of DEK. The hydracarbonylation reaction is performed for 8.7 hours, with temperatures in the range of 74 to 84° C. and pressures in the range of 321 to 476 psig.

The crude (±)-2-(6-methoxy-2-naphthyl)propionic acid is stripped of THF, converted to sodium (±)-2-(6-methoxy-2-naphthyl)propionate and washed three times with 5 kg of toluene to yield an aqueous solution of sodium (±)-2-(6-methoxy-2-naphthyl)propionate.

EXAMPLE 6

Preparation of 6-Methoxy-2-Vinylnaphthalene

A 20-gallon jacketed stainless steel reactor equipped with a mechanical agitator is charged with 12.8 kg of ACN, 12.45 kg of DEK and 12.4 kg of 2-bromo-6-methoxynaphthalene (BMN), 4.6 g of $PdCl_2$, and 50.9 g of NMDP. The reactor is pressured and vented three times with 50 psig nitrogen. The reactor is then charged with 6.27 kg of TEA. The agitator is set at 158 rpm and the reactor is pressured and vented with 50 psig nitrogen. The agitator is set to 416 rpm, the reactor is pressured to 100 psig with ethylene and heated with tempered water on the jacket. The reaction temperature ranges from 87 to 98° C., while the pressure varies from 394 to 458 psig. The total reaction time is 3.5 hours with a BMN conversion of 99.6% in two hours. The reactor is cooled, vented, and the reactor contents at 60° C. are transferred for workup, to a 30-gallon glass lined reactor equipped with a 6-inch column. The 20-gallon reactor is then charged with 12.5 kg of DEK, which is then heated to 60° C. and transferred to the 30-gallon reactor.

Workup of 6-Methoxy-2-Vinylnaphthalene

The crude 6-methoxy-2-vinylnaphthalene (MVN) solution in the 30-gallon reactor is stripped at 150 mm Hg to remove the ACN. The total strip time is 4 hours with a maximum bottoms temperature of about 73° C. The final overhead temperature is about 59° C. Reflux ratios used are 5:1 for 1.9 hours, 3:1 for 1.6 hours, and 4:1 for 1.5 hours.

After charging 9.3 kg of 25% NaOH to the stripped reaction product in the 30-gallon reactor, the resultant mixture is agitated for 15 minutes at 35° C. Then the agitator is shut off and the aqueous phase is allowed to settle for 30 minutes. The mixture is phase cut and the organic phase is washed in the reactor with 1.2 kg of water with stirring for 15 minutes. After allowing a settling period of 30 minutes, another phase cut is made. A TEA strip of the organic phase is conducted at 150 mm Hg. The total strip time is 5.25 hours. The highest overhead temperature is about 59° C. and the maximum bottoms temperature is about 91° C. The reflux ratios were 50:1 at start up, and when the column stabilized, the reflux ratio was reduced to 5:1 for 2.25 hours and 7:1 for the final 2.5 hours of the strip. The reaction product is then diluted by addition to the reactor of 12.05 kg of THF and 2.05 kg of DEK. The resulting solution is then filtered through a ten-micron bag filter and a one-micron cartridge filter.

Hydracarbonylation of 6-Methoxy-2-Vinylnaphthalene

The filtered MVN solution is charged to a 20-gallon Hastelloy reactor followed by an additional 4.65 kg of DEK. Then 4.6 g of $PdCl_2$ and 10.5 g of $CuCl_2$ are charged to the reactor. The reactor is purged three times with 50 psig nitrogen, and 4.2 kg of 10% HCl is charged. The reactor is pressured to 80 psig with nitrogen and vented. A solution of 50.9 g of NMDP in 255 g of DEK is charged to the reactor and the reactor is pressured and vented twice with 50 psig nitrogen with the agitator running only when pressurizing. The agitator speed is set at 399 rpm and the reactor is pressured and vented three times with 50 psig CO, again agitating only during pressurization. The reactor is then pressured to 280 psig with CO and heated to 75° C. The reaction temperature is kept in the range of about 73 to about 77° C., while the pressure varies from 339 to 350 psig. After a total reaction time of 6 hours the reactor is cooled and vented, and the contents transferred to a 30-gallon glass-lined reactor for workup.

Product Workup

The hydracarbonylation mixture is neutralized with 2.15 kg of 25% NaOH. THF is stripped from the hydracarbonylation mixture at atmospheric pressure over 1.2 hours. The final bottoms temperature is 100° C. and the final overhead temperature is 92° C. Water (30.7 kg) is charged 1.4 hours into the strip. The final overhead temperature is about 97° C. and the final bottoms temperature is about 108° C. DEK (4.95 kg) is added to the stripped reactor contents, followed by 14 kg of water and 7.55 kg of 25% NaOH, and the mixture is agitated for 30 minutes at 70–80° C. After a 30-minute settling time, the aqueous and organic phases are separated from each other. The aqueous phase is charged back to the workup reactor and stripped of DEK with a final bottoms temperature of about 95° C. and a final overhead temperature of about 95° C. A 2.0 kg water charge is added along with 5.15 kg of toluene. This mixture is agitated for 20 minutes and allowed to settle overnight with 60° C. tempered water in the jacket. The phases are then separated. The aqueous phase is washed two more times with toluene (the first time with 5.1 kg, the second time with 4.95 kg) each time followed by a phase separation. The product is recovered as a water solution of sodium (±)-2-(6-methoxy-2-naphthyl)propionate.

EXAMPLE 7

Preparation of 6-Methoxy-2-Vinylnaphthalene

The 20-gallon jacketed stainless steel reactor is charged with a 12.5 kg of ACN, 12.5 kg of methyl isobutyl ketone (MIBK), and 12.45 kg of BMN, 4.6 g of $PdCl_2$, and 50.9 g of NMDP. The reactor is pressured and vented three times with 50 psig nitrogen. Then 6.8 kg of TEA is charged. The agitator is set at 160 rpm and the reactor is pressured and vented with 50 psig nitrogen. The agitator is set to 415 rpm, the reactor is pressured to 100 psig with ethylene, and heated with tempered water on the jacket. The reaction temperature ranges from 94 to 100° C., while the pressure varies from 388 to 432 psig. The total reaction time is 2.6 hours, but the reaction reaches about 99% conversion in about 1.8 hours. The reactor is cooled and the ethylene pressure is vented. After standing for about 16 hours with the agitator in operation, the reactor is heated to approximately 60° C. and the reactor contents are transferred to the 30-gallon glass-lined workup reactor. The 20-gallon reactor is charged with 12.4 kg of MIBK, which is then heated to about 60° C. and also transferred to workup reactor.

Workup of 6-Methoxy-2-Vinylnaphthalene

The crude MVN solution is stripped at 150 mm Hg to remove the ACN. The total strip time is 3.3 hours with a maximum bottoms temperature of about 76° C. A reflux ratio of 50 is used to line out the column. After the column stabilizes, the reflux ratio is reduced to five. This reflux ratio is maintained for 45 minutes and then reduced to three for 30 minutes. The reflux ratio is set at two for the next 55 minutes before finally switching to zero reflux for the last 25 minutes.

After cooling to 47° C., 9.4 kg of 25% NaOH is charged to the stripped mixture. The temperature drops with the addition of the caustic. The reactor is agitated for 15 minutes and then the agitator is shut off and the aqueous phase is allowed to settle for 30 minutes. The phases are separated, and a 1.05 kg water wash is charged to the organic phase and mixed therewith for 20 minutes. This is allowed to settle for 80 minutes and the aqueous phase is cut from the bottom of the reactor.

The TEA strip pressure is initially 150 mm Hg and is lowered throughout the strip to a final value of 70 mm Hg. The total strip time is 4.25 hours with a maximum bottoms temperature of about 78° C. The column is started up with a zero reflux ratio for the first 35 minutes of operation. The reflux ratio is then set at five and held there for 25 minutes. The reflux ratio is decreased to two for the final 3.25 hours of the strip. To the stripped product mixture is charged 8.1 kg of THF and the resultant MVN solution is filtered through a ten micron bag filter and a one micron cartridge filter. An additional 4.05 kg of THF is charged to the workup reactor and this is also filtered.

Hydracarbonylation of 6-Methoxy-2-Vinylnaphthalene

The MVN solution is transferred to the above hydracarbonylation reactor. To this are charged 4.3 g of $PdCl_2$ and 9.8 g of $CuCl_2$. The reactor is purged once with 50 psig nitrogen. The agitator is set to 118 rpm and 3.95 kg of 10% HCl is charged. The reactor is pressured to 80 psig with nitrogen and vented twice (agitating during pressurization, no agitation during the vent). A solution of 47.6 g NMDP in 248 g DEK is charged. The agitator speed is set at 401 rpm and the reactor is pressured and vented three times with 50 psig CO (agitating during pressurization, no agitation during the vent). The reactor is then pressured to 276 psig with CO and heated to 75° C. The reactor temperature varies from about 72 to about 80° C. and the pressure range is about 334 to 355 psig. The reaction is shutdown after 8.8 hours.

Product Workup

The (±)-2-(6-methoxy-2-naphthyl)propionic acid solution is charged to a workup reactor and neutralized with 2.0 kg of 25% NaOH. THF is stripped at atmospheric pressure over 20 minutes. The final bottoms temperature is about 79° C. and the final overhead temperature is about 77° C. The stripped mixture is cooled to 60° C. and to this are charged 14.0 kg of water and 8.0 kg of caustic. The mixture is agitated for 30 minutes at 75° C. The agitator is shut off and the contents of the reactor are allowed to settle for 30 minutes. The phases are separated. The aqueous solution is charged back to the reactor and left agitating for about 16 hours. The aqueous solution is then stripped at atmospheric pressure for 1.5 hours. The aqueous phase in the column is cut back to the reactor. One more strip is done using steam on the jacket. Additional distillate is drained from the column following the strip. The final bottoms temperature for the strip is about 101° C. and the final overhead temperature is about 100° C. A 5.05 kg charge of toluene is added to stripped product mixture, and the mixture is agitated for 20 minutes at 68° C. then allowed to settle for 30 minutes. The phases are cut to give an amber-orange aqueous solution and a dark-green organic solution. The aqueous solution is washed with 5.0 kg of toluene, giving a reddish-purple clear aqueous solution and a cloudy olive-green organic solution. The third toluene wash (5.05 kg, 71° C.) produces a clear purple aqueous solution and a cloudy yellow organic solution.

EXAMPLE 8

The procedure of Example 7 is repeated substantially as described with the following principal changes:

The initial charge to the first reactor is 12.4 kg of ACN, 12.65 kg of DEK, 12.45 kg of BMN made as in Example 7 hereof, 4.6 g of PdCl$_2$, and 51 g of NMDP. The second charge is 6.17 kg TEA. This 2.5-hour arylation reaction is conducted at 88–99° C. and 318–458 psig.

The ACN distillation in the MVN workup is at 150 mm Hg and involves a total strip time of 5.25 hours with a maximum bottoms temperature of 71.8° C. The TEA strip pressure is initially 150 mm Hg and is lowered throughout the 4-hour strip to a final value of 90 mm Hg.

The hydracarbonylation solvent is a mixture of residual DEK and about 12 kg of added THF. The other components charged are 4.1 g of PdCl$_2$, 9.2 g of CuCl$_2$, 3.65 kg of 10% HCl, 44.7 g of NMDP in 222 g of DEK. The hydrocarbonylation reaction runs for 6.6 hours, with temperatures in the range of 74 to 77° C. and pressures in the range of 333 to 358 psig.

As in Example 7, the crude (±)-2-(6-methoxy-2-naphthyl) propionic acid is converted to sodium (±)-2-(6-methoxy-2-naphthyl)propionate, stripped of THF, and washed three times, each time with 5 kg of toluene, to yield an aqueous solution of sodium (±)-2-(6-methoxy-2-naphthyl) propionate.

EXAMPLE 9

The procedure of Example 7 is repeated substantially as described with the following principal changes:

The initial charge to the first reactor is 12.55 kg of ACN, 12.5 kg of MIBK, 12.5 kg of BMN made as in Example 7 hereof, 4.6 g of PdCl$_2$, and 51 g of NMDP. The second charge is 6.19 kg TEA. This 2.7-hour arylation reaction is conducted at 88–97° C. and 371–441 psig.

The ACN distillation in the MVN workup is at 150 mm Hg and involves a total strip time of 3.8 hours with a maximum bottoms temperature of 71° C. The TEA strip pressure is initially 150 mm Hg and is lowered throughout the 5.3-hour strip to a final value of 70 mm Hg.

The hydracarbonylation solvent is a mixture of residual MIBK and about 12 kg of added THF. The other components charged are 4.6 g of PdCl$_2$, 9.5 g of CuCl$_2$, 3.85 kg of 10% HCl, 47 g of NMDP in 226 g of DEK. The hydracarbonylation reaction is conducted for 7 hours, with temperatures in the range of 72 to 77° C. and pressures in the range of 333 to 357 psig.

As in Example 7, the crude (±)-2-(6-methoxy-2-naphthyl) propionic acid is converted to sodium (±)-2-(6-methoxy-2-naphthyl)propionate, stripped of THF, and washed three times, each time with 5 kg of toluene, to yield an aqueous solution of sodium (±)-2-(6-methoxy-2-naphthyl) propionate.

Example 10 illustrates a preferred procedure for producing BMN starting material for use in the practice of this invention.

EXAMPLE 10

Bromination of 2-Naphthol

2-Naphthol (144.8 g, 1.00 mol), EDC (537 g), and water (162 g) are charged to a 2-L reactor equipped with a reflux condenser, mechanical stirrer and peristaltic pump addition system. The reactor is heated to about 55° C. until most of the β-naphthol is dissolved. Bromine (336.9 g, 2.11 mol) is then added (sub-surface) via a pump at such a rate so as to maintain the reaction temperature at 60° C. After the bromine addition, the reaction temperature is maintained at 60° C. for 1.5 hour. The reaction is then cooled slightly and the lower phase (aq. HBr) siphoned off. The remaining EDC solution (841 g) is transferred out of the reactor and analyzed by GC. In a run conducted in this manner, the analysis showed 0.4% 2-naphthol, 92.6% 1,6-dibromo-2-naphthol (DBN), and 4.9% of other isomers.

Hydrodebromination of 1,6-Dibromo-2-Naphthol

A solution of DBN (271 g, 0.9 mol) in ethylene dichloride (EDC) (551 g), obtained from the bromination reaction, is charged in a 1000 mL Hastelloy B autoclave. Tungsten carbide (82 g, 30 wt %) and tetrabutylammonium bromide (0.2 g, 0.1 wt %) are added and the reactor is sealed. The reactor is purged with hydrogen (50 psig) and vented three times and then pressured with hydrogen and heated to 90° C. A constant purge of hydrogen is maintained in such a rate that the pressure remains in the 120–125 psig range. Analysis of a reaction mixture produced after 5.5 hours in this manner showed 90% 6-bromo-2-naphthol, 2% DBN, and 2% 2-naphthol. The reactor is cooled to room temperature, vented to scrubbers, and the catalyst is permitted to settle. The EDC solution (747 g in a reaction conducted in this manner) is removed through the dip tube.

Methylation of 6-Bromo-2-Naphthol with MeCl

The EDC solution formed as above is transferred to a 1.4-liter (three pints) Chemco glass reactor with stainless steel head. It is first neutralized with dilute acid and then concentrated by distillation. Water (50 mL) is added to azeotropically remove traces of EDC left in the residue. Isopropyl alcohol (242 g) and sodium hydroxide (44 g, 1.1 mol; 88 g of 50% solution) are charged into the reactor. The reactor is sealed, purged with nitrogen, and heated to 70° C. Methyl chloride (MeCl) (66 g, 1.3 mol) is charged over a period of one hour (40–50 psig). After stirring at 80° C. for another hour, isopropyl alcohol is removed by distillation. The residue is heated to melted condition (90–95° C.) and then it is washed with water (400 g). Water is removed and the residue is distilled under vacuum (1 mm Hg). After removing small amounts of volatile materials, BMN is distilled at 160–165° C. as a white solid (169 g was formed in an operation conducted in this manner). Isopropyl alcohol (490 g) is added and the solution was heated to reflux and then slowly cooled down to about 10° C. Solid BMN is removed and washed with cold (0° C.) isopropyl alcohol (180 g) and then dried under vacuum at 70–75° C. Analysis of the white crystalline product formed in this manner showed 99.7 wt % BMN.

Example 10 involves procedures and subject matter described in full in commonly-owned copending application Ser. No. 08/780,309, filed Jan. 8, 1997, the entire disclosure of which is incorporated herein by reference.

EXAMPLE 11

Preparation of m-Vinylbenzophenone (MVBP) with Caustic Workup

Charge $PdCl_2$ (60.0 mg, 0.338 mmol, 0.0005 eq), NMDP (550 mg, 1.70 mmol, 0.0025 eq), and m-bromobenzophenone (MBBP) (175 g, 0.670 mol, 1.0 eq), $Et_3N$ (80.0 g, 0.791 mol, 1.18 eq), DEK (285 g), and $H_2O$ (15.0 g, 0.832 mol, 2.7 wt % of total reactants) to an autoclave (Hastelloy B, 1-liter). Seal the reactor and set up in a hood. Purge the reactor with nitrogen (3×50 psig) and then heat the mixture to 95° C. (e.g. for about 25 minutes), with stirring (1000 rpm). Charge ethylene to 430 psig and keep ethylene pressure at 430 psig. Monitor the ethylene pressure uptake and stop the reaction in 7.5 hours. Cool to room temperature and release the pressure. Add NaOH (25 wt %, 119 g, 0.744 mol) to the reactor using a syringe. Heat the mixture to 50° C. for 10 minutes and then cool to 35° C. Open the reactor and pour the mixture to a 1-liter separation funnel. Phase cut after settling for 30 minutes (about 1–2% rag of total volume). Remove the rag layer and filter through a medium fritted funnel. Air-dry the precipitate to give the 0.44 g grey solid. ICP analysis of this solid showed 3.59% Pd and 112 ppm P. About 44% palladium recovered in this solid. Transfer the top organic layer to a 1-liter, round-bottom flask and strip the $Et_3N$ and DEK by use of a Rotavapor apparatus at 60° C. to about 185 g. Add additional 100 g DEK and strip again to about 190 g. Add DEK (269 g) to the flask and the mixture is used for the carbonylation step without further treatment. Assuming 100% conversion and 100% yield, this mixture should contain 139 g MVBP and 320 g DEK.

Preparation of Ketoprofen

Transfer the reaction mixture to an autoclave (Hastelloy B, 1-L). Wash the flask with DEK (40 g) and transfer the washing to the autoclave (360 g DEK total). Charge HCl (10%, 54.0 g), $PdCl_2$ (60.0 mg, 0.338 mmol), and NMDP (600 mg, 1.85 mmol). Seal the reactor and set up in the hood. Purge the reactor with $N_2$ (3×50 psig) and pressurize with CO to 200 psig. Heat the reaction mixture to 75° C. with stirring (1000 rpm). CO pressure increased to 250 psig at 75° C. Set the pressure to 330 psig and charge CO to the desired pressure. Let the reaction run overnight. The recorder showed the reaction stopped taking CO in about 8 hours. Cool the reaction mixture to room temperature and release CO pressure. Open the reactor and transfer the reaction mixture to a 1-L, round-bottom flask. Neutralize the reaction mixture with NaOH (25 wt %, 28 g) to pH=7. Add NaOH (25 wt %, 118 g) and $H_2O$ (200 g) and agitate the mixture for 10 minutes. Transfer the mixture a separation funnel and settle for 30 minutes. Phase cut the bottom aqueous layer and extract the organic and rag layers with NaOH (3 wt %, 50 mL). Phase cut the aqueous layer after settling for 30 minutes. Combine the aqueous layers and wash with toluene (2×150 mL and 2×100 mL, settle for 15 minutes before each phase-cut). Acidify the aqueous layer with $H_2SO_4$ (75 wt %, 110 g) to pH<1. Extract the acidified aqueous layer with toluene (250 mL, then 2×150 mL). Wash the combined organic layers with NaCl (15%, 50 mL), $H_2O$ (100 mL), NaCl (15%, 50 mL), and $H_2O$ (100 mL). GC analysis showed ketoprofen (99.8 GC area %) and linear ketoprofen (0.2 GC area %). Branched and linear ratio was 506:1. Strip toluene under vacuum at 60° C. to give an orange syrup (159 g). It solidified upon standing to give a tan solid. Remove the remaining toluene under vacuum at 60° C. overnight to give a tan solid (151 g, 88.6% yield).

FURTHER DETAILED DESCRIPTION—
FOURTH, FIFTH AND SIXTH EMBODIMENTS

It will be recalled that the fourth embodiment comprises:

A) conducting a palladium-catalyzed arylation of an olefin with aryl halide and/or substituted aryl halide in a liquid medium formed from (i) at least one liquid polar organic solvent/diluent, and (ii) at least one secondary or tertiary amine hydrogen halide acceptor capable of forming a water-soluble amine-hydrohalide, to form a reaction mixture comprising olefinically-substituted aromatic compound, amine-hydrohalide and one or more polar organic solvents;

B) contacting (i) at least a portion, and preferably all, of the reaction mixture from A) with (ii) an aqueous mineral acid to form (i) an aqueous phase containing dissolved amine-hydrohalide and, optionally another water-soluble amine salt of the mineral acid, and (ii) an organic phase comprising olefinically-substituted aromatic compound and one or more polar organic solvents;

C) separating the foregoing phases from each other;

D) conducting a palladium-catalyzed carbonylation of at least a portion of said olefinically-substituted aromatic compound with carbon monoxide and water and/or alcohol in a liquid medium comprising one or more liquid polar organic solvent/diluents.

Steps A) and D) of the fourth embodiment utilizes materials and reaction conditions described above in connection with the first, second and third embodiments. Examples of suitable liquid solvent/diluents for use in Step A) of the fourth embodiment include tetrahydrofuran, 1,4-dioxane, diglyme, triglyme, acetonitrile, propionitrile, benzonitrile, N,N-dimethylformamide, N,N-dimethylacetamide, dimethylsulfoxide, nitrobenzene, sulfolane, acetone, butanone and cyclohexanone. Preferred solvent/diluents are one or more aprotic solvents each having a dielectric constant of at least about 10 (especially 10 to 30) at a temperature in the range of 20 to 25° C. From the cost-effectiveness standpoint, hydrocarbyl ketones with 4 or more carbon atoms in the molecule (e.g., 4 to about 8) are especially preferable. Examples include diethyl ketone, methyl isobutyl ketone, 2-pentanone, 2-hexanone, 2-heptanone, 3-heptanone, 4-heptanone, and like liquid ketones, as well as mixtures of two or more such ketones. Most preferred are diethyl ketone (3-pentanone), methyl ethyl ketone, and methyl isobutyl ketone. By use of suitable solvent/diluent(s) in A) above a very clean interface can be formed between the aqueous and organic phases formed in B), and the absence of a so-called "rag layer" at the interface greatly facilitates the phase separation of C), and enables efficient recovery of amine and recycle of solvent/diluent(s). Among preferred solvent/diluent(s) that achieve such highly advantageous results are diethyl ketone (3-pentanone), methyl ethyl ketone, methyl isobutyl ketone, and other equivalent polar solvent/diluents. In this connection, it is preferred to use a single organic solvent/diluent in A) of this fourth embodiment, and more preferably the same single organic solvent/diluent is also present in, or constitutes, the solvent/diluent of D) of the same embodiment.

The aqueous mineral acid used in B) of the fourth embodiment is preferably dilute aqueous hydrochloric acid, e.g., in the range of about 1 to about 20 wt % aqueous HCl. However other aqueous acids that can be used are the non-oxidizing aqueous mineral acids including sulfuric acid, sulfurous acid, phosphoric acid, phosphorous acid, hydrobromic acid, hydroiodic acid, and aqueous acids of similar properties and chemical characteristics. The amount of aqueous mineral acid used should be sufficient to form an acidic aqueous phase containing all or substantially all of the amine-hydrohalide in solution, and to form a separate aqueous phase which can readily be separated from the organic phase comprising the polar solvent(s) and the arylolefin or substituted arylolefin. To facilitate the ensuing separation a large excess of the acid should not be used as it would necessitate extra materials handling. Thus use of no more than about 10 mole % excess of dilute aqueous mineral acid is preferred, but more excess acid than this can of course be used, if desired. The temperature and pressure conditions during the conduct of this operation are not critical provided the materials remain in the liquid state. Thus the operation is typically conducted at ambient room temperature and pressure conditions. However elevated temperatures conditions e.g., up to about 100° C. or more, can be used. Also elevated pressures can be used, but ordinarily this is unnecessary. Use of the aqueous mineral acid results in the formation of (i) an aqueous phase containing dissolved amine-hydrohalide and depending on the acid used, other water-soluble amine salt(s) of the mineral acid, and (ii) a liquid organic phase comprising olefinically-substituted aromatic compound and one or more polar organic solvents, and as noted above, if conducted using the preferred materials, the interface between these phases is clean, i.e., it is free of any appreciable rag. Thus the separation of C) is readily accomplished by decantation or draining of one liquid phase from the other liquid phase.

Before conducting step D) of the fourth embodiment, steps B) and C) can be repeated in sequence so as to further reduce the amount of amine left in the organic phase.

It is particularly preferred to conduct Steps A), B), C), and D) of the fourth embodiment in the same reaction vessel as a so-called "one pot" process, wherein appropriate portions of reaction mixtures from ensuing reaction steps conducted in the same reaction vessel are not removed from the reaction vessel—only all or portions of coproduct(s), and/or diluent(s) and/or solvent(s) and/or other unnecessary or unwanted materials, if any, are removed from the reaction vessel after successive reaction steps. And in this particularly preferred embodiment organic solvent/diluent used in D), most preferably is the same organic solvent/diluent used in A) of the fourth embodiment.

The fifth embodiment comprises (A) forming in a reactor, a reaction product composition comprising arylolefin or a substituted arylolefin (e.g., 3-vinylbenzophenone, 6-methoxy-2-vinylnaphthalene or 4-isobutylstyrene, etc.), amine-hydrohalide, and optionally free amine in a liquid polar organic solvent medium by palladium-catalyzed arylation of a 1-olefin (e.g., ethylene) with an aryl halide and/or substituted aryl halide (e.g., 3-bromobenzophenone, 2-bromo-6-methoxynaphthalene or 4-bromoisobutylbenzene, etc.), in a liquid polar organic solvent having a specific gravity less than that of water and a suitably low solubility in water, and containing at least one secondary or tertiary amine that forms a water-soluble hydrohalide salt (most preferably triethylamine) as hydrogen halide acceptor, and (B) mixing with such reaction product composition an aqueous mineral acid (e.g., dilute aqueous HCl), to thereby form (i) a liquid organic phase containing such arylolefin or substituted arylolefin, and (ii) a lower aqueous phase containing dissolved therein the hydrohalide of said secondary or tertiary amine, and, optionally, another acid salt of the secondary or tertiary amine, such that no visually perceptible rag is formed at the interface between said phases when said phases are viewed in a quiescent state, and C) draining said lower aqueous phase from the bottom of the vessel to leave said organic phase therein, thereby enabling a subsequent carbonylation reaction to be performed with said arylolefin or substituted arylolefin in the same reactor. It can be seen that a feature of the fifth embodiment is use in the arylation reaction of a liquid polar organic solvent having a specific gravity less than that of water and a relatively low solubility in water, so that after the treatment with the aqueous mineral acid the aqueous phase is below the organic phase and can be drained off leaving the organic phase with its dissolved arylolefin or substituted arylolefin reactant within the reaction vessel. This in turn enables the arylolefin or substituted arylolefin to be carbonylated in the same reactor without removing the organic phase therefrom. By producing pursuant to this embodiment a rag-free interface between these two liquid phases, this phase separation is greatly facilitated, and loss of the arylolefin or substituted arylolefin reactant during the phase separation is minimized.

Suitable liquid polar organic solvents that have a specific gravity less than that of water, a suitably low solubility in water and the potentiality of forming a rag-free interface include, for example, butyl ethyl ether, tert-butyl ethyl ether, benzyl ethyl ether, ethyl isobutyl ether, ethyl isoamyl ether, dibutyl ether, ethyl hexyl ether, ethyl heptyl ether, 2-butanone, 2-pentanone, 3-pentanone, 3-methyl-2-butanone, 2-hexanone, 3-hexanone, 3-methyl-2-pentanone, 4-methyl-2-pentanone, 2-methyl-3-pentanone, 2-heptanone, 3-heptanone, 4-heptanone, 5-methyl-2-hexanone, 5-methyl-3-hexanone, 2,4-dimethyl-3-pentanone, 2-octanone, 3-octanone, 6-methyl-3-heptanone, and 2-methyl-4-heptanone. The most preferred liquid polar organic solvent for use in this operation is 3-pentanone (diethyl ketone), which has been shown to have the capability of forming a rag-free interface between the two liquid phases.

In all other material respects, the materials and conditions used in the conduct of the fifth embodiment are the same as those used in the fourth embodiment.

As noted above, the sixth embodiment of this invention relates to the production of ketoprofen from a benzoyl halide, especially benzoyl chloride. In this embodiment, the following sequence of reactions is conducted either in one plant facility or in two or more separate plant facilities:

1) Benzoyl chloride is brominated to form m-bromobenzoyl chloride, preferably using either bromine or bromine chloride as the brominating agent.
2) m-Bromobenzoyl chloride is reacted with benzene to form m-bromobenzophenone.
3) m-Bromobenzophenone is converted to m-vinylbenzophenone by palladium-catalyzed arylation of ethylene in a liquid polar organic solvent/diluent (preferably having a specific gravity less than that of water), that contains at least a stoichiometric amount of at least one secondary or tertiary amine (most preferably triethylamine) as hydrogen halide acceptor.
4) Reaction product mixture formed in 3) is contacted with aqueous mineral acid (e.g., aqueous HCl), to thereby form (i) a liquid organic phase containing m-vinylbenzophenone, and (ii) a liquid aqueous phase containing dissolved therein the hydrohalide of the secondary or tertiary amine, and, optionally, another water-soluble acid salt of the secondary or tertiary amine.
5) A separation is effected between the aqueous and organic phases formed in 4).
6) m-Vinylbenzophenone from 5), preferably in the same organic phase as in 5), optionally with an additional makeup quantity of the same solvent/diluent, is subjected to a palladium-catalyzed carbonylation with carbon monoxide in the presence of water or alcohol and hydrochloric acid to form 2-(3-benzoylphenyl) propionic acid (if water was used) or an ester of 2-(3-benzoylphenyl)propionic acid (if an alcohol was used).

In the fourth, fifth and sixth embodiments, workup of the arylation reaction product involves using a dilute aqueous acid washing procedure. In this operation the procedure comprises mixing with at least a portion of the arylation reaction product composition a dilute aqueous acid to thereby form (i) an organic phase containing the arylolefin or substituted arylolefin, and (ii) an acidic aqueous phase containing dissolved amine hydrohalide, and separating at least a portion of these phases from each other. All or at least a portion of the separated organic phase is then suitable as feed to a palladium-catalyzed carbonylation to form arylalkylcarboxylic acid or ester or substituted arylalkylcarboxylic acid or ester in accordance with conditions and procedures described above with reference to the first, second and third embodiments of this invention. Before conducting the carbonylation reaction, an ethereal solvent such as a cyclic ether solvent (tetrahydrofuran, methyltetrahydrofuran, 1,4-dioxane, etc.), can be added to the separated organic phase to enhance the ensuing carbonylation reaction. To accommodate the added ethereal solvent, the separated organic phase may be subjected to a stripping or distillation step to remove some of the polar solvent(s) from the separated organic phase, before adding the ethereal solvent. The stripped polar solvent may be used as recycle solvent in the arylation process.

In greater detail, the arylation reaction produces a reaction mixture comprising olefinically-substituted aromatic compound, amine-hydrohalide and one or more of the polar organic solvents. Pursuant to this invention, an aqueous solution of a non-oxidizing mineral acid such as $H_2SO_3$, $H_2SO_4$, $H_3PO_3$, $H_3PO_4$, HCl, HBr, HI, etc., and most preferably aqueous hydrochloric acid, is mixed with at least a portion (preferably, all) of the reaction mixture to convert free amine into a water-soluble acid salts such as a hydrohalide salt, and to form (I) an acidic aqueous phase containing dissolved acid salt(s) of the amine, and (ii) an organic phase comprising olefinically-substituted aromatic compound, one or more of the polar organic solvents, and in some cases, some residual amine. Although well known to those skilled in the art, it is deemed necessary, or at least prudent, to point out to a non-chemist who may be called upon to read this document that because the acid converts amine to an amine salt in the presence of water, at least a portion of the amine salt may exist in ionic forms while dissolved in the water. However chemists would commonly refer to the solution as containing an amine salt. Thus if and when referring in the specification and/or claims hereof to converting the amine to an amine salt, it is to be understood that this means that the resulting mixture contains the amine and/or amine salt(s) in whatever chemical forms they exist in the environment and under the conditions used.

Of the aqueous mineral acids, aqueous hydrochloric acid is the preferred mineral acid. This acid is widely available at reasonable cost and, when used in the workup procedure, forms two phase liquid systems that have clean, rag-free interfaces.

Whether conducted in stages or all at once, ultimately at least a stoichiometric amount of the mineral acid should be, and in most cases is, employed relative to the amount of excess amine present in the reaction mixture.

As to the concentration of these mineral acid solutions, it is desirable to use solutions that contain the equivalent of at least about 5 weight percent of the acid being used. Saturated or concentrated aqueous acid solutions can be used as long as the resultant amine salt can be dissolved in the aqueous acid, but typically the concentration of the acid solution as mixed with the reaction mixture will be at least slightly less than a concentrated solution. Alternatively, the combination of concentrated acid and water can be introduced into the reaction mixture being subjected to the workup procedure and although not critical, it is usually desirable to add the water before the concentrated acid, and to conduct this operation with stirring or other type of physical agitation. Preferred concentrations of aqueous hydrochloric acid solutions are in the range of about 0.5 to about 5 wt %.

The conditions for the mixing of the mineral acid such as aqueous hydrochloric acid with the arylation reaction mixture are not critical. All that is required is to ensure that these materials are sufficiently well mixed so that intimate contact is established between these materials. Temperatures will typically be in the range of about 20 to about 100° C., but other temperatures may be used. Agitation periods in the range of about 10 to about 30 minutes will normally suffice, but longer periods of up to 60 minutes or more (e.g., 2 hours or more) can be used, if desired.

After mixing, the resulting mixture is allowed or caused to separate into the organic and aqueous liquid phases, usually by allowing the mixture to stand in a quiescent state. Standing periods of one hour or less are usually sufficient. Then the phases are separated from each other, for example by decantation or, more usually, by draining off the lower aqueous layer.

The organic phase may be, and at least in larger scale operations, preferably is again treated at least once more with mineral acid to further reduce the amount of amine remaining in the organic phase. This provides an organic solution consisting essentially of the arylolefin or substituted arylolefin and the organic solvent/diluent(s) used. As noted above in the section headed "Workup of Arylation Product", residual amine if present in excessive amounts in the organic phase after workup can have adverse effects upon the ensuing carbonylation reaction. Thus the comments made above concerning the nature of such adverse effects, the amounts of amine that can be tolerated, and the desirability of performing a few preliminary experiments, are equally applicable here.

The amine can be, and preferably is, recovered from the aqueous solution(s) from the phase separation(s). This is accomplished by mixing together at least a portion of the separated aqueous phase and a strong inorganic base to form free amine and an aqueous solution of inorganic halide. Suitable strong bases include NaOH, KOH, $NH_4OH$, $Na_2O$, $K_2O$, $Ca(OH)_2$, $Na_2CO_3$, $K_2CO_3$, CaO, and other inorganic bases of comparable base strength. This results in the formation of an aqueous phase and an organic phase consisting essentially of the free amine(s). Separation of these phases provides the amine for use as recycle. The amine can be purified by distillation, if necessary.

Preferably, liquid organic makeup solvent/diluent, if any, is mixed with the organic phase after completion of the aqueous acid workup procedure whereby the liquid mixture for carbonylation further comprises at least a portion (preferably, all) of the organic phase from the workup and the makeup solvent/diluent. While various solvent/diluents may be used, the makeup solvent/diluent is preferably composed of the same component(s) as used in the arylation reaction.

The sixth embodiment of this invention is a process preparing ketoprofen from benzoyl chloride as the initial organic reactant. The process involves a sequence of operations which can be conducted at a single plant site or at two or more plant sites. These operations will now be considered seriatim.

Bromination of Benzoyl Chloride

In the first step of this process sequence the benzoyl chloride is converted by bromination to m-bromobenzoyl chloride. This process step is preferably conducted using bromine chloride, although other known brominating agents can be used under appropriate reaction conditions.

When using bromine chloride as the brominating agent, the bromine chloride can be preformed or formed in situ, and the latter is preferred. In accordance with this preferred procedure, benzoyl chloride, bromine and iron powder are charged to a reactor and the reactor contents are cooled to a temperature in the range of about 0 to about 60° C., preferably about 10° C., and chlorine is slowly fed into the reactor whereby bromine chloride is formed in situ. The bromine chloride reacts with the benzoyl chloride to form m-bromobenzoyl chloride (MBBC). Usually the reaction is performed at a temperature the range of about −10 to about 60° C., preferably at about 10° C. for a period in the range of about 1 to about 24 hours, and typically for about one hour after completion of the chlorine feed. The reaction mixture is then stripped with an inert gas, preferably nitrogen, for 1 to 24 hours at a temperature in the range of about 25 to about 120° C., preferably for two to three hours at about 60 to 90° C., followed by further stripping while cooling to ambient room temperature (ca. 25° C.). During the reaction and subsequent stripping operations, the exit gases are passed through suitable scrubbers to remove purged HCl, and unreacted bromine. The major residual byproducts of the bromination are m-chlorobenzoyl chloride, chlorobromobenzoyl chlorides, and dibromobenzoyl chlorides. The crude MBBC can be purified by distillation at reduced pressure, for example at 160° C. and 60 mm Hg pressure.

Friedel-Crafts Acylation of Benzene

MBBC is then reacted with benzene in a Friedel-Crafts acylation reaction in which, preferably, the catalyst is aluminum chloride, but which can be other known Friedel-Crafts catalysts such as gallium trichloride, iron trichloride, aluminum bromide, iron tribromide, antimony pentachloride, antimony tribromide, zirconium tetrachloride, tin tetrachloride and like catalysts. The acylation is typically conducted at one or more temperatures in the range of about 0 to about 80° C., and preferably in the range of about 40 to about 75° C. to produce MBBP. Typically benzene and $AlCl_3$ are charged to the reactor, this mixture is heated to about 40° C., and the MBBC is then fed to the reactor while keeping the temperature within the range of about 40 to about 75° C. The reaction mixture is then held at about 60° C. for about one hour, and the crude MBBP product solution is quenched in water, preferably in a separate vessel at about 40 to about 80° C. The aqueous phase is cut, typically at about 60° C., to remove the catalyst such as aluminum chloride. Following a caustic wash to remove any residual acid, also typically conducted at about 60° C., the benzene is distilled from the mixture and n-heptane or similar paraffinic solvent is added as the crystallization solvent. This solution is filtered and then the MBBP is crystallized, centrifuged, and dried.

The major impurities in the MBBP are benzophenone, chlorobenzophenone (from chlorobenzoyl chloride), chlorobromobenzophenones (from chlorobromobenzoyl chlorides), and dibromobenzophenones (from dibromobenzoyl chlorides). The chlorobromobenzoyl chlorides and the dibromobenzoyl chlorides can be completely removed from the MBBC product prior to the acylation reaction by fractional distillation or can be reduced to easily managed levels by a simple flash of the MBBC overhead. They can also be reduced to acceptable levels by careful control of the crystallization process, although the crystallization yield is reduced. Chlorobenzophenone is actually concentrated during such crystallization. However this impurity is an inert material in the ensuing arylation and carbonylation reactions and is easily removed during ketoprofen purification steps.

Palladium-Catalyzed Arylation of Vinyl Olefin

While other vinyl olefins can be used, it is preferred to use ethylene as the vinyl olefin in this reaction. Thus the reactants in this operation are MBBP produced as above, and ethylene whereby m-vinylbenzophenone (MVBP) is produced. As previously described hereinabove, various palladium catalyst systems, reaction solvent/diluents, and hydrogen halide acceptors can be used in this reaction. Most preferred, however, is to carry out this particular reaction using palladium dichloride (PDC) and neomenthyldiphenylphosphine (NMDP) as the catalyst system, diethyl ketone (DEK) as the solvent/diluent, and triethylamine ($Et_3N$) as HBr acceptor. Typically, the MBBP is dissolved in the DEK and reacted with ethylene at pressures in the range of about 100 to about 1000 psi, preferably in the range of about 300 to about 800 psi, and at temperatures in the range of about 50 to about 150° C., preferably in the range of about 80 to about 120° C., in the presence of excess added $Et_3N$ relative to the moles of MBBP used. Reaction periods in the range of about 2 to about 20 hours are suitable.

Mineral Acid Treatment of Arylation Reaction Mixture and Phase Separation(s)

The byproduct $Et_3N$-hydrobromide and excess $Et_3N$ are removed using a dilute aqueous HCl wash, followed by removal of the bottom aqueous phase. Preferably, the organic phase in the reaction vessel is washed with dilute aqueous HCl a second time followed by the removal of the resultant bottom aqueous HCl phase. These operations can be conducted at various temperatures, but typically are performed at temperatures in the range of about 20 to about 80° C., and at ambient atmospheric pressures.

Palladium-Catalyzed Hydracarbonylation of m-Vinylbenzophenone

The carbonylation reaction is preferably conducted in the same reaction vessel as the arylation, aqueous HCl wash, and phase separation operations. While various palladium catalyst systems and solvents can be used, it is preferred to perform the hydracarbonylation reaction using PDC and NMDP as the catalyst system (copper (II) chloride can also be included, if desired), residual DEK as the solvent/diluent, carbon monoxide as the carbonylating agent, and dilute aqueous HCl as a proton source. Thus, to the organic phase remaining in the reaction vessel after the foregoing phase separation(s) and containing the MVBP are added PDC, NMDP and dilute hydrochloric acid (typically about 5 to about 15% aqueous HCl, and preferably about 10% aqueous HCl). The MBBP or MVBP/PDC/NMDP mole ratio is typically at the 2000/1/6 level, although it can vary from about 100/1/10 to about 4000/1/4. The amount of the aqueous HCl used is in the range equivalent to from about 0.05 to about 0.5 moles of HCl per mole of MVBP. The resulting mixture is allowed to react, typically at about 100 to about 2000 psi CO at 50–150° C., and preferably at pressures in the range of about 500 to about 1500 psi at temperatures in the range of about 70 to about 120° C. to give ketoprofen. Reaction periods in the range of about 2 to about 10 hours are typical.

Workup and Recovery of Ketoprofen

This is an optional, but preferred, step in the reaction sequence. A preferred manner by which this step may be conducted is as follows: The ketoprofen formed as above is be converted to an aqueous solution of the sodium salt of ketoprofen dissolved in water by the addition of caustic and water to the above ketoprofen reaction mixture. The resulting aqueous solution is separated from the organic phase and can be further purified by washing it with toluene. The residual organic phase is predominately DEK containing some neutral impurities, palladium complexes and NMDP, and it is possible to reuse this as solvent and as part or all of the catalyst/solvent charge in an ensuing palladium-catalyzed arylation reaction using MBBP and/or in part in an ensuing palladium-catalyzed carbonylation of MVBP if makeup DEK solvent is required.

In addition to the profen compounds described above, other profen compounds which can be prepared under appropriate conditions by use of this invention to convert the corresponding bromo precursors by reaction with ethylene include protizinic acid, tiaprofenic acid, indoprofen, benoxaprofen, carprofen, pirprofen, pranoprofen, alminoprofen, suprofen and loxoprofen.

The following examples are given to illustrate various embodiments of the fourth, fifth and sixth embodiments of this invention and are not intended as a limitation thereof. Unless otherwise specified all parts and percentages are by weight.

Example 12 illustrates the dilute acid wash workup procedure for separating the arylation product and the secondary or tertiary amine use as the hydrogen halide acceptor in the arylation reaction.

EXAMPLE 12

To a 5 gallon stainless steel magnetically stirred autoclave are added DEK (3296 g), BMN (1502 g, 6.34 mol), NMDP (6.170 g, 19.0 mmol), $PdCl_2$ (0.574 g, 3.2 mmol), and TEA (684 g, 6.76 mol). The reactor is purged with nitrogen and then filled with ethylene and heated to 95° C. The reaction mixture is stirred for 4.5 hours at 95° C. under ethylene pressure (609 to 640 psig) and then cooled to 60° C. and slowly vented. The reactor is emptied yielding a mixture of yellow solids and yellow liquid. A 5000 g portion of this reaction mixture is poured into a 12 L flask fitted with a mechanical stirrer and a bottom outlet. Water (695 g) and 10 wt % aqueous HCl (209 g) are added to the reaction mixture, and the mixture is stirred and warmed to 65° C., and then allowed to stand and settle. The aqueous phase is removed from the yellow organic phase. The organic phase is washed a second time with a mixture of water (250 g) and 10 wt % aqueous HCl at 64° C., and the aqueous phase is separated from the washed organic phase which is composed mainly of MVN and DEK. The washed organic phase is hydracarbonylated as described above, preferably after stripping off some of the DEK and replacing it with THF. The aqueous phases contain triethylamine hydrochloride, from which TEA can be recovered by addition of a strong base such as aqueous NaOH, followed by a phase separation.

EXAMPLE 13

Preparation of Meta-Bromobenzoyl Chloride (MBBC)

The apparatus used for the reaction was a jacketed 1-liter 4-necked round bottom flask with a bottom stopcock, a mechanical stirrer, a chlorine inlet tube (0.25-inch o.d. tubing extending to just above the agitator blade), a thermocouple well, a Friedrich condenser (tap water for cooling) with a nitrogen line connected by a T-junction into the top of the condenser, and a caustic scrubber. To the 1-liter flask was added 421.5 g of benzoyl chloride (3.00 mols), 2.1 g of iron powder (0.038 g-atom), and 264 g bromine (1.65 mols). Over a 4.3 hour period, chlorine (117 g, 1.65 mols) was added to the solution (below the surface of the solution) while stirred at 9–11° C. (the caustic trap had gained about 119 g during the reaction). The reaction mixture was stirred for 1 hour at 10° C. (the caustic trap had gained 128 g total at this point). It was then warmed to about 50° C. and held there for 0.5 hours while sparging the solution with nitrogen to remove the bromine, hydrogen chloride and hydrogen bromide. The solution was allowed to cool to and stir at ambient temperature overnight (16 hours) while continuing to sparge the solution with nitrogen. There was obtained 645 g of greenish-black liquid crude m-bromobenzoyl chloride (crude MBBC) which contained some iron powder. Some iron powder remained in the bottom of the flask. The residual bromine level in the sample was found to be 0.16 wt %.

EXAMPLE 14

Flash Distillation of Crude MBBC

To a 1-liter round bottom flask with a thermocouple well was added 599 g of crude MBBC prepared as in Example 13, and 5.9 g of 1-octadecene (Gulftene 18). The crude MBBC was distilled (simple flash distillation) at 145 to 171° C. (50 mm, pot temperature 162–179° C.) to give 452 g of clear colorless distillate MBBC product (labeled as product) and 143 g of a more viscous black liquid pot residue (labeled as bottoms). Table 2 summarizes the results of analyses of samples of these respective materials. The following designations are used in Table 2:

| | |
|---|---|
| BC | Benzoyl Chloride |
| CBCs | m, p, and o-Chlorobenzoyl Chlorides |
| MBBC | meta-Bromobenzoyl Chloride |
| PBBC | para-Bromobenzoyl Chloride |
| OBBC | ortho-Bromobenzoyl Chloride |
| CBBCs | Chlorobromobenzoyl Chlorides |
| DBBCs | Dibromobenzoyl Chlorides |

TABLE 2

| Stream | | GC Area % analysis | | | | | |
|---|---|---|---|---|---|---|---|
| Stream | Wt (g) | BC | CBCs | MBBC | PBBC | OBBC | CBBCs | DBBCs |
| Crude | 605 | 10.3 | 4.6 | 75.4 | 0.6 | 0.3 | 0.7 | 2.5 |
| Product | 452 | 10.8 | 5.7 | 79.7 | 0.6 | 0.2 | 0.6 | 1.2 |
| Bottoms | 143 | 0.1 | 0.7 | 75.6 | 0.7 | 0.3 | 2.7 | 11.4 |

EXAMPLE 15
Acylation of Benzene Using Flashed MBBC to Form m-Bromobenzophenone (MBBP)

To a 3-liter 4-necked jacketed round bottom flask equipped with a mechanical stirrer, addition funnel, thermocouple well and a Friedrich condenser were added 1104 g of reagent grade benzene (14.1 mols, which contained ca. 350 ppm water) and 343 g anhydrous aluminum chloride powder (2.57 mol). The mixture was warmed to 42° C. and the flashed MBBC product (product from example 14, 435 g) was added over 1 hour at a rate such that the temperature was maintained between 42–62° C. During this time HCl evolution occurs. For one hour the reaction mixture was stirred as its temperature dropped from 62 to 54° C. The reaction mixture was then added to 988 g of water in a 5-liter jacketed round bottom flask (cooled with tap water) at a rate such that the temperature was kept below 70° C. The reaction mixture was stirred for 30 minutes at about 50° C. and then allowed to stand 1 hour at 50° C. The aqueous phase was separated (cut until the black rag layer reached the stopcock). There was obtained 1308 g of aqueous phase. Aqueous 25% caustic (202 g) was added to the reaction mixture and the mixture was stirred for 30 minutes at 44–48° C. The aqueous phase was separated (including the black rag layer which was cut off with the aqueous phase) to give 221 g of mostly aqueous material (steely grey colored with black solids and a small amount of organic phase in it). The organic phase was filtered with a coarse sintered glass funnel to give 1388 g of a benzene solution of bromobenzophenones which contained (by GC wt % with internal standard) 2.8% benzophenone, 2.6% chlorobenzophenones, 0.1% o-bromobenzophenone, 30.7% m-bromobenzophenone, 0.3% p-bromobenzophenone, 0.5% chlorobromobenzophenones, and 0.8% dibromobenzophenones. The material was stripped to dryness on a Rotavapor apparatus (90° C., 2 mm) to give 514 g of orange oil which solidified on standing.

EXAMPLE 16

The procedure of Example 15 is repeated except that the charge of anhydrous aluminum chloride powder is 373 g or 2.80 mol, and in the product workup, a major portion of the benzene is stripped off from the product solution, n-heptane for product crystallization is added, and then the remainder of the benzene is stripped from the mixture by a fractional distillation.

EXAMPLE 17
Crystallization of 3-Bromobenzophenone (MBBP) Made from Flashed MBBC

A 2-liter glycol jacketed resin kettle was equipped with an overhead stirrer. The agitator shaft was fitted with two impellers, a paddle at the bottom and a pitched blade turbine at the top. The reactor was warmed to 75° C. Meanwhile, 508 g molten (temperature: 75° C.) crude MBBP (from example 15) was combined with 1500 g of 75° C. n-heptane in the resin kettle. The mixture was cooled to 50° C. and seeded with 1.0 g of crystalline MBBC. Within 1 hour a thick slurry of very fine crystals had formed. The bath temperature was held at 50° C. for an additional 8 hours. During the course of the 8-hour hold the thick slurry thinned to a coarse slurry of larger crystals that rapidly settled if agitation was interrupted. The pot temperature was then decreased to 9° C. over 7 hours. This was accomplished by lowering the bath temperature 6° C. at 1-hour intervals. The product was then collected by vacuum filtration on a coarse glass frit. The filter cake was washed with 500 g of 10° C. heptane. The wet cake (516 g) was dried in a vacuum oven at 45° C. to yield 412 g of a white powder (GC, wt % analysis: 1.37% benzophenone; 5.39% 3-chlorobenzophenone, 0.02% 2-bromobenzophenone, 91.5% 3-bromobenzophenone; 0.03% total chlorobromobenzophenones; and 0.08% total dibromobenzophenones). The mother liquor, 1338 g, which contained 30.4 g of 3-bromobenzophenone, was disposed of in a burn drum. The wash liquor, 479 g, which contained 10.3 g (by GC, wt % analysis) of 3-bromobenzophenone was recycled as crystallization solvent for the next crystallization. The analyses are summarized in Table 3, wherein the following acronyms are used:

| | |
|---|---|
| BP | Benzophenone |
| OCBP | o-Chlorobenzophenone |
| MCBP | m-Chlorobenzophenone |
| PCBP | p-Chlorobenzophenone |
| OBBP | o-Bromobenzophenone |
| MBBP | m-Bromobenzophenone |
| PBBP | p-Bromobenzophenone |
| CBBPs | Chlorobromobenzophenones |
| DBBPS | Dibromobenzophenones |

TABLE 3

| | Dry Cake | | Mother Liquor | | Wash Liquor | | Mass Balance | |
|---|---|---|---|---|---|---|---|---|
| Component | Wt % | Amt (g) | Wt % | Amt (g) | Wt % | Amt. (g) | Total Amt (g) | Rejection % |
| BP | 1.37 | 5.64 | 2.21 | 29.70 | 0.71 | 3.40 | 38.74 | 85 |
| OCBP | 0.13 | 0.53 | 0.29 | 3.83 | 0.15 | 0.71 | 5.07 | 89 |
| MCBP | 5.39 | 22.2 | 0.14 | 1.87 | 0.13 | 0.62 | 24.7 | 10 |
| PCBP | 0.00 | 0.00 | 0.43 | 5.75 | 0.12 | 0.57 | 6.32 | 100 |
| OBBP | 0.03 | 0.08 | 0.11 | 1.47 | 0.04 | 0.19 | 1.74 | 95 |
| MBBP | 91.5 | 377.0 | 2.27 | 30.37 | 2.15 | 10.29 | 417.7 | N/A |
| PBBP | 0.00 | 0.00 | 0.26 | 3.47 | 0.09 | 0.43 | 0.69 | 100 |
| CBBPs | 0.03 | 0.12 | 0.33 | 4.42 | 0.08 | 0.38 | 5.30 | 98 |
| DBBPs | 0.08 | 0.33 | 0.66 | 8.83 | 0.15 | 0.72 | 9.88 | 97 |

EXAMPLE 18

Charcoal Treatment and Crystallization of 3-Bromobenzophenone (MBBP) from Unflashed m-Bromobenzoyl Chloride 578 Grams of crude m-bromobenzphenone, was dissolved in 1541 g n-heptane at 75° C. To the mixture was added 6 g of activated charcoal (Darco KB, <100 mesh, Aldrich). The charcoal slurry was stirred for 15 min and then filtered through a ½" thick bed of Celite supported on a coarse glass fritted funnel. The solution was crystallized in 2-liter glycol-jacketed resin kettle by cooling to 50° C. and seeding with 1.0 g of crystalline MBBP. This produced a thick slurry of fine crystals which thinned to a coarse slurry of larger crystals after stirring for a period of 8 hr. The stirred slurry was then cooled 6° C. on one hour intervals to a pot temperature of 25° C. The product was collected by vacuum filtration and then washed with 471 g of 10° C. n-heptane. The product was collected and then dried at 40° C. in a vacuum oven to a constant weight of 400 g. The product purity was 94.37 wt % (82% recovery of contained MBBP) and had a Hunter Color YI value of 1.66. The analysis and weights of products and side streams are presented in Table 4.

TABLE 4

| | 400 g Dry Cake | | 1444 g Mother Liquor | | 610 g Wash Liquor | | Mass Balance | |
|---|---|---|---|---|---|---|---|---|
| Component | Wt % | Amt, g | Wt % | Amt, g | Wt % | Amt, g | Total Amt, g | Rejection % |
| BP | 1.22 | 4.88 | 1.69 | 24.4 | 0.88 | 5.36 | 34.64 | 85.9 |
| OCBP | 0.19 | 0.76 | 0.26 | 3.75 | 0.26 | 1.58 | 6.09 | 87.5 |
| MCBP | 2.18 | 8.72 | 0.11 | 1.58 | 0.09 | 0.55 | 10.85 | 19.7 |
| PCBP | 0.0 | 0 | 0.17 | 2.45 | 0.13 | 0.79 | 0.96 | 100 |
| OBBP | 0.03 | 0.12 | 0.30 | 4.33 | 0.09 | 0.55 | 5.0 | 97.6 |
| MBBP | 94.37 | 377.5 | 4.30 | 62.1 | 3.37 | 20.5 | 460 | |
| PBBP | 0.0 | 0 | 0.27 | 3.90 | 0.19 | 1.15 | 5.05 | 100 |
| CBBPs | 0.02 | 0.80 | 0.30 | 4.33 | 0.13 | 0.79 | 5.92 | 98.5 |
| DBBPs | 0.14 | 0.56 | 1.91 | 27.6 | 0.96 | 5.86 | 34.0 | 98.3 |
| Benzene (ppm) | 10.25 | | 23,000 | | | | | |

EXAMPLE 19

Crystallization of 3-Bromobenzophenone (MBBP) from Unflashed m-Bromobenzoyl Chloride Crude m-Bromobenzophenone, 499 g, was dissolved in 1,500 g n-heptane at 75° C. The solution was crystallized in a 2-liter glycol-jacketed resin kettle by cooling to 46° C. and seeding with 1.0 g of crystalline MBBP. This produced a thick slurry of fine crystals which overnight thinned to a coarse slurry of larger crystals. The solution was then cooled 6° C. on one hour intervals to a pot temperature of 18° C. The product was collected by vacuum filtration and washed with 436 g of 18° C. n-heptane. Weights and analyses were as shown in Table 5.

TABLE 5

| | 357 g Dry Cake | | 1514 g Mother Liquor | | 344 g Wash Liquor | | Mass Balance | |
|---|---|---|---|---|---|---|---|---|
| Component | Wt % | Amt (g) | Wt % | Amt (g) | Wt % | Amt (g) | Total Amt (g) | Rejection % |
| BP | 0.96 | 3.42 | 1.78 | 26.95 | 0.50 | 0.17 | 30.5 | 87.8 |
| OCBP | 0.18 | 0.64 | 0.29 | 4.39 | 0.20 | 0.68 | 5.71 | 89 |

TABLE 5-continued

|  | 357 g Dry Cake | | 1514 g Mother Liquor | | 344 g Wash Liquor | | Mass Balance | |
|---|---|---|---|---|---|---|---|---|
| Component | Wt % | Amt (g) | Wt % | Amt (g) | Wt % | Amt (g) | Total Amt (g) | Rejection % |
| MCBP | 3.26 | 11.64 | 0.13 | 1.96 | 0.10 | 0.34 | 13.94 | 16.5 |
| PCBP |  |  | 0.21 | 3.17 |  |  | 3.17 | 100 |
| OBBP | 0.03 | 0.11 | 0.14 | 2.11 | 0.06 | 0.20 | 2.42 | 95 |
| MBBP | 93.0 | 332.0 | 3.27 | 49.5 | 2.57 | 8.84 | 390 | Yield 85% |
| PBBP |  |  | 0.16 | 2.42 | 0.05 | 0.17 | 2.59 | 100 |
| CBBPs | 0.03 | 0.11 | 0.80 | 12.11 | 0.11 | 0.38 | 12.6 | 99 |
| DBBPs | 0.14 | 0.50 | 1.68 | 25.4 | 0.33 | 1.13 | 27.0 | 98 |

Examples 20 and 21 illustrate the synthesis of ketoprofen using an acid workup between the arylation and carbonylation reactions pursuant to the fourth, fifth, and sixth embodiments this invention, and the arylation, acid workup, and carbonylation process sequence of this invention is conducted as a one-pot synthesis. The following acronyms are used in Examples 20 and 21:

| NMDP | Neomenthyldiphenylphosphine |
| DEK | Diethyl ketone |
| BP | Benzophenone |
| MBBP | m-Bromobenzophenone |
| DBBP | Dibromobenzophenone |
| TBBP | Tribromobenzophenone |
| MVBP | m-Vinylbenzophenone |
| DVBP | Divinylbenzophenone |
| TVBP | Trivinylbenzophenone |

EXAMPLE 20

Preparation of m-Vinylbenzophenone

Charge $PdCl_2$ (16.0 mg, 0.0902 mmol, 0.0005 eq), NMDP (176 mg, 0.542 mmol, 0.003 eq), and MBBP (48 g, 0.184 mol, 1.0 eq) to a 300-mL, Hastelloy B autoclave in a drybox. Add $Et_3N$ (21.0 g, 0.208 mol, 1.15 eq) and DEK (90 mL, saturated with water) via syringe. Purge the reactor with ethylene (3×200 psig) and then pressurize with ethylene to 250 psig. Heat the mixture at 95° C. and keep ethylene pressure at 400–450 psig. Cool the reaction mixture to room temperature after complete conversion (8 hours) and release ethylene pressure. Transfer the reaction mixture to a separation funnel and wash the reactor with DEK (20 mL) and HCl (2%, 50 mL). Add the washings and additional HCl (2%, 50 mL) to the separation funnel. Shake well and let it settle for 30 min (pH=1). Phase cut and wash the organic layer with NaCl (10%, 30 mL). The organic layer was concentrated by rotary evaporator at 60–65° C. to about 84 g and the resultant mixture was directly used for the carbonylation reaction below.

Preparation of Ketoprofen

Charge $PdCl_2$ (16.0 mg, 0.0902 mmol, 0.0005 eq), $CuCl_2$ (16.0 mg, 0.119 mmol, 0.00065 eq), and NMDP (176 mg, 0.542 mmol, 0.003 eq), MVBP (around 38 g, 0.184 mol, 1.0 eq) in DEK (about 45 g), THF (45 g), and HCl (10%, 15.5 g, 4.0 eq) to a 300-mL Hastelloy B autoclave. Purge the reactor with CO (3×200 psig) and pressurize with CO to 250 psig. Heat the reaction mixture at 75° C. and keep CO pressure at 350 psig. Cool the reaction mixture to room temperature after complete conversion (4.5 hr) and release CO pressure. Neutralize the mixture with NaOH to pH =7. Strip THF at 200 mm Hg at 80° C. to give the mixture at the bottom of the pot (about 150 g). Add NaOH (25 wt %, 65 g) and $H_2O$ (200 g) and heat the resulting orange solution at 80° C. for 1 hour. Remove the insoluble solid by filtration and wash the light brown solid with warm water (30 g). Strip the DEK by rotary evaporator to about 350 mL. Wash the resulting mixture with toluene (4×100 mL) and acidify the mixture with $H_2SO_4$ (50%, 62 g) to pH<1. Extract the acidified aqueous phase with toluene (150 mL, then 2×100 mL) and wash the combined organic layers with $H_2O$ (2×30 mL). The pH value was 6 in the second wash. Concentrate under reduced pressure to give an orange syrup. It solidified slowly. Remove the rest of the toluene under vacuum at 60° C. to give a yellow solid (88% yield of ketoprofen).

EXAMPLE 21

Preparation of m-Vinylbenzophenone with Acid Workup

Charge MBBP (22.0 g, 0.0843 mol), $Et_3N$ (10.0 g, 0.0988 mol), $H_2O$ (1.8 g), DEK (28.0 g), $PdCl_2$ (7.5 mg, 0.0423 mmol), and NMDP (82 mg, 0.253 mmol) in a 100-mL, Hastelloy C reactor. GC analysis of the particular MBBP used showed BP (0.8 GC area %), MBBP (95.9 GC area %), DBBP (4 peaks, 2.9 GC total area %), and TBBP (3 peaks, 0.3 GC total area %). Seal the reactor and set up in the hood. Purge the reactor with $N_2$ (3×50 psig) and then heat the mixture to 95° C. Pressure the reactor to 450 psig with ethylene and keep ethylene pressure at 400–450 psig. Monitor the reaction by GC. Reaction was complete in 11 hours. GC analysis showed BP (1.4 GC area %), MVBP (89.0 GC area %), dimers (6.4 GC area %) and other heavies (DVBP and TVBP, 3.0 GC area %). Cool the reaction mixture to room temperature and release ethylene pressure. Add HCl (3%, 20 g) to the reactor via syringe and agitate the mixture at 50° C. for 10 minutes. Open the reactor and transfer the reaction mixture to a separation funnel. Settle for 20 minutes and phase cut. The aqueous layer (36.6 g) had a pH value of less than 1. Almost no rag layer was observed. The organic phase (45 g) was used for the carbonylation step. This organic phase theoretically contained 17.5 g MVBP and 27.5 g DEK.

Preparation of ketoprofen

Transfer the reaction mixture obtained from the above last Heck reaction to an autoclave (Hastelloy C, 100-mL). Charge HCl (10%, 7.0 g), $PdCl_2$ (7.5 mg, 0.423 mmol), and NMDP (88.0 mg, 0.271 mmol). Wash the flask with DEK (5.0 g) and transfer the washing to the autoclave (32.5 g DEK total). Seal the reactor and set up in the hood. Purge the reactor with $N_2$ (3×50 psig) and pressurize with CO to 650 psig. Heat the reaction mixture to 80° C. and CO pressure increased to 750 psig at 80° C. Keep the CO pressure at around 680–870 psig and monitor the reaction by GC. The pressure gauge showed the reaction stopped taking CO in about 4 hours. Cool the reaction mixture to room temperature after 4.5 hours and release CO pressure. GC analysis showed BP (1.1 GC area %), MVBP (1.3 GC area %), MBBP (0.3 GC area %), ketoprofen (90.6 GC area %), linear ketoprofen (0.15 GC area %), dimers (4.7 GC area %), and other heavies (2.0 GC area %). Open the reactor and transfer the reaction mixture to a 250-mL, round-bottom flask. Neutralize the reaction mixture with NaOH (25 wt %, 5.2 g) to pH=7. Add NaOH (25 wt %, 15.0 g) and $H_2O$ (27.0 g) and agitate the mixture at 60° C. for 10 minutes. Transfer the mixture to a separation funnel and settle for 15 minutes. Phase cut while hot (45–50° C.) and transfer the organic layer back to the flask. Add NaOH (25 wt %, 5.0 g) and $H_2O$ (5.0 g) and agitate at 60° C. for 10 minutes. Transfer the mixture to the separation funnel and settle for 15 minutes. Phase cut while hot (45–50° C.). Combine the aqueous layers and wash with toluene (3×15. mL). Acidify the aqueous layer with $H_2SO_4$ (75 wt %) to pH<1. Extract the acidified aqueous layer with toluene (30 mL and then 2×15 mL). Wash the combined organic layers successively with saturated aqueous NaCl (7.5 g), $H_2O$ (10 g), saturated aqueous NaCl (7.5 g), and $H_2O$ (10 g). Phase separation was relatively slow. GC analysis showed ketoprofen (99.5 GC area %), linear ketoprofen (0.17 GC area %), and other peaks (0.35 GC area %). Branched to linear ratio was 584:1. Strip toluene under vacuum at 60° C. to give an orange syrup. It solidified upon standing to give a brown solid (18.0 g, 84% yield of ketoprofen).

FURTHER DETAILED DESCRIPTION—
SEVENTH AND EIGHTH EMBODIMENTS

In the seventh embodiment, the process comprises:

A) reacting arylolefin or substituted arylolefin with carbon monoxide and water in the presence of palladium catalyst formed at least from (1) palladium or palladium compound and (2) organophosphine ligand, to form a reaction mass comprising (a) arylalkylcarboxylic acid, or substituted arylalkylcarboxylic acid and (b) one or more residual catalyst species;

B) mixing together at least a portion of such reaction mass and aqueous inorganic base to form (i) an aqueous phase with water-soluble salt of the arylalkylcarboxylic acid or substituted arylalkylcarboxylic acid dissolved therein, and (ii) an organic phase having at least a portion of the residual catalyst species dissolved therein;

C) separating these phases, and recycling at least a portion of the separated phase (ii) to A) for use in performing additional reaction pursuant to A).

Oftentimes in B) of this seventh embodiment there is, in addition to phases (i) and (ii), a solids phase containing a portion of the palladium catalyst values. Preferably, such solids phase is recovered (e.g., by filtration) and if not sufficiently catalytically active for recycle, at least a portion thereof is converted into an active palladium catalyst component for use in subsequent reaction pursuant to A) of this embodiment.

The eighth embodiment of the invention is a process which comprises:

A) reacting aryl halide or substituted aryl halide with 1-olefin in the presence of hydrogen halide acceptor and palladium catalyst formed at least from (1) palladium or palladium compound and (2) organophosphine ligand, to form a reaction mass containing arylolefin or substituted aryl olefin;

B) reacting at least a portion of the arylolefin or substituted arylolefin so formed with carbon monoxide and water in the presence of palladium catalyst formed at least from (1) palladium or palladium compound and (2) organophosphine ligand, to form a reaction mass comprising (a) arylalkylcarboxylic acid or substituted arylalkylcarboxylic acid, and (b) one or more residual catalyst species;

C) mixing together at least a portion of the reaction mass of B) and aqueous base to form (i) an aqueous phase with water-soluble metal salt of the arylalkylcarboxylic acid or substituted arylalkylcarboxylic acid dissolved therein, and (ii) an organic phase having at least a portion of the residual catalyst species dissolved therein;

D) separating these phases, and recycling at least a portion of the separated phase (ii) to A) for use in performing additional reaction pursuant to A) and/or to B) for use in performing additional reaction pursuant to B).

In this eighth embodiment also, there is often present in C) in addition to phases (a) and (b), a solids phase containing a portion of the palladium catalyst values. In such cases it is preferable to recover this solids phase (such as by filtration) and if it is not sufficiently catalytically active for recycle, to convert at least a portion thereof into an active palladium catalyst component for use in subsequent reaction pursuant to A) and/or B) of this embodiment.

It will be seen that in the practice of the seventh and eighth embodiments of this invention the separation between the arylalkylcarboxylic acid or substituted arylalkylcarboxylic acid and the residual catalyst species involves a phase separation (e.g., a phase cut or decantation), and requires no reduced pressure distillation. Moreover, a substantial portion of the catalyst residue is organic-soluble, catalytically active, and highly efficacious when used as catalyst recycle.

Catalyst Composition

It will be understood and appreciated that the actual composition of the catalyst residue used as recycle cannot be specified with exactitude. The residue recovered for recycle contains palladium-containing and phosphorus-containing residues which are catalytically active. Whether these residues are composed of reaction products, chemical compounds, chemical complexes, and/or physical mixtures of two or more substances, or etc., is not presently known with certainty. What is known is that the residues are catalytically active and are suitable for use as catalyst recycle. If and when the residue loses sufficient catalyst activity to be effectively used for recycle, it should be segregated for regeneration of one or more catalyst components or at least reclamation of palladium values whenever possible.

Neutralization of Arylalkylcarboxylic Acid or Substituted Arylalkylcarboxylic Acid and Separation Procedures On completion of the hydracarbonylation reaction (above Step A) of the seventh embodiment; above Step B) of the eighth embodiment), aqueous alkali metal base is mixed with all or at least a portion of the resultant reaction mass. This results in formation of an aqueous solution of the alkali metal salt of the arylalkylcarboxylic acid or substituted arylalkylcarboxylic acid. Concurrently, there is formed a separate organic phase from which the arylalkylcarboxylic acid or substituted arylalkylcarboxylic acid has been removed, thereby leaving two readily separable liquid phases, each containing one of the components to be separated. One such phase is the aqueous phase in which the alkali metal salt of the arylalkylcarboxylic acid or substituted arylalkylcarboxylic acid is dissolved. The other liquid phase is the organic phase in which catalyst residues are dissolved. If desired low boiling solvent or diluent, such as tetrahydrofuran (THF) or etc., can be removed from the reaction mass to form a more concentrated reaction mass before conducting the neutralization with aqueous alkali metal base. A simple distillation can be used for removing such low boiling solvent or diluent.

As noted above, still another phase may exist, namely, a solids phase containing an insoluble portion of the palladium catalyst residues. These solids can be physically separated and recovered by filtration or other suitable means, such as centrifugation. If suitably active, the solids can be recycled for use in the hydracarbonylation reaction. Otherwise, the solids can be subjected to combustion in a furnace to produce an ash from which the palladium content can be recovered and used for preparation of a suitable palladium catalyst component, such as palladium(II) chloride. See in this connection U.S. Pat. No. 5,055,611 which describes a suitable procedure for palladium catalyst regeneration, but which, however, requires reduced pressure distillation to effect the separation between catalyst residues and the carboxylic acid formed in the palladium-catalyzed process.

In many cases the hydracarbonylation reaction forms a reaction mass comprising arylalkylcarboxylic acid or substituted arylalkylcarboxylic acid (e.g., racemic 2-(6-methoxy-2-naphthyl)propionic acid, 2-(3-benzoylphenyl) propionic acid, or 2-(4-isobutylphenyl)propionic acid, etc., and a liquid medium comprising polar organic solvent (preferably ketone or nitrile or mixture thereof), water and/or alcohol, HCl, and preferably at least one ether (e.g., THF, etc.) with a boiling temperature below that of at least one such polar solvent. Also present are catalyst residues and typically some coproducts formed during the reaction.

Pursuant to a preferred workup procedure for producing and isolating the purified arylalkylcarboxylic acid or substituted arylalkylcarboxylic acid from the aqueous phase, the arylalkylcarboxylic acid or substituted arylalkylcarboxylic acid in the reaction mass is converted in situ into a water-soluble inorganic salt of such acid by reaction with an aqueous solution of inorganic base (neutralization step). In addition, when the reaction product composition contains (i) at least one low boiling ether (e.g., THF, etc.) and/or (ii) at least one low boiling polar solvent, where either or both such low boiling materials boil(s) below the boiling temperature of at least one polar solvent contained in the reaction mass, some or all of such low boiling materials are distilled from the reaction product composition (distillation step). If the reactor overheads are susceptible to attack by aqueous HCl, and HCl is present in the reaction mass, the neutralization step should precede or at least be conducted concurrently with the distillation step. On the other hand, if the reactor overheads are formed from acid-resistant materials of construction, the distillation step can precede and/or follow and/or be conducted concurrently with the neutralization step; HCl in the mixture will not cause excessive corrosion of the reactor overheads even if the distillation precedes the neutralization. In whatever sequence the neutralization step and the distillation step are conducted, a mixture of residual organic phase and an aqueous phase containing dissolved inorganic salt of the arylalkylcarboxylic acid or substituted arylalkylcarboxylic acid remain in the reactor as a distillation residue (distilland or pot residue). These phases are separated from each other. The aqueous phase is then subjected to a distillation, preferably at or near atmospheric pressure, to remove residual organic impurities such as THF. At this point it is desirable to ensure that the residual aqueous phase has a concentration in the range of about 10 and about 35 wt % of dissolved inorganic salt of the arylalkylcarboxylic acid or substituted arylalkylcarboxylic acid and where necessary, adjusting the concentration of the aqueous phase to about 10 and about 35 wt % solution by removal or addition of water. The aqueous solution is then washed (extracted) with substantially non-polar liquid organic solvent (preferably aromatic hydrocarbon solvent, such as toluene or xylene), preferably at least twice. The free arylalkylcarboxylic acid or substituted arylalkylcarboxylic acid is then produced by mixing non-oxidizing mineral acid (e.g., sulfuric acid) with the aqueous phase in the presence of substantially non-polar liquid solvent to form (i) an organic phase composed of a solution of arylalkylcarboxylic acid or substituted arylalkylcarboxylic acid in substantially non-polar liquid solvent and (ii) an aqueous phase. After separating these phases from each other, the arylalkylcarboxylic acid or substituted arylalkylcarboxylic acid is crystallized from the substantially non-polar liquid solvent.

The aqueous solution of inorganic base used in the above neutralization step is preferably a 10 to 40 wt % solution of NaOH or KOH. However other inorganic bases that can be used include $Na_2O$, $K_2O$, $Ca(OH)_2$, $CaO$, $Na_2CO_3$, $K_2CO_3$, and other inorganic bases of similar basicity. Such solutions are used in an amount at least sufficient to neutralize the arylalkylcarboxylic acid or substituted arylalkylcarboxylic acid and the HCl present in the reaction mass.

When the carbonylation reaction is conducted using an alcohol so that an ester of the arylalkylcarboxylic acid or substituted arylalkylcarboxylic acid is present in the reaction product composition, it is preferred to saponify the ester in situ by mixing a concentrated aqueous solution of a strong inorganic base such as NaOH or KOH with the reaction product composition and applying sufficient heat (e.g., heating to a temperature in the range of up to about 80° C.) to form the inorganic salt of the arylalkylcarboxylic acid or substituted arylalkylcarboxylic acid. Then the workup procedure for the carbonylation product as described above is carried out.

The low boiling materials recovered in the initial distillation step are preferably recycled for use in the hydracarbonylation reaction.

Reaction of Arylhalide or Substituted Aryl Halide with 1-Olefin

In the embodiments of this invention wherein the arylolefin or substituted arylolefin is prepared, converted to arylalkylcarboxylic acid or substituted arylalkylcarboxylic acid, and then subjected to the forgoing catalyst separation and recycle steps, the preferred process step for producing the arylolefin or substituted arylolefin comprises reacting aryl halide or substituted aryl halide with 1-olefin in the presence of hydrogen halide acceptor and palladium catalyst formed at least from (1) palladium or palladium compound and (2) organophosphine ligand. Since this reaction involves the formation of arylolefin or substituted arylolefin, the reaction can be referred to either as the arylation reaction or the vinylation reaction. For convenience, the reaction is referred to herein as the arylation reaction. The reaction mass formed in the arylation reaction thus contains the desired arylolefin or substituted arylolefin intermediate and as noted above, by reacting at least a portion of the arylolefin or substituted arylolefin so formed with carbon monoxide and water in the presence of the above-described palladium catalyst, the arylalkylcarboxylic acid or substituted arylalkylcarboxylic acid is formed in the hydracarbonylation reaction (or via the carbonylation reaction in the presence of alcohol, followed by saponification of the resulting arylalkylcarboxylic acid ester or substituted arylalkylcarboxylic acid ester).

In conducting this embodiment, the arylolefin or substituted arylolefin formed by the reaction can be separated from the remainder of the reaction mass from the arylation reaction, if desired. However, such a separation is not necessary. Instead, it is preferred to leave the arylolefin or substituted arylolefin in the reaction mass and subject at least a portion (usually, all) of the arylation reaction mass to the hydracarbonylation reaction. If the reaction mass contains suitably volatile components, such as excess low-boiling amine-type hydrogen halide acceptor and/or volatile solvent or diluent, such can be removed prior to conducting the hydracarbonylation by subjecting all or part of the arylation reaction mass to a preliminary flash or simple distillation.

Example 22 is illustrative of the of the seventh and eighth embodiments of the present invention.

EXAMPLE 22

Part A

A reaction mass containing racemic 2-(6-methoxy-2-naphthyl)propionic acid (MNPA) was formed by hydracarbonylation of 6-methoxy-2-vinylnaphthalene (MVN) with carbon monoxide in a tetrahydrofuran-diethyl ketone (THF-DEK) solvent mixture to which had been added $PdCl_2$, neomenthyldiphenylphosphine (NMDP) and aqueous HCl. At the end of the reaction, the reaction mass was treated with aqueous NaOH solution to neutralize the HCl, and the THF was stripped from the resultant mixture. The content of crude MNPA in the mixture was converted to the sodium salt of MNPA by adding to the mixture and reacting the MNPA therein with aqueous NaOH solution. A two-phase liquid system was thus formed. After removing the aqueous phase containing the sodium salt of MNPA, the organic phase, containing the catalyst residues and other neutral by-products from the hydracarbonylation, was then used in another hydracarbonylation run to determine whether the catalyst residues therein could be used as a catalyst source in this ensuing hydracarbonylation, and thus ascertain the recyclability of the ligand. Following is the procedure used in this ensuing hydracarbonylation.

Part B

A 1-liter Hastelloy B Parr reactor was charged with MVN (133.8 g, 96.4%, 0.7 mol), $PdCl_2$ (0.062 g, 0.00035 mol), 10 wt % aqueous HCl (60.5 g), and a portion of the organic phase cut from the hydracarbonylation run of Part A above (414 g). The reaction was carried out at 70° C. and 330–350 psig carbon monoxide pressure. Samples were removed at intervals and analyzed by GC for completion of reaction. The MVN conversions were 68.3%, 97.5%, and 98.6% after 4.5 hours, 6 hours, and 7 hours, respectively. The yield of racemic 2-(6-methoxy-2-naphthyl)propionic acid was 93.3%.

FURTHER DETAILED DESCRIPTION—NINTH AND TENTH EMBODIMENTS

In the ninth embodiment the process comprises:

a) conducting a palladium-catalyzed arylation of an olefin (most preferably ethylene), with aryl halide and/or substituted aryl halide (preferably 4-isobutyl-1-bromobenzene, m-bromobenzophenone, or 2-bromo-6-methoxynaphthalene), in a liquid medium formed from (i) at least one liquid dialkyl ketone solvent/diluent having 6 carbon atoms in the molecule (most preferably methyl isobutyl ketone), and (ii) at least one secondary or tertiary amine that boils below the boiling temperature of the ketone solvent/diluent (most preferably triethylamine), to form a reaction mixture comprising olefinically-substituted aromatic compound (preferably where the olefinic substituent is a vinyl or substituted vinyl substituent, and most preferably where the compound is 4-isobutylstyrene, m-vinylbenzophenone, or 6-methoxy-2-vinylnaphthalene), amine-hydrohalide and the ketone solvent/diluent;

b) recovering from said reaction mixture a solution composed principally of the olefinically-substituted aromatic compound in the ketone solvent/diluent; and c) conducting a palladium-catalyzed carbonylation of at least a portion of said olefinically-substituted aromatic compound with carbon monoxide and water and/or alcohol in said ketone solvent/diluent to produce arylalkylcarboxylic acid and/or substituted arylalkylcarboxylic acid or, if alcohol was present, arylalkylcarboxylic acid ester and/or substituted arylalkylcarboxylic acid ester.

The materials used in the palladium-catalyzed arylation of an olefin have been described above and need no repetition here, except to point out that the ketone solvent/diluent used in steps a) and c) is the same liquid ketone or liquid mixture of ketones having 6 carbon atoms in the molecule. It is, of course possible, and indeed it is preferred, to add make up or additional ketone of the same composition to the reaction mixture of step c). Examples of such ketones (together with their approximate boiling points) include butyl methyl ketone (2-hexanone; 127° C.), ethyl propyl ketone (3-hexanone; 123° C.), ethyl isopropyl ketone (2-methyl-3-pentanone; 113° C.), sec-butyl methyl ketone (3-methyl-2-pentanone; 118° C.), tert-butyl methyl ketone (3,3-dimethyl-2-butanone; 106° C.), and isobutyl methyl ketone, commonly called methyl isobutyl ketone or MIBK (4-methyl-2-pentanone; 118° C.). Mixtures of two or more such ketones can be used. Methyl isobutyl ketone is the preferred ketone solvent/diluent.

As noted above, the actual catalytic species in the arylation reaction of step a) may, and apparently does, involve participation of the olefin, and that the actual catalytic species in the carbonylation reaction in c) may involve, in part, interaction between the palladium component and the olefinically-substituted aromatic compound. However this invention is not intended to be limited to, nor should it be construed as being limited to, any particular molecular structure of the actual catalytic species of the arylation and the carbonylation reactions. By using the materials referred to as the components or ingredients for the reactions, the catalyst, whatever its structure or composition, performs in the intended fashion so that the intended chemical reaction takes place to produce the intended product or products.

It will be recalled that the tenth embodiment of this invention relates to a process which comprises:

a) feeding into a reaction vessel a solution of an olefinically-substituted aromatic compound (preferably where the olefinic substituent is a vinyl or substituted vinyl group, and most preferably where the compound is 4-isobutylstyrene, m-vinylbenzophenone, or 6-methoxy-2-vinylnaphthalene) in an organic solvent (preferably a liquid ketone solvent, more preferably at least one liquid dialkyl ketone solvent/diluent having 6 carbon atoms in the molecule, and most preferably methyl isobutyl ketone), containing a carbonylation mixture formed from ingredients which initially comprised aqueous hydrochloric acid, organic solvent corresponding to the organic solvent in the feed, a palladium catalyst, and a suitable trihydrocarbylphosphine (preferably a cycloalkyldiarylphosphine, and most preferably neomenthyldiphenylphosphine), and optionally an alcohol;

b) heating the contents of the reactor and charging carbon monoxide into the reactor under pressure such that carbonylation of the olefinically-substituted aromatic compound occurs to thereby form arylalkylcarboxylic acid or substituted arylalkylcarboxylic acid, or if alcohol is present, to form arylalkylcarboxylic acid ester or substituted arylalkylcarboxylic acid ester.

Since the materials used in the carbonylation reactions of this invention have been described above, further repetition here would serve no useful purpose.

Likewise general reaction conditions described above can be used in the practice of the ninth and tenth embodiments.

However at least in the synthesis of racemic 2-(6-methoxy-2-naphthyl)propionic acid or an ester thereof, it is preferred to utilize a special set of reaction conditions and modes of operation in the ninth and tenth embodiments in order to achieve the most advantageous results made possible pursuant to this invention.

Thus to achieve the best results in conducting step a) of the ninth embodiment, the arylation of ethylene in MIBK to produce 6-methoxy-2-vinylnaphthalene (MVN) is preferably conducted by including in the initial reaction mixture a reaction-promoting amount of water in the range of about 1 to about 2 wt %, more desirably in the range of about 1.5 to about 1.8 wt % (e.g., 1.7 wt %) based on the total weight of the 2-bromo-6-methoxynaphthalene (BMN), MIBK, triethylamine, and water initially present in the reaction vessel. The preferred reaction temperature is in the range of about 95° to about 100° C., most preferably about 100° C.

As to the carbonylation reaction used in the ninth and tenth embodiments, the special conditions for achieving the best results in the carbonylation reaction when converting MVN to racemic 2-(6-methoxy-2-naphthyl)propionic acid will now be described in connection with the conduct of a hydracarbonylation reaction. Suitable adjustments can be made if it is desired to conduct the carbonylation as an alkoxacarbonylation reaction using an alcohol in lieu of water.

As noted in the description of the first, second and third embodiments of this invention, very desirable results are obtained by use of a two-solvent system (i.e., a combination of two different kinds of solvents, such as an ether and a ketone) in the hydracarbonylation reaction. Thus as can be seen for instance from Example 1 above, one such desirable way of operating is to use a ketone such as diethyl ketone (DEK) in the arylation reaction and a solvent pair, tetrahydrofuran (THF) and DEK in the carbonylation reaction. Pursuant to the ninth embodiment a particular solvent, viz., at least one liquid $C_6$ ketone (most preferably 4-methyl-2-pentanone, MIBK), is used in both the arylation and carbonylation reactions, while making possible achievement of excellent results in both reactions. Likewise in the tenth embodiment at least one liquid $C_6$ ketone (most preferably MIBK), is used with excellent results being achievable in the process.

Among the advantages made possible by use of a single solvent such as MIBK as compared to DEK and THF are: lower solvent cost, increased product yield, elimination of need for a column to separate THF and DEK, reduction in the number of storage tanks needed for solvent storage, elimination of cross-contamination of THF with DEK, simplification of reaction mass work-ups, increase in plant capacity, and simplified plant operation resulting in more consistent operation.

In achieving these advantages, instead of conducting the carbonylation as a batch reaction, it has been found possible to successfully operate the process on a semi-continuous basis wherein a solution of 6-methoxy-2-vinylnaphthalene (MVN) in MIBK is co-fed with carbon monoxide to an autoclave containing a heel of HCl (aq), $PdCl_2$, NMDP, and MIBK. The aqueous HCl is preferably a 5 to 15% solution, and most preferably is a 10% solution. Preferably the temperature of the reactor contents is kept in the range of about 70 to about 100° C., preferably in the range of about 80 to about 90° C., and most preferably at about 85° C. Additionally, by starving the reaction of MVN, acid-catalyzed impurities are not only kept in check but are actually decreased as compared to a typical THF/DEK batch process. Thus a relatively dilute solution of MVN in MIBK (e.g., in the range of about 15 to about 30 wt %, and most preferably about 24 wt %) is fed to the reactor. The co-feed of carbon monoxide is conducted at a rate sufficient to maintain the pressure in the reactor within the range of about 300 to about 1000 psig, and preferably in the range of about 300 to about 500 psig. Most preferably this reaction is performed at about 350 psig with a reaction temperature of about 85° C.

With a solution of about 24 wt % of MVN in MIBK, excellent results are achieved using a constant feed rate of about 270 mL of such solution per minute to a heel containing MIBK, 10% aq. HCl, $PdCl_2$ and neomenthyldiphenylphosphine (NMDP) at 70° C./~200 psig CO. Once the reaction temperature reaches 85° C., the reactor is pressurized to 350 psig CO while feeding is in progress. After all MVN/MIBK has been fed at 85° C./350 psig CO, it is desirable to allow the reaction to ride for an additional ~30 minutes at 85° C./350 psig CO to assure that all residual MVN is converted to racemic naproxen.

In the production of racemic naproxen wherein the processes of the ninth and tenth embodiments comprising arylation of ethylene with BMN to form MVN and hydracarbonylation of MVN with CO to form racemic 2-(6-methoxy-2-naphthyl)propionic acid are utilized, the following sequence of plant operations is typically used:

Arylation Reaction and Workup

Arylation of ethylene to form MVN

Filtration of crude MVN-product

Phase separation

Organic phase cut

Distillation of amine (e.g., triethylamine) from organic phase

Carbonylation Reaction and Workup

Hydracarbonylation of MVN to form racemic 2-(6-methoxy-2-naphthyl)propionic acid (MNPA)

Neutralization

Basification of MNPA to form sodium salt of MNPA

Phase separation

Aqueous phase cut

Solvent distillation from aqueous phase

Acidification & crystallization of sodium salt of MNPA

Toluene wash

Acidification

Water wash

Crystallization of racemic naproxen from toluene

In a series of laboratory runs conducted pursuant to this invention, a comparison was made between a two-solvent batch process using DEK as the solvent/diluent in the arylation of ethylene with BMN to form MVN, and a mixture of DEK and THF as the solvent/diluent in the hydracarbonylation of MVN to form racemic MNPA. The arylation reactions were performed in a one-liter stainless steel autoclave, and the hydracarbonylations were performed in a one-liter Hastelloy B autoclave. In both the DEK/THF runs and the MIBK runs all charges, phase cuts, and distillations were performed under preferred conditions. A summary of the reaction results is given in Table 6.

TABLE 6

|  | DEK/THF | MIBK |
|---|---|---|
| Overall yield based on weight of dried racemic MNPA | 72.8%(avg.) | 79.3%(avg.) |
| Accountability of methoxy naphthalene species | 89.1% (avg) | 91.8%(avg.) |
| Yield normalized to 100% accountability | 81.7% | 86.4% |
| Purity of Crystallized racemic MNPA | 99.6% | 99.7% |

In this series of laboratory runs, three arylation runs to form MVN were performed in DEK and three such arylation runs were conducted in MIBK, all pursuant to this invention. Reaction conditions and results of these six runs are summarized in Tables 7, 8, and 9. Table 7 relates to the reaction, filtration and phase cut procedures used. In each run of Table 7 the weight ratio of BMN:Pd:NMDP was 2000:1:6, and after completion of the sodium hydroxide addition, the reaction mixture was maintained at 55° C. for one hour. Table 8 refers to the analytical results on the crude reaction product and the conditions employed for removing residual triethylamine. The distillation for all reactions was performed under vacuum (320–190 mm Hg) using 10 plates to assure acceptable separation of the amine from DEK or MIBK. By removing solvents under vacuum and thus at lower temperatures oligomerization of MVN was avoided. Table 9 describes the composition of the final MVN product prior to being carbonylated.

TABLE 7

|  | DEK 4 | DEK 5 | DEK 7 | MIBK 2 | MIBK 3 | MIBK 5 |
|---|---|---|---|---|---|---|
| Reaction |  |  |  |  |  |  |
| BMN, g | 130.1 | 130.0 | 130.0 | 130.1 | 130.0 | 130.1 |
| $PdCl_2$, g | 0.05 | 0.05 | 0.05 | 0.05 | 0.05 | 0.05 |
| NMDP, g | 0.53 | 0.54 | 0.54 | 0.54 | 0.54 | 0.54 |
| TEA, g | 61.2 | 61.5 | 61.4 | 70.1 | 70.4 | 70.0 |
| DEK, g | 336 | 337 | 336 | N/A | N/A | N/A |
| % $H_2O$ | 2.0 | 2.0 | 2.1 |  |  |  |
| MIBK*, g | N/A | N/A | N/A | 336 | 336 | 336 |
| $H_2O$, g | 12.4 | 12.3 | 11.6 | 0.00 | 3.7 | 0.3 |
| NaOH, (25%), g | 105 | 105 | 105 | 105 | 106 | 107 |
| Ethylene, psig | 450 | 450 | 450 | 450 | 450 | 450 |
| $H_2O$ in solvents, g | 6.6 | 6.6 | 7.0 | 9.3 | 5.4 | 8.9 |
| % $H_2O$** | 3.5 | 3.5 | 3.5 | 1.7 | 1.7 | 1.7 |
| Reaction temp., C. | 95 | 95 | 95 | 100 | 100 | 100 |
| Reaction time, min | 175 | 200 | 175 | 160 | 149 | 180 |
| Ride time, min. | 50 | 50 | 45 | 45 | 45 | 45 |
| Filtration |  |  |  |  |  |  |
| DEK or MIBK (filter cake wash, g) | 31 | 99 | 116 | 93 | 54 | 54 |
| Filter cake wt. (wet, g) | 21 | 23 | 24 | 14 | 13 | 16 |
| Phase Cut (PC) |  |  |  |  |  |  |
| PC temp., C. | 60 | 60 | 60 | 65 | 65 | 65 |
| Solvent flush, g | 28.4 | 0 | 0 | 0 | 0 | 0 |
| Aqueous phase cut, g | 113 | 141 | 168 | 151 | 174 | 140 |
| Organic phase cut, g | 556 | 516 | 560 | 546 | 527 | 525 |
| Organic wt. after PC/filtration, g | 545 | 516 | 560 | 546 | 527 | 525 |
| Organic sample taken, g | 4.4 | 6.5 | 7.6 | 6.9 | 7.6 | 8.1 |
| Grams MVN removed | 0.78 | 1.21 | 1.28 | 1.20 | 1.28 | 1.46 |
| mmoles MVN removed | 4.3 | 6.6 | 6.9 | 6.5 | 7.0 | 7.4 |

*Water content: 0.025%
**Relative to BMN, solvent & TEA

TABLE 8

|  | DEK 4 | DEK 5 | DEK 7 | MIBK 2 | MIBK 3 | MIBK 5 |
|---|---|---|---|---|---|---|
| Analytical on Crude Product |  |  |  |  |  |  |
| BMN, % | 0.06 | 0.05 | 0.02 | 0.003 | 0.002 | 0 |
| HVN, % | 0.08 | 0.10 | 0.12 | 0.07 | 0.07 | 0.03 |
| Dimer, % | 0.06 | 0.06 | 0.06 | 0.06 | 0.06 | 0.06 |
| MVN, % | 17.8 | 18.6 | 16.8 | 17.4 | 16.7 | 18.0 |
| MVN yield, % | 98.0 | 95.2 | 93.0 | 94.0 | 87.1 | 93.6 |
| Distillation |  |  |  |  |  |  |
| Distillation temp. (bottoms, C.) | 89–112 | 50–88 | 52–80 | 69–83 | 69–83 | 69–83 |
| Wt. Of distillate, g | 296 | 356 | 280 | 187 | 249 | 278 |
| Solvent trapped |  | 15 | 162 | 53 | 3 | 14 |
| % DEK in distillate | 77 | 86 | 95 | N/A | N/A | N/A |
| % MIBK in distillate | N/A | N/A | N/A | 88 | 73 | 78 |

TABLE 8-continued

|  | DEK 4 | DEK 5 | DEK 7 | MIBK 2 | MIBK 3 | MIBK 5 |
|---|---|---|---|---|---|---|
| % TEA in distillate | 22 | 13 | 5 | 12 | 27 | 22 |
| % THF in distillate | 0.6 | 0.3 | 0.2 | N/A | N/A | N/A |

TABLE 9

|  | DEK 4 | DEK 5 | DEK 7 | MIBK 2 | MIBK 3 | MIBK 5 |
|---|---|---|---|---|---|---|
| Final Product |  |  |  |  |  |  |
| Product mass, g | 419 | 358 | 346 | 364 | 340 | 352 |
| Analytical on Final Product |  |  |  |  |  |  |
| THF:DEK ratio | 60:40 | 83:17 | 74:26 | N/A | N/A | N/A |
| BMN, % | 0.01 | 0.01 | 0.04 | 0.004 | 0.004 | 0 |
| HVN, % | 0.16 | 0.19 | 0.16 | 0.09 | 0.09 | 0.05 |
| Dimer, % | 0.08 | 0.09 | 0.09 | 0.09 | 0.09 | 0.09 |
| MVN, % | 21.3 | 25.2 | 23.8 | 24.5 | 24.7 | 24.8 |
| MVN yield, % | 91.1 | 92.8 | 85.1 | 90.8 | 85.8 | 89.3 |

Table 10 summarizes the conditions used for the hydracarbonylation of MVN in each of these six laboratory runs. To avoid potential clogging of the feed lines and pump, all MVN/MIBK solutions were filtered prior to cofeeding; furthermore, all lines were heat traced to the carbonylation reactor. After the reaction was complete an organic phase cut was performed to acquire a weight and a sample of the crude organic phase to calculate reaction yields. These two phases were then recombined to proceed with the work-up procedure.

TABLE 10

|  | DEK 4 | DEK 5 | DEK 7 | MIBK 2 | MIBK 3 | MIBK 5 |
|---|---|---|---|---|---|---|
| Heel Content |  |  |  |  |  |  |
| MVN, g | 418 | 395 | 344 | N/A | N/A | N/A |
| Aqueous HCl, g | 36 | 31 | 36 | 51 | 51 | 51 |
| MVN:HCl | 22:1 | 21:1 | 21:1 | N/A | N/A | N/A |
| PdCl$_2$, g | 0.05 | 0.05 | 0.05 | 0.05 | 0.05 | 0.06 |
| NMDP, g | 0.71 | 0.72 | 0.66 | 0.86 | 0.85 | 1.0 |
| MIBK, g | N/A | N/A | N/A | 31 | 31 | 31 |
| Feed |  |  |  |  |  |  |
| MVN, g | N/A | N/A | N/A | 355 | 332 | 342 |
| % MVN | N/A | N/A | N/A | 25 | 25 | 25 |
| % H$_2$O | N/A | N/A | N/A | 0.05 | 0.07 | 0.06 |
| Total feed volume, mL | N/A | N/A | N/A | ca.450 | ca.420 | ca.460 |
| Solvent Flush, g | N/A | N/A | N/A | 5 | 5 | 5 |
| Conditions |  |  |  |  |  |  |
| CO, psig | 340–360 | 340–360 | 340–360 | 340–360 | 340–360 | 340–360 |
| MVN feed rate, mL/min. | N/A | N/A | N/A | 1.8 | 1.4 | 1.8 |
| Reaction time & temp., min. @ degrees C. | 175 @ 70 110 @ 80 | 175 @ 70 110 @ 80 | 175 @ 70 90 @ 80 | 255 @ 85 | 300 @ 85 | 260 @ 85 |
| Ride time & temp., min. @ degrees C. | 60 @ 80 | 60 @ 80 | 60 @ 80 | 30 @ 85 | 45 @ 85 | 45 @ 85 |
| Phase Cut |  |  |  |  |  |  |
| Organic phase cut, g | 428 | 397 | 358 | 413 | 397 | 439 |
| Aqueous phase cut, g | 21 | 23 | 17 | 27 | 27 | 28 |

Analytical results and neutralization procedures on the crude reaction product are given in Table 11.

TABLE 11

|  | DEK 4 | DEK 5 | DEK 7 | MIBK 2 | MIBK 3 | MIBK 5 |
|---|---|---|---|---|---|---|
| Analytical on Carbonylation Product |  |  |  |  |  |  |
| MNPA, % in organic phase cut of | 21.6 | 23.0 | 26.1 | 26.2 | 24.1 | 22.1 |

TABLE 11-continued

|  | DEK 4 | DEK 5 | DEK 7 | MIBK 2 | MIBK 3 | MIBK 5 |
|---|---|---|---|---|---|---|
| Table 10 | | | | | | |
| % Total impurities in organic phase cut of Table 10, solvent free basis | 10.0 | 12.8 | 13.1 | 13.7 | 9.7 | 8.9 |
| MNPA yield, % | 82.9 | 81.5 | 91.3 | 99.5 | 93.4 | 91.4 |
| Neutralization | | | | | | |
| 25% NaOH addition, g | 24.3 | 20.4 | 20.1 | 113 | 105 | 105 |
| First water addition, g | N/A | N/A | N/A | 86 | 29 | 30 |
| First aqueous phase cut, g | N/A | N/A | N/A | 364 | 247 | 272 |
| Second water addition, g | N/A | N/A | N/A | 51 | 102 | 109 |
| Second 25% NaOH addition, g | N/A | N/A | N/A | 6 | 6 | 7 |

Table 12 describes the work-up of crude racemic 2-(6-methoxy-2-naphthyl)propionic acid (MNPA) to the sodium salt of racemic 2-(6-methoxy-2-naphthyl)propionic acid (NaMNPA). The work-up for the MIBK reactions was simplified in that only one distillation was necessary; also, by having a larger organic phase after caustic addition it appears that more impurities are removed from the aqueous sodium naproxen phase. Carbonylation yields were acquired by performing both HPLC and titration analyses on the sodium salt of racemic 2-(6-methoxy-2-naphthyl)propionic acid.

(through feeding) to the heel can have a significant effect in ensuring both rapid and complete conversion of MVN during the feed. Thus with a heel consisting of 10% aqueous HCl, $PdCl_2$, and NMDP, stirring for 20 minutes at 85° C./350 psig CO before the feeding of MVN/MIBK solution was initiated, a 60% MVN conversion was observed. On the other hand, if the MVN/MIBK solution was fed to the heel right after the desired reaction temperature/CO pressure of 85° C./350 psig was reached, a >99% MVN conversion was observed. When MIBK was included in the heel containing 10% aqueous HCl, $PdCl_2$ and NMDP and the heel was

TABLE 12

|  | DEK 4 | DEK 5 | DEK 7 | MIBK 2 | MIBK 3 | MIBK 5 |
|---|---|---|---|---|---|---|
| Distillation | | | | | | |
| Wt. of distillate, g | 159 | 151 | 134 | N/A | N/A | N/A |
| 25% NaOH addition, g | 86 | 87 | 152 | N/A | N/A | N/A |
| Cook time & temp., min. @ degrees C. | 60 @ 75 | 60 @ 75 | 60 @ 75 | N/A | N/A | N/A |
| Water dissolution, g | 144 | 139 | 365 | N/A | N/A | N/A |
| Settling time, min. | 60 | 60 | 60 | N/A | N/A | N/A |
| NaMNPA Phase Cut & Distillation | | | | | | |
| Organic phase cut, g | 82 | 50 | 40 | 250 | 226 | 264 |
| Aqueous phase cut, g | 444 | 448 | 789 | 432 | 432 | 437 |
| Phase cut temperature, C. | 60 | 60 | 60 | 75 | 75 | 75 |
| Distillation temperature (bottom, C.) | 87–107 | 87–107 | 87–106 | 94–104 | 94–104 | 94–104 |
| Water added during filtration, g | 191 | 162 | 35 | 196 | 161 | 189 |
| Wt. of wet cake, g | 8.9 | 14.5 | 2.8 | 8.8 | 9.2 | 11.8 |
| Wt. of aqueous NaMNPA, g | 448 | 405 | 674 | 500 | 487 | 485 |
| Final Product Anal., HPLC Method | | | | | | |
| % NaMNPA in above aqueous phase cut | 22.9 | 23.0 | 13.7 | 20.4 | 21.2 | 21.2 |
| % Total impurities in above aqueous phase cut | 2.9 | 4.9 | 4.4 | 3.5 | 3.6 | 2.7 |
| Final Product Analytical, Titration Method | | | | | | |
| % NaMNPA in above aqueous phase cut | 22.9 | 24.8 | 14.5 | 20.1 | 21.1 | 21.9 |
| Carbonylation yield, % | 84.6 | 82.0 | 87.2 | 83.5 | 90.9 | 91.1 |

To determine the overall yield of the sodium salt of racemic 2-(6-methoxy-2-naphthyl)propionic acid, three methods were used for comparison: HPLC, titration and by acidifying the sodium salt of racemic 2-(6-methoxy-2-naphthyl)propionic acid. By taking the average of all three analytical methods for the three DEK/THF laboratory runs and for the three MIBK laboratory runs, the yield for DEK/THF was 73.5% compared to a 79.12% yield for MIBK.

It has been found that in the hydracarbonylation reaction the timing of the initial introduction of MVN/MIBK allowed to stir for 20 minutes at 85° C./350 psig CO before feed initiation of MVN/MIBK solution, an 85% MVN conversion was observed. As in the previous case, when MVN/MIBK is fed to the heel immediately after the desired reaction temperature/pressure is reached, >99% MVN conversion was observed. However, when the heel consisted of MVN, MIBK, NMDP, $PdCl_2$, and 10% aqueous HCl with an initial 20 minute ride, >99% of the fed MVN was converted. Thus, although it has been shown that the presence of MVN is not necessary in the heel, it is preferable to include it in the heel so as to assure complete MVN conversion in the event that a "MVN feed delay" occurs at 85° C./350 psig CO.

Similar findings have been found to apply in seeking highest conversions of MVN in a mixed THF/DEK solvent.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Without limiting the generality of the foregoing, as an illustrative example, where a claim specifies that a catalyst is a palladium compound in combination with a tertiary phosphine ligand, this phraseology refers to the makeup of the individual substances before they are combined and/or mixed separately or concurrently with one or more other materials, and in addition, at the time the catalyst is actually performing its catalytic function it need not have its original makeup—instead whatever transformations, if any, that occur in situ as the catalytic reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

In addition, reference in this specification or in the claims hereof to catalyst residue(s) means whatever composition(s) or form(s) the fresh and/or recycled catalyst acquires or becomes in the course of conducting the reaction specified. Without in any way limiting the generality of the foregoing, such residue(s) may contain, comprise or include (i) palladium-containing component(s), or (ii) phosphorus-containing component(s), or (iii) palladium- and phosphorus-containing component(s), or any combination of any two, or all three of (i), (ii) and (iii).

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:

a) conducting a palladium-catalyzed arylation of an olefin with aryl halide and/or substituted aryl halide in a liquid medium formed from (i) one or more liquid polar organic solvent/diluents, and (ii) one or more secondary or tertiary amines that (1) boil(s) below the boiling temperature of said solvent/diluent if only one solvent/diluent is used or (2) that boil(s) below the boiling temperature of at least one, but not necessarily all, of said polar solvent/diluents used in forming said medium if more than one solvent/diluent is used, to form a reaction mixture comprising olefinically-substituted aromatic compound, amine-hydrohalide and one or more of said polar organic solvents;

b) mixing (i) a concentrated aqueous solution of inorganic base that has a base strength that is greater than the base strength of said one or more secondary or tertiary amines, with (ii) at least a portion of said reaction mixture to convert amine-hydrohalide therein to free amine and inorganic halide, and to form (i) an aqueous phase containing dissolved inorganic halide, and (ii) an organic phase comprising olefinically-substituted aromatic compound, one or more of said polar organic solvents and free amine;

c) separating said phases from each other;

d) distilling off substantially all of the amine from said organic phase under low temperature and pressure conditions that suppress thermal oligomerization of the olefinically-substituted aromatic compound contained in the residual liquid phase, to thereby form a distilland composed predominately of olefinically-substituted aromatic compound and one or more of said polar organic solvents; and e) conducting a palladium-catalyzed carbonylation of at least a portion of said olefinically-substituted aromatic compound with carbon monoxide and water and/or alcohol in a liquid medium comprising at least a portion of said distilland.

2. A process according to claim 1 wherein liquid organic makeup solvent is mixed with the liquid medium during or after the distillation of d) whereby the liquid medium of e) further comprises at least a portion of said distilland and said makeup solvent.

3. A process according to claim 2 wherein said makeup solvent comprises at least one ether.

4. A process according to claim 3 wherein said ether is tetrahydrofuran.

5. A process according to claim 1 wherein at least a stoichiometric amount of said one or more secondary or tertiary amines is used relative to said aryl halide and/or substituted aryl halide, and wherein at least a stoichiometric amount of said inorganic base is used relative to the amine-hydrohalide contained in the reaction mixture with which the inorganic base is being mixed.

6. A process according to claim 1 wherein said one or more polar organic solvent/diluents comprises at least one aprotic solvent having a dielectric constant of at least about 10 at a temperature in the range of 20 to 25° C.

7. A process according to claim 1 wherein said one or more polar organic solvent/diluents is one or more aprotic solvents each such solvent having a dielectric constant in the range of about 10 to about 30 at a temperature in the range of 20 to 25° C.

8. A process according to claim 1 wherein said one or more polar organic solvent/diluents comprises at least one ketone and said one or more secondary or tertiary amines is a tertiary amine.

9. A process according to claim 8 wherein said ketone is diethyl ketone and said tertiary amine is a liquid trialkylamine.

10. A process according to claim 1 wherein said one or more polar organic solvent/diluents comprises at least one nitrile and said one or more secondary or tertiary amines is a tertiary amine.

11. A process according to claim 10 wherein said nitrile is acetonitrile and said tertiary amine is a liquid trialkylamine.

12. A process according to claim 1 wherein said one or more polar organic solvent/diluents comprises at least one nitrile and at least one ketone, and said one or more secondary or tertiary amines is a tertiary amine.

13. A process according to claim 12 wherein said nitrile is acetonitrile, wherein said ketone is diethyl ketone, and wherein said tertiary amine is a liquid trialkylamine.

14. A process according to claim 9 wherein said trialkylamine is triethylamine.

15. A process according to claim 1 wherein the concentration of alkali metal halide in the substantially homogeneous aqueous phase formed in b) is at least about 33 weight percent.

16. A process according to claim 1 wherein said concentrated aqueous solution of inorganic base is (i) a concentrated aqueous sodium hydroxide solution, or (ii) a concentrated aqueous potassium hydroxide solution, or (iii) a concentrated aqueous sodium hydroxide and potassium hydroxide solution.

17. A process according to claim 16 wherein said concentrated aqueous solution of inorganic base is a 20–50 wt % aqueous sodium hydroxide solution.

18. A process according to claim 1 wherein said aryl halide and/or substituted aryl halide is a substituted aryl monobromide; wherein the olefin is a vinylic olefin; and wherein the respective palladium catalysts used in performing the arylation of a) and the carbonylation of e) are both formed at least from (i) at least one salt of palladium in which the palladium has a valence of 1 or 2, and (ii) at least one tertiary phosphine ligand having at least one phenyl or alkyl-substituted phenyl group in the molecule.

19. A process according to claim 18 wherein said respective palladium catalysts are both formed at least from (i) at least one palladium(II) salt, and (ii) at least one tertiary phosphine ligand having in the molecule (A) one cycloalkyl group or alkyl-substituted cycloalkyl group and either (B) two phenyl or alkyl-substituted phenyl groups or (C) one phenyl group and one alkyl-substituted phenyl group.

20. A process according to claim 18 wherein said respective palladium catalysts are both formed at least from (i) at least one palladium(II) salt, and (ii) neomenthyldiphenylphosphine.

21. A process according to claim 18 wherein said respective palladium catalysts are both formed from (i) at least one palladium(II) carboxylate salt and/or at least one palladium (II) halide selected from palladium(II) chloride, palladium (II) bromide and palladium(II) iodide, and (ii) neomenthyldiphenylphosphine.

22. A process according to claim 1 wherein said aryl halide and/or substituted aryl halide is a substituted aryl monobromide; wherein the olefin is a vinylic olefin; wherein the palladium catalyst used in performing the arylation of a) is formed at least from (i) at least one salt of palladium in which the palladium has a valence of 1 or 2, and (ii) at least one tertiary phosphine ligand having at least one phenyl or alkyl-substituted phenyl group in the molecule; and wherein the palladium catalyst used in performing the carbonylation of e) is formed at least from (i) at least one salt of palladium in which the palladium has a valence of 1 or 2, (ii) at least one tertiary phosphine ligand having at least one phenyl or alkyl-substituted phenyl group in the molecule, and (iii) at least one copper compound.

23. A process according to claim 22 wherein said palladium catalyst used in performing the arylation of a) is formed at least from (i) at least one palladium(II) salt, and (ii) at least one tertiary phosphine ligand having in the molecule (A) one cycloalkyl group or alkyl-substituted cycloalkyl group and either (B) two phenyl or alkyl-substituted phenyl groups or (C) one phenyl group and one alkyl-substituted phenyl group; and wherein said palladium catalyst used in performing the carbonylation of e) is formed at least from (i) at least one palladium(II) salt, (ii) at least one tertiary phosphine ligand having in the molecule (A) one cycloalkyl group or alkyl-substituted cycloalkyl group and either (B) two phenyl or alkyl-substituted phenyl groups or (C) one phenyl group and one alkyl-substituted phenyl group, and (iii) at least one copper compound.

24. A process according to claim 23 wherein said at least one copper compound used in forming the palladium catalyst used in performing the carbonylation of e) is a copper (II) salt.

25. A process according to claim 18 wherein said palladium catalyst used in performing the arylation of a) is formed at least from (i) at least one palladium(II) salt, and (ii) neomenthyldiphenylphosphine; and wherein said palladium catalyst used in performing the carbonylation of e) is formed at least from (i) at least one palladium(II) salt, (ii) neomenthyldiphenylphosphine, and (iii) at least one copper (II) salt.

26. A process according to claim 22 wherein said palladium catalyst used in performing the arylation of a) is formed from (i) at least one palladium(II) carboxylate salt and/or at least one palladium(II) halide selected from palladium(II) chloride, palladium(II) bromide and palladium (II) iodide, and (ii) neomenthyldiphenylphosphine; and wherein said palladium catalyst used in performing the carbonylation of e) is formed from (i) at least one palladium (II) carboxylate salt and/or at least one palladium(II) halide selected from palladium(II) chloride, palladium(II) bromide and palladium(II) iodide, (ii) neomenthyldiphenylphosphine, and (iii) at least one copper (II) salt.

27. A process according to claim 26 wherein said at least one copper(II) salt is a copper(II) chloride, bromide or iodide.

28. A process according to claim 1 wherein said aryl halide and/or substituted aryl halide is a substituted aryl monochloride, and/or a substituted aryl monobromide, and/ or a substituted aryl monoiodide; and wherein said olefin is at least one compound of the formula

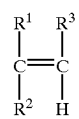

wherein $R^1$, $R^2$, and $R^3$ are hydrogen atoms, $C_1$ to $C_6$ alkyl, substituted or unsubstituted phenyl, and/or trifluoromethyl.

29. A process according to claim 28 wherein the substituted aryl group of said substituted aryl monohalide is phenyl substituted with alkyl, naphthyl substituted with alkoxy, phenyl substituted with aryloxy, aryl substituted with fluoro, or phenyl substituted with aroyl.

30. A process according to claim 29 wherein $R^1$, $R^2$, and $R^3$ are hydrogen atoms, methyl, and/or trifluoromethyl.

31. A process according to claim 28 wherein the substituted aryl group of said substituted aryl monohalide is an isobutylphenyl group, and $R^1$, $R^2$, and $R^3$ are hydrogen atoms.

32. A process according to claim 28 wherein the substituted aryl group of said substituted aryl monohalide is a methoxynaphthyl group, and $R^1$, $R^2$, and $R^3$ are hydrogen atoms.

33. A process according to claim 28 wherein the substituted aryl group of said substituted aryl monohalide is a phenoxyphenyl group, and $R^1$, $R^2$, and $R^3$ are hydrogen atoms.

34. A process according to claim 28 wherein the substituted aryl group of said substituted aryl monohalide is a fluorobiphenylyl group, and $R^1$, $R^2$, and $R^3$ are hydrogen atoms.

35. A process according to claim 28 wherein the substituted aryl group of said substituted aryl monohalide is a benzoylphenyl group, and $R^1$, $R^2$, and $R^3$ are hydrogen atoms.

36. A process according to claim 1 wherein liquid organic makeup solvent is mixed with the liquid medium during or after the distillation of d) but before conducting the palladium-catalyzed carbonylation of e), and wherein residual solids present in the resultant mixture are separated therefrom before conducting the palladium-catalyzed carbonylation of e), whereby (i) the liquid medium of e) further comprises at least a portion of said distilland and said makeup solvent, and (ii) the liquid medium of e) before conducting the palladium-catalyzed carbonylation of e) has a reduced content of solids, if any.

37. A process according to claim 36 wherein said residual solids present in the resultant mixture are separated therefrom by filtering said resultant mixture.

38. A process according to claim 36 wherein said liquid organic makeup solvent consists essentially of tetrahydrofuran.

39. A process which comprises:
   a) conducting a palladium-catalyzed arylation of ethylene with 2-bromo-6-methoxynaphthalene in a liquid medium formed from (i) one or more liquid polar organic solvent/diluents, and (ii) at least a stoichiometric amount relative to the 2-bromo-6-methoxynaphthalene of one or more secondary or tertiary amines that (1) boil(s) below the boiling temperature of said solvent/diluent if only one solvent/diluent is used in forming said medium or (2) that boil(s) below the boiling temperature of at least one, but not necessarily all, of said polar solvent/diluents used in forming said medium if more than one solvent/diluent is used in forming said medium, to form a reaction mixture comprising 6-methoxy-2-vinylnaphthalene, amine hydrobromide and one or more of said polar organic solvents;
   b) mixing at least a stoichiometric amount of a concentrated aqueous alkali metal hydroxide solution with at least a portion of said reaction mixture to convert the amine-hydrobromide therein to free amine and alkali metal bromide, and to form (i) an aqueous phase with alkali metal bromide dissolved therein, and (ii) an organic phase comprising 6-methoxy-2-vinylnaphthalene and one or more of said polar organic solvents;
   c) separating said phases from each other;
   d) distilling off substantially all of the amine from said organic phase under low temperature and pressure conditions that suppress thermal oligomerization of the 6-methoxy-2-vinylnaphthalene contained in the residual liquid phase, to thereby form a distilland composed predominately of 6-methoxy-2-vinylnaphthalene and one or more of said polar organic solvents; and
   e) conducting a palladium-catalyzed carbonylation of at least a portion of said olefinically-substituted aromatic compound with carbon monoxide and water and/or alcohol in a liquid medium comprising at least a portion of said distilland.

40. A process according to claim 39 wherein liquid organic makeup solvent is mixed with the liquid medium during or after the distillation of d) but before conducting the palladium-catalyzed carbonylation of e) whereby the liquid medium of e) further comprises at least a portion of said distilland and said makeup solvent.

41. A process according to claim 40 wherein residual solids present in the resultant mixture are separated therefrom, whereby the liquid medium of e) before conducting the palladium-catalyzed carbonylation of e) has a reduced content of solids, if any.

42. A process according to claim 41 wherein said residual solids present in the resultant mixture are separated therefrom by filtering said resultant mixture before conducting the palladium-catalyzed carbonylation of e).

43. A process according to claim 42 wherein said carbonylation of e) is performed by (1) mixing at least one palladium(II) salt, at least one tertiary phosphine ligand and aqueous hydrochloric acid with the filtered liquid medium of e) and (2) conducting the carbonylation under a pressurized atmosphere of carbon monoxide.

44. A process according to claim 43 wherein said catalyzed arylation of ethylene of a) is performed by mixing at least one palladium(II) salt and at least one tertiary phosphine ligand with the liquid medium of a) and conducting the arylation under a pressurized atmosphere of ethylene.

45. A process according to claim 44 wherein said liquid medium of a) is formed substantially entirely from diethyl ketone and triethylamine.

46. A process according to claim 45 wherein said liquid organic makeup solvent is tetrahydrofuran.

47. A process according to claim 46 wherein the distillation of c) is performed in the range of about 50 to about 350 mm Hg to distill off triethylamine to a level at which the weight ratio of triethylamine 6-methoxy-2-vinylnaphthalene is about 0.016 or less.

48. A process according to claim 47 wherein the concentrated aqueous alkali metal hydroxide solution is (i) a concentrated aqueous sodium hydroxide solution, (ii) a concentrated aqueous potassium hydroxide solution, or (iii) a concentrated aqueous sodium hydroxide and potassium hydroxide solution; and wherein the concentration of such solution is such as to provide an aqueous solution of such alkali metal bromide(s) having a specific gravity when and if measured at 25° C. of at least 1.08 grams per milliliter.

49. A process according to claim 47 wherein the concentrated aqueous alkali metal hydroxide solution is a 20–50 wt % aqueous sodium hydroxide solution.

50. A process according to claim 42 wherein said carbonylation of e) is performed by (1) mixing at least one palladium(II) salt, at least one copper salt, at least one tertiary phosphine ligand, and aqueous hydrochloric acid with the filtered liquid medium of e), and (2) conducting the carbonylation under a pressurized atmosphere of carbon monoxide.

51. A process according to claim 50 wherein said catalyzed arylation of ethylene of a) is performed by mixing at least one palladium(II) salt and at least one tertiary phosphine ligand with the liquid medium of a) and conducting the arylation under a pressurized atmosphere of ethylene.

52. A process according to claim 51 wherein said liquid medium of a) is formed substantially entirely from diethyl ketone and triethylamine.

53. A process according to claim 52 wherein said liquid organic makeup solvent is tetrahydrofuran.

54. A process according to claim 53 wherein the distillation of c) is performed in the range of about 50 to about 350 mm Hg to distill off triethylamine to a level at which the weight ratio of triethylamine 6-methoxy-2-vinylnaphthalene is about 0.016 or less.

55. A process according to claim 54 wherein the concentrated aqueous alkali metal hydroxide solution is (i) a concentrated aqueous sodium hydroxide solution, (ii) a concentrated aqueous potassium hydroxide solution, or (iii) a concentrated aqueous sodium hydroxide and potassium hydroxide solution; and wherein the concentration of such solution is such as to provide an aqueous solution of such alkali metal bromide(s) having a specific gravity when and if measured at 25° C. at least 1.08 grams per milliliter.

56. A process which comprises (a) forming a reaction product composition comprising arylolefin or substituted arylolefin and amine-hydrohalide in a liquid polar organic solvent medium by palladium-catalyzed arylation of a 1-olefin with an aryl halide and/or substituted arylhalide in a liquid polar organic solvent containing one or more secondary or tertiary amines as hydrogen halide acceptor, and (b) mixing with at least a portion of said reaction product composition a concentrated aqueous solution of inorganic base having a base strength greater than that of said one or more secondary or tertiary amines to thereby form (i) an organic phase containing said arylolefin or substituted arylolefin and said one or more secondary or tertiary amines, and (ii) a lower aqueous phase containing dissolved inorganic salt such that said aqueous phase has a specific gravity of at least 1.08 grams per milliliter, when and if measured at 25° C., and (c) separating said phases from each other.

57. A process according to claim 56 wherein in (a) the aryl halide and/or substituted aryl halide is a substituted aryl bromide so that said amine-hydrohalide is amine-hydrobromide and said dissolved inorganic salt is inorganic bromide salt; wherein in (a) said liquid polar organic solvent contains at least a stoichiometric amount of said one or more secondary or tertiary amines as hydrogen halide acceptor; and wherein in (b) at least a stoichiometric amount of said concentrated aqueous solution of inorganic base is mixed with said reaction product composition.

58. A process according to claim 57 wherein the concentrated aqueous solution is (i) a 20 to 50 wt % aqueous sodium hydroxide solution, (ii) a 20 to 50 wt % aqueous potassium hydroxide solution, or (iii) a 20 to 50 wt % aqueous sodium hydroxide and potassium hydroxide solution.

59. A process according to claim 57 wherein the one or more secondary or tertiary amines boil at temperature(s) below the temperature at which at least a portion of the liquid polar organic solvent boils or begins to boil, and wherein after the separation of said phases, said one or more secondary or tertiary amines are distilled from the organic phase containing said arylolefin or substituted arylolefin.

60. A process according to claim 59 wherein the distillation is performed under temperature and pressure conditions that prevent or at least minimize any thermally-induced reaction and/or decomposition of said arylolefin or substituted arylolefin.

61. A process according to claim 60 wherein the aryl halide and/or substituted aryl halide is a substituted aryl bromide so that said amine-hydrohalide is amine-hydrobromide and said dissolved inorganic salt is inorganic bromide salt.

62. A process according to claim 61 wherein the concentrated aqueous solution is (i) a 20 to 50 wt % aqueous sodium hydroxide solution, (ii) a 20 to 50 wt % aqueous potassium hydroxide solution, or (iii) a 20 to 50 wt % aqueous sodium hydroxide and potassium hydroxide solution.

63. A process according to claim 62 wherein said substituted aryl bromide is 2-bromo-6-methoxynaphthalene.

64. A process according to claim 63 wherein said liquid polar organic solvent consists essentially of diethyl ketone; wherein said one or more secondary or tertiary amines consist essentially of triethylamine; and wherein said concentrated aqueous solution is a 23 to 27 wt % aqueous sodium hydroxide solution.

65. A process according to claim 62 wherein said substituted aryl bromide is 4-bromoisobutylbenzene.

66. A process according to claim 65 wherein said liquid polar organic solvent consists essentially of diethyl ketone and acetonitrile, and wherein said one or more secondary or tertiary amines consist essentially of triethylamine.

67. A process which comprises
  A) forming a reaction product composition comprising arylalkylcarboxylic acid or substituted arylalkylcarboxylic acid in a liquid polar organic solvent medium by palladium-catalyzed hydracarbonylation of an arylolefin or substituted arylolefin in a liquid medium comprising polar organic solvent, water, HCl, and at least one ether;
  B) mixing with at least a portion of said reaction product composition an aqueous solution of inorganic base to thereby form a mixture comprising an aqueous phase containing dissolved inorganic salt of said arylalkylcarboxylic acid or substituted arylalkylcarboxylic acid, and before and/or during and/or after such mixing, distilling at least a substantial portion of the ether from the reaction mixture, such that a mixture of residual organic phase and such aqueous phase remain as a distillation residue;
  C) separating the phases from each other;
  D) distilling residual organic impurities from at least a portion of the aqueous phase and providing an aqueous solution having a concentration in the range of about 10 and about 35 wt %, by, if necessary, adjusting the concentration of such aqueous solution to said range of about 10 and about 35 wt % by removal therefrom or addition thereto of water;
  E) washing at least a portion of the aqueous solution with substantially non-polar liquid organic solvent at least twice;
  F) mixing non-oxidizing mineral acid with at least a portion of the aqueous phase in the presence of substantially non-polar liquid solvent to form (i) an organic phase composed of a solution of arylalkylcarboxylic acid or substituted arylalkylcarboxylic acid in substantially non-polar liquid organic solvent and (ii) an aqueous phase;
  G) separating at least a portion of the phases from each other; and
  H) crystallizing arylalkylcarboxylic acid or substituted arylalkylcarboxylic acid from at least a portion of the substantially non-polar liquid organic solvent.

68. A process according to claim 67 wherein the arylalkylcarboxylic acid or substituted arylalkylcarboxylic acid in the reaction product composition in A) is racemic 2-(6-methoxy-2-naphthyl)propionic acid.

69. A process according to claim 68 wherein the polar organic solvent in A) consists essentially of at least one liquid ketone or at least one liquid nitrile or a mixture thereof, and wherein the at least one ether in A) consists essentially of tetrahydrofuran.

70. A process according to claim 69 wherein the aqueous solution of inorganic base of B) is a 10 to 50 wt % aqueous solution of sodium hydroxide or potassium hydroxide, or of both of them, and wherein such solution is mixed with the reaction product composition before conducting the distillation of B).

71. A process according to claim 69 wherein said substantially non-polar liquid organic solvent is at least one liquid aromatic hydrocarbon.

72. A process according to claim 69 wherein the non-oxidizing mineral acid is sulfuric acid.

73. A process according to claim 68 wherein the polar organic solvent in A) consists essentially of diethyl ketone; wherein the at least one ether in A) consists essentially of tetrahydrofuran; wherein the aqueous solution of inorganic base of B) is a 10 to 50 wt % aqueous solution of sodium hydroxide or potassium hydroxide, or both; wherein said solution of sodium hydroxide or potassium hydroxide, or both is mixed with the reaction product composition before conducting the distillation of B); wherein the non-oxidizing mineral acid is sulfuric acid; and wherein said substantially non-polar liquid organic solvent is at least one liquid aromatic hydrocarbon.

74. A process according to claim 73 wherein the polar organic solvent in A) consists essentially of diethyl ketone, and wherein said at least one liquid aromatic hydrocarbon consists essentially of toluene.

75. A process according to claim 67 wherein the arylalkylcarboxylic acid or substituted arylalkylcarboxylic acid in the reaction product composition in A) is 2-(4-isobutylphenyl)propionic acid.

76. A process according to claim 75 wherein the polar organic solvent in A) consists essentially of at least one liquid ketone, and wherein the at least one ether in A) consists essentially of tetrahydrofuran.

77. A process according to claim 76 wherein the aqueous solution of inorganic base of B) is a 10 to 50 wt % aqueous solution of sodium hydroxide or potassium hydroxide, or of both of them, and wherein such solution is mixed with the reaction product composition before conducting the distillation of B).

78. A process according to claim 76 wherein said substantially non-polar liquid organic solvent is at least one liquid aromatic hydrocarbon.

79. A process according to claim 76 wherein the non-oxidizing mineral acid is sulfuric acid.

80. A process according to claim 75 wherein the polar organic solvent in A) consists essentially of diethyl ketone; wherein the at least one ether in A) consists essentially of tetrahydrofuran; wherein the aqueous solution of inorganic base of B) is a 10 to 50 wt % aqueous solution of sodium hydroxide or potassium hydroxide, or both; wherein said solution of sodium hydroxide or potassium hydroxide, or both is mixed with the reaction product composition before conducting the distillation of B); wherein the non-oxidizing mineral acid is sulfuric acid; and wherein said substantially non-polar liquid organic solvent is at least one liquid aromatic hydrocarbon.

81. A process according to claim 80 wherein the polar organic solvent in A) consists essentially of diethyl ketone, and wherein said at least one liquid aromatic hydrocarbon consists essentially of toluene.

82. A process which comprises (a) forming a reaction product composition comprising arylolefin or substituted arylolefin and amine-hydrohalide in a liquid polar organic solvent medium by palladium-catalyzed arylation of 1-olefin with an aryl halide and/or substituted aryl halide in a liquid polar organic solvent containing one or more secondary or tertiary amines as hydrogen halide acceptor, and (b) mixing with at least a portion of said reaction product composition a dilute aqueous acid to thereby form (i) an organic phase containing said arylolefin or substituted arylolefin, and (ii) an acidic aqueous phase containing dissolved amine hydrohalide, and (c) separating at least a portion of said phases from each other.

83. A process according to claim 82 wherein in (a) the aryl halide and/or substituted aryl halide is an aryl bromide or substituted aryl bromide, and wherein said dilute aqueous acid is dilute aqueous hydrochloric acid.

84. A process according to claim 82 further comprising subjecting at least a portion of the separated organic phase from (c) to palladium-catalyzed carbonylation to form arylalkylcarboxylic acid or ester, or substituted arylalkylcarboxylic acid or ester.

85. A process according to claim 84 wherein the palladium-catalyzed carbonylation is palladium-catalyzed hydracarbonylation to form arylalkylcarboxylic acid or substituted arylalkylcarboxylic acid.

86. A process according to claim 85 further comprising mixing together at least a portion of the separated aqueous phase from (c) and a strong inorganic base to form free amine and an aqueous solution of inorganic halide.

87. A process according to claim 86 wherein the aryl halide and/or substituted aryl halide is an aryl bromide or substituted aryl bromide.

88. A process according to claim 85 wherein said aryl bromide or substituted aryl bromide is 2-bromo-6-methoxynaphthalene.

89. A process according to claim 88 wherein said one or more secondary or tertiary amines consist essentially of triethylamine, and wherein said dilute aqueous acid is dilute aqueous hydrochloric acid.

90. A process according to claim 86 wherein said aryl bromide or substituted aryl bromide is 2-bromo-6-methoxynaphthalene.

91. A process according to claim 90 wherein said one or more secondary or tertiary amines consist essentially of triethylamine, and wherein said dilute aqueous acid is dilute aqueous hydrochloric acid.

92. A process according to claim 85 wherein said aryl bromide or substituted aryl bromide is 4-bromoisobutylbenzene.

93. A process according to claim 92 wherein said one or more secondary or tertiary amines consist essentially of triethylamine, and wherein said dilute aqueous acid is dilute aqueous hydrochloric acid.

94. A process according to claim 86 wherein said aryl bromide or substituted aryl bromide is 4-bromoisobutylbenzene.

95. A process according to claim 94 wherein said one or more secondary or tertiary amines consist essentially of triethylamine, and wherein said dilute aqueous acid is dilute aqueous hydrochloric acid.

96. A process according to claim 82 wherein in (a) the aryl halide and/or substituted aryl halide is 2bromo-6-methoxynaphthalene.

97. A process according to claim 96 wherein the dilute aqueous acid used in (b) is dilute aqueous hydrochloric acid.

98. A process according to claim 82 wherein in (a) the aryl halide and/or substituted aryl halide is 3-bromobenzophenone.

99. A process according to claim 98 wherein said dilute aqueous acid is dilute aqueous hydrochloric acid.

100. A process which comprises:
   A) conducting a palladium-catalyzed arylation of an olefin with aryl halide and/or substituted aryl halide in a liquid medium formed from (i) at least one liquid polar organic solvent/diluent, and (ii) at least one secondary or tertiary amine hydrogen halide acceptor capable of forming a water-soluble amine-hydrohalide, to form a reaction mixture comprising olefinically-substituted aromatic compound, amine-hydrohalide and one or more polar organic solvents;
   B) contacting (i) at least a portion of the reaction mixture from A) with (ii) an aqueous mineral acid to form (i) an aqueous phase containing dissolved amine-hydrohalide and, optionally another water-soluble amine salt of said acid, and (ii) a liquid organic phase comprising olefinically-substituted aromatic compound and one or more polar organic solvents;
   C) separating the foregoing phases from each other;
   D) conducting a palladium-catalyzed carbonylation of at least a portion of said olefinically-substituted aromatic compound with carbon monoxide and water and/or alcohol in a liquid medium comprising one or more liquid polar organic solvent/diluents.

101. A process according to claim 100 wherein the olefin is ethylene, wherein the aryl halide and/or substituted aryl halide is 3-bromobenzophenone, wherein the liquid polar organic solvent/diluent in A) is diethyl ketone or methyl ethyl ketone having a lower specific gravity than water, wherein the hydrogen halide acceptor is triethylamine, wherein the aqueous mineral acid is dilute hydrochloric acid whereby said organic phase is superposed on said aqueous phase, and wherein the aqueous phase is drained away from the liquid organic phase leaving the organic phase within the reactor in which the palladium-catalyzed carbonylation of D) is performed.

102. A process according to claim 100 wherein a single organic solvent/diluent is used in A), and the same single organic solvent/diluent is also present in, or constitutes, the solvent/diluent of D).

103. A process according to claim 100 wherein before conducting D), steps B) and C) are repeated in sequence so as to further reduce the amount of amine left in the organic phase.

104. A process according to claim 100 wherein steps A), B), C), and D) are conducted in the same reaction vessel, and the same single organic solvent/diluent is also present in, or constitutes, the solvent/diluent of D).

105. A process according to claim 100 wherein the olefin is ethylene, wherein the aryl halide and/or substituted aryl halide is 3-bromobenzophenone, wherein the liquid polar organic solvent/diluent in A) is diethyl ketone or methyl ethyl ketone having a lower specific gravity than water, wherein the hydrogen halide acceptor is triethylamine, wherein the aqueous mineral acid is dilute hydrochloric acid whereby said organic phase is superposed on said aqueous phase, and wherein the aqueous phase is drained away from the liquid organic phase leaving the organic phase within the reactor in which the palladium-catalyzed carbonylation of D) is performed, wherein steps A), B), C), and D) are conducted in the same reaction vessel, and wherein the organic solvent/diluent in D) is also diethyl ketone or methyl ethyl ketone.

106. A process which comprises the following sequence of reactions is conducted either in one plant facility or in two or more separate plant facilities:
   A) brominating benzoyl chloride to form m-bromobenzoyl chloride;
   B) reacting m-bromobenzoyl chloride from A) with benzene in the presence of a Friedel-Crafts catalyst to form m-bromobenzophenone;
   C) converting m-bromobenzophenone from B) to m-vinylbenzophenone by palladium-catalyzed arylation of ethylene in a liquid polar organic solvent/diluent that contains at least a stoichiometric amount of at least one secondary or tertiary amine as hydrogen halide acceptor;
   D) contacting reaction product mixture formed in C) with aqueous mineral acid to thereby form (i) a liquid organic phase containing m-vinylbenzophenone, and (ii) a liquid aqueous phase containing dissolved therein the hydrohalide of the secondary or tertiary amine, and, optionally, another water-soluble acid salt of the secondary or tertiary amine;
   E) effecting a separation between the aqueous and organic phases formed in D);
   F) subjecting m-vinylbenzophenone from E) to palladium-catalyzed carbonylation with carbon monoxide in the presence of water or alcohol and hydrochloric acid to form 2-(3-benzoylphenyl)propionic acid if water is used, or an ester of 2-(3-benzoylphenyl) propionic acid if an alcohol is used.

107. A process according to claim 106 wherein in A) the bromination is conducted using bromine or bromine chloride; wherein in C) the liquid polar organic solvent/diluent is diethyl ketone or methyl isobutyl ketone having a lower specific gravity than water, and the amine is triethylamine; wherein in D) the aqueous mineral acid is dilute hydrochloric acid whereby said organic phase is superposed on said aqueous phase; and wherein in E) the aqueous phase is drained away from the liquid organic phase leaving the organic phase within the reactor in which the palladium-catalyzed carbonylation of F) is conducted.

108. A process according to claim 107 wherein the palladium-catalyzed carbonylation of m-vinylbenzophenone with carbon monoxide is conducted in the presence of water.

109. A process according to claim 108 wherein the palladium-catalyzed carbonylation of m-vinylbenzophenone with carbon monoxide is conducted in the same organic phase as in E), optionally with an additional makeup quantity of the same solvent/diluent.

110. A process according to claim 109 wherein the palladium-catalyzed carbonylation of m-vinylbenzophenone with carbon monoxide is conducted in the presence of water.

111. A process which comprises:
   A) reacting arylolefin or substituted arylolefin with carbon monoxide and water in the presence of palladium catalyst formed at least from (1) palladium or palladium compound and (2) organophosphine ligand, to form a reaction mass comprising (a) arylalkylcarboxylic acid or substituted arylalkylcarboxylic acid, and (b) one or more residual catalyst species;
   B) mixing together at least a portion of such reaction mass and aqueous inorganic base to form (i) an aqueous phase with water-soluble salt of the arylalkylcarboxylic acid or substituted arylalkylcarboxylic acid dissolved therein, and (ii) an organic phase having at least a portion of the residual catalyst species dissolved therein;

C) separating these phases, and recycling at least a portion of the separated phase (ii) to A) for use in performing additional reaction pursuant to A).

112. A process according to claim 111 wherein said palladium catalyst in A) comprises residual catalyst species contained in the portion of separated phase (ii) recycled to A) pursuant to C).

113. A process according to claim 111 wherein said palladium catalyst in A) comprises
I) fresh catalyst formed at least from (1) palladium or palladium compound and (2) organophosphine ligand, and
II) residual catalyst species contained in the portion of separated phase (ii) recycled to A) pursuant to C).

114. A process according to claim 111 wherein the reaction in A) is conducted in the additional presence of HCl.

115. A process according to claim 114 wherein said palladium catalyst in A) comprises residual catalyst species contained in the portion of separated phase (ii) recycled to A) pursuant to C), said residual catalyst species having been originally formed by addition of (1) at least one palladium compound and (2) tertiary phosphine to the mixture subjected to reaction in A).

116. A process according to claim 114 wherein said palladium catalyst in A) comprises
I) fresh catalyst formed at least from (1) at least one palladium compound and (2) tertiary phosphine, and
II) residual catalyst species contained in the portion of separated phase (ii) recycled to A) pursuant to C).

117. A process according to claim 114 wherein the reaction in A) is conducted in the additional presence of at least one organic solvent/diluent.

118. A process according to claim 117 wherein said palladium catalyst in A) comprises residual catalyst species contained in the portion of separated phase (ii) recycled to A) pursuant to C), said residual catalyst species having been originally formed by addition of (1) at least one palladium (II) salt and (2) trihydrocarbylphosphine to the mixture subjected to reaction in A).

119. A process according to claim 117 wherein said palladium catalyst in A) comprises
I) fresh catalyst formed at least from (1) at least one palladium(II) salt and (2) trihydrocarbyl phosphine, and
II) residual catalyst species contained in the portion of separated phase (ii) recycled to A) pursuant to C).

120. A process according to claim 114 wherein the reaction in A) is conducted in the additional presence of at least one ether that boils at a lower temperature than said arylalkylcarboxylic acid or substituted arylalkylcarboxylic acid, and at least one ketone that boils at a temperature sufficiently above said ether to enable said ether to be stripped from said reaction mass, and wherein at least a portion of said ether is stripped from said reaction mass after completing the reaction in A).

121. A process according to claim 120 wherein said palladium catalyst in A) comprises residual catalyst species contained in the portion of separated phase (ii) recycled to A) pursuant to C), said residual catalyst species having been originally formed by addition to the mixture subjected to reaction in A) of (1) at least one palladium(II) halide or carboxylate salt and (2) trihydrocarbylphosphine having at least two aryl groups in the molecule.

122. A process according to claim 120 wherein said palladium catalyst in A) comprises
I) fresh catalyst formed by addition to the mixture subjected to reaction in A) of (1) at least one palladium(II) halide or carboxylate salt and (2) trihydrocarbyl phosphine having at least two aryl groups in the molecule, and
II) residual catalyst species contained in the portion of separated phase (ii) recycled to A) pursuant to C).

123. A process according to claim 120 wherein said ether consists essentially of tetrahydrofuran, wherein said ketone consists essentially of diethyl ketone, and wherein at least a portion of the tetrahydrofuran is stripped from said reaction mass before conducting B).

124. A process according to claim 123 wherein said palladium catalyst in A) comprises residual catalyst species contained in the portion of separated phase (ii) recycled to A) pursuant to C), said residual catalyst species having been originally formed by addition to the mixture subjected to reaction in A) of (1) palladium(II) chloride and (2) neomenthyldiphenylphosphine.

125. A process according to claim 123 wherein said palladium catalyst in A) comprises
I) fresh catalyst formed by addition to the mixture subjected to reaction in A) of (1) palladium(II) chloride and (2) neomenthyldiphenylphosphine, and
II) residual catalyst species contained in the portion of separated phase (ii) recycled to A) pursuant to C).

126. A process which comprises
A) forming a reaction product composition comprising arylalkylcarboxylic acid or substituted arylalkylcarboxylic acid in a liquid reaction medium by palladium-catalyzed hydracarbonylation of arylolefin or substituted arylolefin in a liquid medium comprising polar organic solvent, water, and HCl;
B) mixing with at least a portion of said reaction product composition an aqueous solution of inorganic base to thereby form a mixture comprising (i) organic phase containing dissolved catalyst residue(s) in whatever chemical composition it exists or they exist while in said residual organic phase, (ii) aqueous phase containing dissolved inorganic salt of said arylalkylcarboxylic acid or substituted arylalkylcarboxylic acid, and optionally, (iii) a solids phase containing palladium and/or one or more palladium compounds in whatever chemical composition it exists or they exist while in said solids phase;
C) separating said phases from each other; and
D) recycling at least a portion of the separated solids-free organic phase containing said catalyst residue(s) as a portion of the liquid reaction medium for use in additional hydracarbonylation pursuant to A).

127. A process according to claim 126 wherein said reaction product composition of A) additionally comprises at least one organophosphine ligand in whatever chemical composition it exists while in said reaction product composition of A), and wherein said separated solids-free organic phase being recycled in D) additionally contains at least one organophosphine ligand in whatever chemical composition it exists while dissolved in said separated solids-free organic phase.

128. A process according to claim 127 wherein said organophosphine ligand is trihydrocarbylphosphine in whatever chemical composition it exists while in said reaction product composition of A).

129. A process according to claim 127 wherein said organophosphine ligand is neomenthyldiphenylphosphine in whatever chemical composition it exists while in said reaction product composition of A).

130. A process according to claim 126 wherein said solids phase is present in B).

131. A process according to claim 130 wherein palladium values are recovered from at least a portion of the solids phase separated in C).

132. A process which comprises
A) conducting a palladium-catalyzed hydracarbonylation of arylolefin or substituted arylolefin with carbon monoxide in a reaction mixture formed at least from polar organic solvent, water, palladium catalyst, and aqueous HCl to produce a reaction product mixture comprising as constituents at least arylalkylcarboxylic acid or substituted arylalkylcarboxylic acid, polar organic solvent, and catalyst residue(s) in whatever chemical composition and form said respective constituents exist in said reaction product mixture;
B) removing a portion of the polar organic solvent from said reaction product mixture to form a more concentrated reaction product mixture;
C) mixing with at least a portion of said more concentrated reaction product mixture an aqueous solution of inorganic base to thereby form a mixture comprising (i) organic phase containing at least dissolved catalyst residue(s) in whatever chemical composition it exists or they exist while in said organic phase, (ii) aqueous phase containing at least dissolved inorganic salt of said arylalkylcarboxylic acid or substituted arylalkylcarboxylic acid in whatever chemical composition it exists while in said aqueous phase, and (iii) a solids phase containing at least palladium and/or one or more palladium compounds in whatever chemical composition it exists or they exist while in said solids phase;
D) separating said phases from each other; and
E) recycling to A) at least a portion of the separated solids-free organic phase containing dissolved catalyst residue(s) to serve as a portion of the reaction mixture for additional palladium-catalyzed hydrocarbonylation of arylolefin or substituted arylolefin pursuant to A).

133. A process according to claim 132 further comprising recovering at least a portion of said solids phase and converting recovered solids phase into fresh palladium-containing catalyst for use in conducting additional palladium-catalyzed hydrocarbonylation of arylolefin or substituted arylolefin pursuant to A).

134. A process according to claim 132 wherein said catalyst when fresh is formed at least from (1) palladium or palladium compound and (2) organophosphine ligand.

135. A process according to claim 132 wherein said catalyst when fresh is formed at least from (1) palladium(II) halide or carboxylate and (2) trihydrocarbylphosphine ligand.

136. A process which comprises
A) conducting a palladium-catalyzed arylation of a 1-olefin in a first reaction mixture formed at least from aryl halide or substituted aryl halide, polar organic solvent, hydrogen halide acceptor, and palladium arylation catalyst to produce a first reaction product mixture comprising as constituents at least arylolefin or substituted arylolefin, polar organic solvent, product of hydrogen halide and hydrogen halide acceptor, and catalyst residue(s) in whatever chemical composition and form said respective constituents exist in said first reaction product mixture;
B) conducting a palladium-catalyzed hydrocarbonylation of arylolefin or substituted arylolefin formed in A) with carbon monoxide in a second reaction mixture formed at least from polar organic solvent, water, palladium hydrocarbonylation catalyst, and aqueous HCl to produce a second reaction product mixture comprising as constituents at least arylalkylcarboxylic acid or substituted arylalkylcarboxylic acid, polar organic solvent, and catalyst residue(s) in whatever chemical composition and form said respective constituents exist in said second reaction product mixture;
C) mixing with at least a portion of said second reaction product mixture an aqueous solution of inorganic base to thereby form a mixture comprising (i) organic phase containing at least dissolved catalyst residue(s) in whatever chemical composition it exists or they exist while in said organic phase, (ii) aqueous phase containing at least dissolved inorganic salt of said arylalkylcarboxylic acid or substituted arylalkylcarboxylic acid in whatever chemical composition it exists while in said aqueous phase, and (iii) a solids phase containing at least palladium and/or one or more palladium compounds in whatever chemical composition it exists or they exist while in said solids phase;
D) separating said phases from each other; and
E) recycling to A) or to B) at least a portion of the separated solids-free organic phase containing dissolved catalyst residue(s) to serve as (i) a portion of the reaction mixture for additional palladium-catalyzed arylation of 1-olefin pursuant to A), or (ii) a portion of the reaction mixture for additional palladium-catalyzed hydracarbonylation of arylolefin or substituted arylolefin pursuant to B), as the case may be, or alternatively, recycling to A) and to B) separate portions of the separated solids-free organic phase containing dissolved catalyst residue(s) to serve as (i) a portion of the reaction mixture for additional palladium-catalyzed arylation of 1-olefin pursuant to A), and (ii) a portion of the reaction mixture for additional palladium-catalyzed hydracarbonylation of arylolefin or substituted arylolefin pursuant to B).

137. A process according to claim 136 further comprising recovering at least a portion of said solids phase and converting recovered solids phase into fresh palladium-containing catalyst for use in conducting (i) additional palladium-catalyzed arylation of 1-olefin pursuant to A), and/or (ii) additional palladium-catalyzed hydracarbonylation of arylolefin or substituted arylolefin pursuant to B).

138. A process according to claim 136 wherein said arylation catalyst when fresh is formed at least from (1) palladium or palladium compound and (2) organophosphine ligand.

139. A process according to claim 136 wherein said hydrocarbonylation catalyst when fresh is formed at least from (1) palladium or palladium compound and (2) organophosphine ligand.

140. A process according to claim 136 wherein said arylation catalyst when fresh is formed at least from (1) palladium or palladium compound and (2) organophosphine ligand, and wherein said hydrocarbonylation catalyst when fresh is formed at least from (1) palladium or palladium compound and (2) organophosphine ligand.

141. A process according to claim 136 wherein said arylation catalyst when fresh is formed at least from (1) palladium(II) halide or carboxylate and (2) trihydrocarbylphosphine ligand.

142. A process according to claim 136 wherein said hydrocarbonylation catalyst when fresh is formed at least from (1) palladium(II) halide or carboxylate and (2) trihydrocarbylphosphine ligand.

143. A process according to claim 136 wherein said arylation catalyst when fresh is formed at least from (1)

palladium(II) halide or carboxylate and (2) trihydrocarbylphosphine ligand, and wherein said hydracarbonylation catalyst when fresh is formed at least from (1) palladium(II) halide or carboxylate and (2) trihydrocarbylphosphine ligand.

144. A process which comprises
  A) conducting a palladium-catalyzed arylation of ethylene in a first reaction mixture formed at least from aryl halide or substituted aryl halide, polar organic solvent, hydrogen halide acceptor, and palladium arylation catalyst to produce a first reaction product mixture comprising as constituents at least arylolefin or substituted arylolefin, polar organic solvent, product of hydrogen halide and hydrogen halide acceptor, and catalyst residue(s) in whatever chemical composition and form said respective constituents exist in said first reaction product mixture;
  B) conducting a palladium-catalyzed hydracarbonylation of arylolefin or substituted arylolefin formed in A) with carbon monoxide in a second reaction mixture formed at least from polar organic solvent, water, palladium hydracarbonylation catalyst, and aqueous HCl to produce a second reaction product mixture comprising as constituents at least arylalkylcarboxylic acid or substituted arylalkylcarboxylic acid, polar organic solvent, and catalyst residue(s) in whatever chemical composition and form said respective constituents exist in said second reaction product mixture;
  C) removing a portion of the polar organic solvent from said second reaction product mixture to form a more concentrated second reaction product mixture;
  D) mixing with at least a portion of said more concentrated second reaction product mixture an aqueous solution of inorganic base to thereby form a mixture comprising (i) organic phase containing dissolved catalyst residue(s) in whatever chemical composition it exists or they exist while in said organic phase, (ii) aqueous phase containing at least dissolved inorganic salt of said arylalkylcarboxylic acid or substituted arylalkylcarboxylic acid in whatever chemical composition it exists while in said aqueous phase, and (iii) a solids phase containing at least palladium and/or one or more palladium compounds in whatever chemical composition it exists or they exist while in said solids phase;
  E) separating said phases from each other; and
  F) recycling to A) or to B) at least a portion of the separated solids-free organic phase containing at least said dissolved catalyst residue(s) to serve as (i) a portion of the reaction mixture for use in additional palladium-catalyzed arylation of ethylene pursuant to A), or (ii) a portion of the reaction mixture for use in additional palladium-catalyzed hydracarbonylation of arylolefin or substituted arylolefin pursuant to B), as the case may be, or alternatively, recycling to A) and to B) separate portions of the separated solids-free organic phase containing at least dissolved catalyst residue(s) to serve as (i) a portion of the reaction mixture for use in additional palladium-catalyzed arylation of ethylene pursuant to A), and (ii) a portion of the reaction mixture for additional palladium-catalyzed hydracarbonylation of arylolefin or substituted arylolefin pursuant to B).

145. A process according to claim 144 further comprising recovering at least a portion of said solids phase and converting recovered solids phase into fresh palladium-containing catalyst for use in conducting (i) additional palladium-catalyzed arylation of ethylene pursuant to A), and/or (ii) additional palladium-catalyzed hydracarbonylation of arylolefin or substituted arylolefin pursuant to B).

146. A process according to claim 144 wherein said arylation catalyst when fresh is formed at least from (1) palladium or palladium compound and (2) organophosphine ligand.

147. A process according to claim 144 wherein said hydracarbonylation catalyst when fresh is formed at least from (1) palladium or palladium compound and (2) organophosphine ligand.

148. A process according to claim 144 wherein said arylation catalyst when fresh is formed at least from (1) palladium or palladium compound and (2) organophosphine ligand, and wherein said hydracarbonylation catalyst when fresh is formed at least from (1) palladium or palladium compound and (2) organophosphine ligand.

149. A process according to claim 144 wherein said arylation catalyst when fresh is formed at least from (1) palladium(II) halide or carboxylate and (2) trihydrocarbylphosphine ligand.

150. A process according to claim 144 wherein said hydracarbonylation catalyst when fresh is formed at least from (1) palladium(II) halide or carboxylate and (2) trihydrocarbylphosphine ligand.

151. A process according to claim 144 wherein said arylation catalyst when fresh is formed at least from (1) palladium(II) halide or carboxylate and (2) trihydrocarbylphosphine ligand, and wherein said hydracarbonylation catalyst when fresh is formed at least from (1) palladium(II) halide or carboxylate and (2) trihydrocarbylphosphine ligand.

152. A process according to claim 144 wherein the aryl halide or substituted aryl halide used in A) is m-bromobenzophenone or 2-bromo-6-methoxynaphthalene, wherein the polar organic solvent used in A) and in B) is at least predominately at least one liquid ketone, and wherein the hydrohalide acceptor used in A) is triethylamine.

153. A process according to claim 152 wherein said arylation catalyst when fresh is formed at least from (1) palladium(II) halide or carboxylate and (2) neomenthyldiphenylphosphine or trihydrocarbylphosphine in which the hydrocarbyl groups are aryl or alkyl-substituted aryl groups, and wherein said hydracarbonylation catalyst when fresh is formed at least from (1) palladium(II) halide or carboxylate and (2) neomenthyldiphenylphosphine or trihydrocarbylphosphine in which the hydrocarbyl groups are aryl or alkyl-substituted aryl groups, wherein the dissolved catalyst residue(s) of said organic phase containing dissolved catalyst residue(s) in D) comprise(s) neomenthyldiphenylphosphine or trihydrocarbylphosphine in which the hydrocarbyl groups are aryl or alkyl-substituted aryl groups, at least a portion of which neomenthyldiphenylphosphine or trihydrocarbylphosphine in which the hydrocarbyl groups are aryl or alkyl-substituted aryl groups is recycled pursuant to F).

154. A process which comprises:
  a) conducting a palladium-catalyzed arylation of an olefin, with aryl halide and/or substituted aryl halide, in a liquid medium formed from (i) at least one liquid dialkylketone solvent/diluent having 6 carbon atoms in the molecule, and (ii) at least one secondary or tertiary amine that boils below the boiling temperature of the ketone solvent/diluent, to form a reaction mixture comprising olefinically-substituted aromatic compound, amine-hydrohalide and the ketone solvent/diluent;
  b) recovering from said reaction mixture a solution composed principally of the olefinically-substituted aromatic compound in the ketone solvent/diluent; and c) conducting a palladium-catalyzed carbonylation of at least a portion of said olefinically-substituted aromatic compound with carbon monoxide and water and/or alcohol in said ketone solvent/diluent to produce arylalkylcarboxylic acid and/or substituted arylalkylcarboxylic acid and/or, if alcohol was present, arylalkylcarboxylic acid ester and/or substituted arylalkylcarboxylic acid ester.

155. A process according to claim 154 wherein the aryl halide and/or substituted aryl halide used in a) is 4-isobutyl-1-bromobenzene, m-bromobenzophenone, or 2-bromo-6-methoxy-naphthalene.

156. A process according to claim 154 wherein the liquid dialkyl ketone solvent/diluent in a) and in c) is methyl isobutyl ketone.

157. A process according to claim 154 wherein the palladium-catalyzed carbonylation conducted in c) is palladium-catalyzed hydracarbonylation with carbon monoxide and water.

158. A process according to claim 154 wherein the aryl halide and/or substituted aryl halide used in a) is 2-bromo-6-methoxynaphthalene, and wherein the liquid dialkyl ketone solvent/diluent in a) and in c) is methyl isobutyl ketone.

159. A process according to claim 158 wherein the amine in a) is triethylamine, and wherein the palladium-catalyzed carbonylation conducted in c) is palladium-catalyzed hydracarbonylation with carbon monoxide and water.

160. A process according to claim 154 wherein the palladium catalyst used in a) and the palladium catalyst used in c) are each formed from ingredients comprising a palladium(II) salt, and a trihydrocarbylphosphine (i) in which the three hydrocarbyl groups are, independently, aryl or alkyl-substituted aryl or (ii) in which two of the hydrocarbyl groups are, independently, aryl or alkyl-substituted aryl groups, and the third hydrocarbyl group is a cycloalkyl or an alkyl-substituted cycloalkyl group.

161. A process according to claim 154 wherein the palladium catalyst used in a) is formed from ingredients comprising palladium(II) chloride or acetate, and neomenthyldiphenylphosphine.

162. A process according to claim 154 wherein a reaction-accelerating amount of water in the range of about 0.5 to about 5 wt % of the total weight of the entire reaction mixture is included or present in the reaction mixture of a) when the reaction is initiated.

163. A process according to claim 162 wherein the aryl halide and/or substituted aryl halide used in a) is 2-bromo-6-methoxynaphthalene, and wherein said amount of water is in the range of about 1 to about 2 wt % relative to the total weight of the 2-bromo-6-methoxynaphthalene, the ketone solvent/diluent, the amine and the water.

164. A process according to claim 163 wherein the amine in a) is triethylamine, wherein the liquid dialkyl ketone solvent/diluent in a) and in c) is methyl isobutyl ketone, and wherein the palladium-catalyzed carbonylation conducted in c) is palladium-catalyzed hydracarbonylation with carbon monoxide and water.

165. A process according to claim 164 wherein the palladium catalyst used in a) and the palladium catalyst used in c) are each formed from ingredients comprising a palladium(II) salt, and a trihydrocarbylphosphine (i) in which the three hydrocarbyl groups are, independently, aryl or alkyl-substituted aryl or (ii) in which two of the hydrocarbyl groups are, independently, aryl or alkyl-substituted aryl groups, and the third hydrocarbyl group is a cycloalkyl or an alkyl-substituted cycloalkyl group.

166. A process according to claim 164 wherein the palladium catalyst used in a) is formed from ingredients comprising palladium(II) chloride or acetate, and neomenthyldiphenylphosphine.

167. A process according to claim 154 wherein the recovery in b) of the solution of olefinically-substituted aromatic compound in methyl isobutyl ketone solvent/diluent comprises mixing together at least a portion of the reaction product from a) and an aqueous inorganic base solution of sufficient basicity to liberate the amine to thereby form an aqueous basic saline phase and an organic phase composed of a solution of the olefinically-substituted aromatic compound and amine in the ketone solvent/diluent; distilling said amine from the resultant mixture, and then making a phase cut between the aqueous basic saline phase and the organic phase composed principally of a solution of the olefinically-substituted aromatic compound in the ketone solvent diluent.

168. A process according to claim 167 wherein the aryl halide and/or substituted aryl halide used in a) is 2-bromo-6-methoxynaphthalene; wherein the liquid dialkyl ketone solvent/diluent in a) and in c) is methylisobutyl ketone; wherein the amine in a) is triethylamine; wherein a reaction-accelerating amount of water in the range of about 1 to about 2 wt % relative to the total weight of the 2-bromo-6-methoxynaphthalene, the methyl isobutyl ketone solvent/diluent, the triethylamine and the water is included or present in the reaction mixture of a) when the reaction is initiated; wherein the palladium catalyst used in a) and the palladium catalyst used in c) are each formed from ingredients comprising a palladium(II) salt, and a trihydrocarbylphosphine (i) in which the three hydrocarbyl groups are, independently, aryl or alkyl-substituted aryl or (ii) in which two of the hydrocarbyl groups are, independently, aryl or alkyl-substituted aryl groups, and the third hydrocarbyl group is a cycloalkyl or an alkyl-substituted cycloalkyl group; and wherein the palladium-catalyzed carbonylation conducted in c) is palladium-catalyzed hydracarbonylation with carbon monoxide and water.

169. A process according to claim 168 wherein said palladium catalyst used in a) and said palladium catalyst used in c) are each formed from ingredients comprising palladium(II) chloride or acetate, and neomenthyldiphenylphosphine.

170. A process according to claim 154 wherein the carbonylation of c) is conducting by a process comprising:
1) feeding a solution of said olefinically-substituted aromatic compound in liquid dialkyl ketone solvent/diluent having 6 carbon atoms in the molecule into a reaction vessel containing a heel formed from ingredients which initially comprised at least aqueous hydrochloric acid, liquid dialkyl ketone solvent/diluent having 6 carbon atoms in the molecule corresponding to the solvent/diluent in the feed, palladium or a palladium compound, a trihydrocarbylphosphine, and optionally an alcohol; and
2) heating the contents of the reactor and charging carbon monooxide into the reactor under pressure during at least a portion of the feeding in a) such that carbonylation of the olefinically-substituted aromatic compound occurs to form arylalkylcarboxylic acid or substituted arylalkylcarboxylic acid, or if alcohol is present, to form arylalkylcarboxylic acid ester or substituted arylalkylcarboxylic acid ester.

171. A process according to claim 170 wherein said olefinically-substituted aromatic compound is 6-methoxy-2-vinylnaphthalene, wherein said liquid dialkyl ketone solvent/diluent in said solution of 1) and in said heel of 1) is methyl isobutyl ketone, wherein the palladium or a palladium compound in 1) initially was a palladium(II) salt, wherein the trihydrocarbylphosphine in 1) initially was (i) a trihydrocarbylphosphine in which the three hydrocarbyl groups were, independently, aryl or alkyl-substituted aryl or (ii) a trihydrocarbylphosphine in which two of the hydrocarbyl groups were, independently, aryl or alkyl-substituted aryl groups, and the third hydrocarbyl group were a cycloalkyl or an alkyl-substituted cycloalkyl group, and wherein the carbonylation in 2). is hydracarbonylation using carbon monoxide and water.

172. A process according to claim 171 wherein the concentration of the solution of 6-methoxy-2-vinylnaphthalene in methyl isobutyl ketone fed into the reactor is in the range of about 15 to about 30 wt %, wherein the palladium(II) salt of the heel initially was palladium(II) chloride or acetate, wherein the trihydrocarbylphosphine of the heel initially was neomenthyldiphenylphosphine, wherein said ingredients from which said heel was formed further initially comprised 6-methoxy-2-vinylnaphthalene, and wherein the hydracarbonylation is conducted at a temperature in the range of about 70 to about 100° C.

173. A process comprising:
  a) feeding a solution containing up to about 40 wt % of olefinically-substituted aromatic compound in a liquid organic solvent/diluent into a reaction vessel containing a heel formed from ingredients which initially comprised at least aqueous hydrochloric acid, liquid organic solvent/diluent corresponding to the solvent/diluent in the feed, palladium or a palladium compound, a trihydrocarbylphosphine, and optionally an alcohol;
  b) heating the contents of the reactor and charging carbon monooxide into the reactor under pressure during at least a portion of the feeding in a) such that carbonylation of the olefinically-substituted aromatic compound occurs to thereby form arylalkylcarboxylic acid or substituted arylalkylcarboxylic acid, or if alcohol is present, to form arylalkylcarboxylic acid ester or substituted arylalkylcarboxylic acid ester.

174. A process according to claim 173 wherein said ingredients from which said heel is formed further initially comprised olefinically-substituted aromatic compound corresponding to the olefinically-substituted aromatic compound in the feed.

175. A process according to claim 173 wherein said olefinically-substituted aromatic compound is 4-isobutylstyrene, m-vinylbenzophenone, or 6-methoxy-2-vinylnaphthalene.

176. A process according to claim 173 wherein said liquid organic solvent/diluent in said solution and in said heel consists essentially of at least one liquid dialkyl ketone solvent/diluent having 6 carbon atoms in the molecule.

177. A process according to claim 173 wherein said olefinically-substituted aromatic compound in said solution is 6-methoxy-2-vinylnaphthalene, wherein said liquid organic solvent/diluent in said solution and in said heel consists essentially of methyl isobutyl ketone, and wherein said ingredients from which said heel is formed further initially comprised 6-methoxy-2-vinylnaphthalene.

178. A process according to claim 177 wherein the palladium or palladium compound in a) initially was a palladium(II) salt, and wherein the trihydrocarbylphosphine in a) initially was (i) a trihydrocarbylphosphine in which the three hydrocarbyl groups were, independently, aryl or alkyl-substituted aryl or (ii) a trihydrocarbylphosphine in which two of the hydrocarbyl groups were, independently, aryl or alkyl-substituted aryl groups, and the third hydrocarbyl group were a cycloalkyl or an alkyl-substituted cycloalkyl group.

179. A process according to claim 178 wherein the palladium(II) salt initially was palladium(II) chloride or acetate, and wherein the trihydrocarbylphosphine initially was neomenthyldiphenylphosphine.

180. A process according to claim 178 wherein at least a portion of the palladium(II) salt ingredient used in forming the heel was fresh palladium(II) salt, and wherein at least a portion of the trihydrocarbylphosphine ingredient used in forming said heel was fresh trihydrocarbylphosphine.

181. A process according to claim 180 wherein the ingredients from which the heel was formed further comprise reaction mass from a prior analogous carbonylation reaction.

* * * * *